(12) United States Patent
Tamura et al.

(10) Patent No.: US 9,040,254 B2
(45) Date of Patent: May 26, 2015

(54) METHODS FOR DETECTING AN ENDOTOXIN USING A HORSESHOE CRAB CLOTTING ENZYME

(71) Applicant: SEIKAGAKU CORPORATION, Tokyo (JP)

(72) Inventors: Hiroshi Tamura, Tokyo (JP); Shoji Takahashi, Tokyo (JP)

(73) Assignee: SEIKAGAKU CORPORATION, Tokyo (JP)

( * ) Notice: Subject to any disclaimer, the term of this patent is extended or adjusted under 35 U.S.C. 154(b) by 0 days.

(21) Appl. No.: 13/942,293

(22) Filed: Jul. 15, 2013

(65) Prior Publication Data

US 2013/0309701 A1 Nov. 21, 2013

Related U.S. Application Data

(62) Division of application No. 12/307,890, filed as application No. PCT/JP2007/063606 on Jul. 6, 2007, now abandoned.

(30) Foreign Application Priority Data

Jul. 7, 2006 (JP) ................. 2006-188523

(51) Int. Cl.
| | |
|---|---|
| *C12Q 1/37* | (2006.01) |
| *C12Q 1/56* | (2006.01) |
| *C07K 14/435* | (2006.01) |
| *C12N 9/64* | (2006.01) |
| *G01N 33/579* | (2006.01) |

(52) U.S. Cl.
CPC ............ *C12Q 1/56* (2013.01); *C07K 14/43509* (2013.01); *C12N 9/6402* (2013.01); *G01N 33/579* (2013.01); *C12N 2799/026* (2013.01)

(58) Field of Classification Search
None
See application file for complete search history.

(56) References Cited

U.S. PATENT DOCUMENTS

| 5,681,710 | A | 10/1997 | Tanaka et al. |
|---|---|---|---|
| 2003/0054432 | A1 | 3/2003 | Chen et al. |
| 2006/0228779 | A1 | 10/2006 | Tamura |
| 2007/0134227 | A1 | 6/2007 | Tanaka et al. |

FOREIGN PATENT DOCUMENTS

| CN | 1030138 A | 1/1989 |
|---|---|---|
| EP | 0074761 A1 | 3/1983 |
| EP | 0 291 856 | 5/1988 |
| EP | 0426395 A1 | 5/1991 |
| EP | 0549102 A1 | 6/1993 |
| EP | 0649021 A1 | 9/1994 |
| EP | 0837330 A2 | 4/1998 |
| EP | 1707574 A1 | 10/2006 |
| JP | 2005-500520 A | 1/2005 |
| JP | 2006-271384 A | 10/2006 |
| WO | 99/15676 A1 | 4/1999 |
| WO | 03/002976 A2 | 1/2003 |
| WO | 2004/097022 A1 | 11/2004 |

OTHER PUBLICATIONS

Petty, Metal-chelate affinity chromatography. In: Current Protocols in Molecular Biology (1996) John Wiley & Sons, Inc. pp. 9.4.1-9.4.16.*
Chinese Office Action, issued Sep. 9, 2013, in corresponding Chinese Patent Application No. 201210272731.2.
Wu Weihong et al., Preparation and identification of a more sensitive and specific agent comprising a recombined pro-clotting enzyme derived from Horseshoe Crab, Factors B and C (called a Horseshoe Crab, factors BC agent in brief), Chinese Journal of Modern Applied Pharmacy, 1987, 4(6):1-4.
Extended Search Report issued in counterpart European Patent Application No. 07768331.6 on Nov. 17, 2009 (in the name of Seikagaku Corporation).
Extended Search Report issued in counterpart European Patent Application No. 12156002.3 on Aug. 7, 2012 (in the name of Seikagaku Corporation).
Extended Search Report issued in counterpart European Application No. 12156015.5 on Aug. 7, 2012 (in the name of Seikagaku Corporation).
Jeak L. Ding et al., "A new era in pyrogen testing", TRENDS in Biotechnology, 2001, 19(8): 277-281.
Richard B. Gayle, III et al., "Identification of Regions in Interleukin-1α Important for Activity", The Journal of Biological Chemistry, 1993, 268(29): 22105-22111.
Haiwei H. Guo et al., "Protein tolerance to random amino acid change", PNAS, 2004, 101(25): 9205-9210.
Sadaaki Iwanaga, "The limulus clotting reaction", Current Opinion in Immunology, 1993, 5(1): 74-82.
Sadaaki Iwanaga et al., "Role of Hemocyte-Derived Granular Components in Invertebrate Defense", Annals New York Academy of Science, 1994, 712: 102-116.
Sadaaki Iwanaga et al., "Evolution and Phylogeny of Defense Molecules Associated with Innate Immunity in Horseshoe Crab", Frontiers in Bioscience 3,1998, 973-984.
Shu-Mei Liang et al., "Studies on the Limulus Coagulation System: Inhibition of Activation of the Proclotting Enzyme, by Dimethyl Sulfoxide", Biochemical Biophysical Research Communications, 1982, 105(2): 553-9.
T. Morita et al., "A new (1→3)-β-D-Glucan-Mediated Coagulation Pathway Found in Limulus Amebocytes", FEBS Letters, 1981, 129(2):318-321.

(Continued)

*Primary Examiner* — Sheridan Swope
(74) *Attorney, Agent, or Firm* — Sughrue Mion, PLLC

(57) ABSTRACT

Objects of the present invention are to provide a DNA fragment encoding a *limulus*-derived pro-clotting enzyme, a virus harboring the DNA fragment, a cell harboring the virus, a method of producing the pro-clotting enzyme by use of the cell, and means for assaying an endotoxin or (1→3)-β-D-glucan employing the enzyme, wherein these elements are capable of producing an endotoxin or (1→3)-β-D-glucan assay reagent of satisfactory quality, steadily, at low cost, and on a large scale. In the present invention, for example, a DNA fragment encoding a protein having an amino acid sequence defined by SEQ ID NO: 4 is selected as a nucleic acid fragment encoding a *limulus*-derived pro-clotting enzyme, and the corresponding recombinant pro-clotting enzyme. Use of the enzyme can provide a high-sensitivity method and kit for detecting (1→3)-β-D-glucan and an endotoxin, utilizing a cascade reaction system in a horseshoe crab lysate.

5 Claims, 9 Drawing Sheets

(56) References Cited

OTHER PUBLICATIONS

Cheryl Isaac Murphy et al., Expression of Proteins in Insect Cells Using Baculovirus Vectors, Current Protocols in Molecular Biology, 2004, Supplement 65, 16.9.1-16.9.10.

Tatsushi Muta et al., "Proclotting Enzyme from Horseshoe Crab Hemocytes", The Journal of Biological Chemistry, 1990, 265(36): 22426-22433.

Tatsushi Muta et al., "Horseshoe Crab Coagulation Factor B," The Journal of Biochemistry, 1993, 268(28): 21384-21388.

Tatsushi Muta et al., "Purified Horseshoe Crab Factor G", The Journal of Biological Chemistry, 1995, 270(2): 892-897.

T. Muta et al., "Clotting and Immune Defense in Limulidae", Prog Mol Subcell Biol., 1996, 15: 154-189.

Shin Nakamura et al., "A Clottable Protein (Coagulogen) of Horseshoe Crab Hemocytes: Structural Change of Its Polypeptide Chain During Gel Formation", J. Biochem.,1976, 80(3): 649-652.

Shin Nakamura et al., "Fractionation of *Limulus* Amebocyte Lysate: Characterization of Activation of the Proclotting Enzyme by an Endotoxin-Mediated Activator", Biochim Biophys Acta.,1982, 707(2): 217-25.

Takanori Nakamura et al., "Intracellular Proclotting Enzyme in Limulus (*Tachypleus tridentatus*) Hemocytes: Its Purification and Properties," J. Biochem., 1985, 97(6): 1561-1574.

Takanori Nakamura et al., "Purification and Properties of Intracellular Clotting Factor, Factor B, from Horseshoe Crab (*Tachypleus tridentatus*) Hemocytes," J. Biochem., 1986, 99(3): 847-857.

Takanori Nakamura et al., "Lipopolysaccharide-Sensitive Serine-Protease Zymogen (Factor C) Found in Limulus Hemocytes," Eur. J. Biochem., 1986, 154: 511-521.

Keat G. Ong et al., A Rapid Highly-Sensitive Endotoxin Detection System, Biosensors and Bioelectronics, 2006, 21: 2270-2274.

Kevin J. Petty, "Metal-Chelate Affinity Chromatography", Current Protocols n Protein Science, 1996, Supplement 4, 9.4.1-9.4.16.

Robert I. Roth et al., "Purification of *Limulus polyphemus* Proclotting Enzyme," The Journal of Biochemistry, 1992, 267(33): 24097-24102.

Joseph Y. Tai et al., "Studies on *Limulus* Amoebocyte Lysate: Isolation of pro-clotting enzyme", The Journal of Biological Chemistry, 1977, 252(7): 2178-2181.

Shigenori Tanaka et al., "Limulus Anti-LPS Factor: an Anticoagulant Which Inhibits the Endotoxin-Mediated Activation of Limulus Coagulation System", Biochemical and Biophysical Research Community, 1982, 105: 717-723.

Kiyoshi Tsuji et al., "Use of Magnesium to Increase Sensitivity of *Limulus* Amoebocyte Lysate for Detection of Endotoxin", Applied and Environmental Microbiology, 1983, 45(4): 1342-1350.

James C. Whisstock et al., "Prediction of protein function from protein sequence and structure", Quarterly Reviews of Biophysics, 2003, 36(3): 307-340.

Office Action issued in counterpart European Application No. 12156002.3, dated Oct. 8, 2013.

Office Action issued in counterpart European Application No. 12156015.5, dated Oct. 8, 2013.

Office Action dated May 29, 2014, issued in counterpart Chinese Patent Application No. 201210272731.2.

Yang Zhongsi et al., "Research progress in detection of endotoxin in pyrogens and bacteria", Medical Recapitulate, 2005, vol. 11, No. 2, 142-144.

Decision of Rejection, dated Mar. 18, 2014, issued in counterpart Japanese Patent Application No. 2008-523763.

Shigeru Ariki et al., "A serine protease zymogen functions as a pattern-recognition reception for lipopolysaccharides", PNAS, 2004, vol. 101, No. 4, 953-958.

Takanori Nakamura et al., "Lipopolysaccharide-Sensitive Serine-Protease Zymogen (Factor C) Found in Limulus Hemocytes", Eur. J. Biochem.,1986, 154:511-521.

Communication, dated Mar. 17, 2015, issued by the European Patent Office in counterpart European Application No. 12 156 002.3.

* cited by examiner

Fig. 1

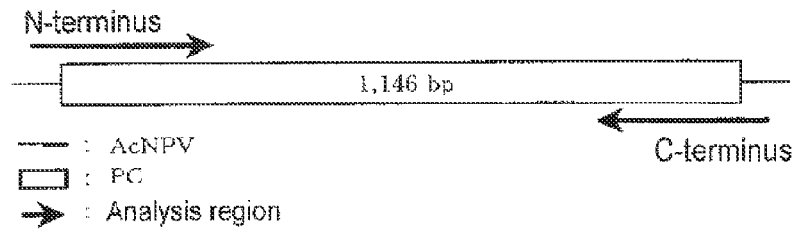

- N-terminus
```
TAATCGCGAT CTAGAATGTT GGTGAATAAC GTCTTTTCAC TACTCTCTTT CCCACTCTTG
           *****      ********** ********** ********** **********
           ATGTT      GGTGAATAAC GTCTTTTCAC TACTGTCTTT CCCACTCTTG ATGTCTGTGG TTAGATCCAG TACTCTCAGC AGACAGCGTA GACACTTTGT TTTCCCTGAC
******** ****** ****** ****** ****** ********
ATGTCTGTGG TTAGATCCAG TACTCTCAGC AGACAGCGTA GACACTTTGT TTTCCCTGAC GAGGAAGAAC TTTGCTCAAA CCGATTTACT GAAGAAGGAA CATGCAAAAA TGTCTTGGAT
******** ****** ****** ****** ****** ********
GAGGAAGAAC TTTGCTCAAA CCGATTTACT GAAGAAGGAA CATGCAAAAA TGTCTTGGAT TGTAGAATAC TTTTACAAAA AAATGATTAT AATTTACTCA AAGAATCAAT ATGCGGCTTT
******** ****** ****** ***** ****** ********
TGTAGAATAC TTTTACAAAA AAATGATTAT AATTTACTCA AAGAATCAAT ATGCGGCTTT GAAGGCATAA CACCCAAAGT TTGTTGTCCG AAATCAAGCC ATGTAATTTC AAGTACACAG
******** ****** ****** ****** ****** ********
GAAGGCATAA CACCCAAAGT TTGTTGTCCG AAATCAAGCC ATGTAATTTC AAGTACACAG
```

- C-terminus
```
CNCNTNACAA GCGGTCTTAT TATTAAATCT AGTGATGGTG ATGGTGATGC ACCATATGTT
                  **  ********** ********** ********** **********
                  CT  AGTGATGGTG ATGGTGATGC ACCATATGTT CTGCAATCCA ATCTAAAAAC TCTGTCACTT TTGTGTAAAC CCCAGGAAAT CCAGGCAATG
******** ****** ****** ****** ****** ********
CTGCAATCCA ATCTAAAAAC TCTGTCACTT TTGTGTAAAC CCCAGGAAAT CCAGGCAATG CGCATTTCTT TCCGAAAGAC ACAATTCCAA TGAGATAAAA CTCTCCGGTT TTAACAGGCA
******** ****** ****** ****** ****** ********
CGCATTTCTT TCCGAAAGAC ACAATTCCAA TGAGATAAAA CTCTCCGGTT TTAACAGGCA ACATCATTGG ACCTCCAGAA TCACCCTGGC AAGCATCCTT CCCGCCATCT GCAAAGCCAG
******** ****** ****** ****** ****** ********
ACATCATTGG ACCTCCAGAA TCACCCTGGC AAGCATCCTT CCCGCCATCT GCAAAGCCAG CACACATATA CACGTTTGTA ATATTTAAAT CCTTCTCGTA GGCCTGTCTA CAGGCCTCGT
******** ****** ****** ****** ****** ********
CACACATATA CACGTTTGTA ATATTTAAAT CCTTCTCGTA GGCCTGTCTA CAGGCCTCGT GTTCCCATAT TGGTAACTGT ACTTCTCTCA ACACTGCACT AGATGGGCCG TTAAATGCTC
******** ****** ****** ****** ****** ********
GTTCCCATAT TGGTAACTGT ACTTCTCTCA ACACTGCACT AGATGGGCCG TTAAATGCTC
```

METHODS FOR DETECTING AN ENDOTOXIN USING A HORSESHOE CRAB CLOTTING ENZYME

This is a divisional of U.S. patent application Ser. No. 12/307,890 filed Feb. 17, 2009 (now abandoned), which is a 371 National Stage Entry of PCT/JP2007/063606 filed Jul. 6, 2007, which claims priority of Japanese Patent Application No. 2006-188523 filed Jul. 7, 2006, the contents of all of which are incorporated herein by reference in their entirety.

BACKGROUND OF THE INVENTION

Background Art

There are disclosed methods for determining Et or BG by use of an amebocyte lysate of a horseshoe crab (i.e., a horseshoe crab hematocyte extract, hereinafter referred to simply as a lysate). These methods are based on coagulation of the lysate by Et or BG. The coagulation reaction occurs through cascade reaction of several coagulation factors (Patent Document 1 and Non-Patent Document 1).

For example, when BG is brought into contact with the lysate, factor G contained in the lysate is activated, to thereby form activated factor G. The activated factor G activates Pro-CE present in the lysate, to thereby form CE. CE hydrolyzes a specific site of a coagulogen molecule present in the lysate, thereby forming coaguline gel, leading to coagulation of the lysate. CE also acts on a synthetic substrate (e.g., t-butoxy-carbonyl-leucyl-glycyl-arginine-pNA (Boc-Leu-Gly-Arg-pNA)), to thereby hydrolyze the amino bonds, whereby pNA is released. Thus, BG can be determined through measuring absorbance of the formed coloring substance (pNA) (Patent Document 1).

Although Pro-CE was previously cloned (Non-Patent Document 2), a protein (Pro-CE) maintaining an enzymatic activity is difficult to develop when the corresponding nucleic acid fragment is employed.

In other words, although Pro-CE was previously cloned, the technique and the resultant protein disclosed in Non-Patent Document 2 are merely included in a standard technique for producing a target clone of a cDNA fragment encoding a protein of interest. More specifically, the standard technique is limited to selection of 23 clones from a λgt11 cDNA library (1,500,000 clones) by use of an anti-CE antibody, subcloning to a pUC118/119 vector, and determination of the nucleotide sequence. In fact, these working steps are considerably heavy, and there have not yet been performed development of an enzymatic activity of Pro-CE, which is a precursor of serine protease [protease (amidase) activity of CE], and activation of Pro-CE by activated factor B or quantitative determination (including reproduction test) of the enzymatic activity of Pro-CE in the co-presence of activated factor B or C. Completely differing from determination of the nucleotide sequence of a specific protein, yielding the specific protein as a recombinant and establishing a specific assay system employing the recombinant protein can be attained only by highly advanced creation of technical ideas.

Patent Document 1: Japanese Patent Application laid-Open (kokai) No. 08-122334
Patent Document 2: Japanese Patent Application laid-Open (kokai) No. 2006-271384
Non-Patent document 1: J. Protein Chem., 5, p. 255-268 (1986)
Non-Patent document 2: J. Biol. Chem., 265(36), p. 22426-22433 (1990)

BRIEF SUMMARY OF THE INVENTION

Problems to be Solved by the Invention

Thus, objects of the present invention are to provide a nucleic acid fragment encoding a *limulus*-derived Pro-CE, a virus harboring the nucleic acid fragment, a cell harboring the virus, a method of producing the Pro-CE by use of the cell, and a method and a kit for detecting Et or BG employing the Pro-CE produced through the production method, wherein these elements are capable of mass-producing an Et or BG assay reagent of satisfactory quality, steadily, at low cost, and on a large scale.

The present inventors have conducted extensive studies in order to attain the aforementioned objects, and have found that a protein having Pro-CE activity can be produced by use of a cell harboring a virus containing a DNA fragment encoding Pro-CE, whereby an Et or BG assay reagent of satisfactory quality can be mass-produced steadily, at low cost, and on a large scale. The present invention has been accomplished on the basis of this finding.

Abbreviations used in the present invention (including the aforementioned "Background") are as follows.
Pro-CE: pro-clotting enzyme
CE: clotting enzyme
AcNPV: nuclear polyhedrosis virus of *Autographa californica*
BG: (1→3)-β-D-glucan
Et: endotoxin (also referred to as lipopolysaccharide)
HEPES: 2-[4-(2-hydroxyethyl)-1-piperazinyl]ethanesulfonic acid
HRP: horseradish peroxidase
MOI: multiplicity of infection
NPV: nuclear polyhedrosis virus
PBS: phosphate buffered saline
PCR: polymerase chain reaction
pNA: p-nitroaniline
PVDF: polyvinylidene difluoride
SDS: sodium dodecyl sulfate
SDS-PAGE: sodium dodecyl sulfate-polyacrylamide gel electrophoresis
LAL: *limulus amebocyte* lysate Accordingly, the present invention provides a nucleic acid fragment encoding a *limulus*-derived Pro-CE (hereinafter the nucleic acid fragment may be referred to as a "nucleic acid fragment of the present invention").

The horseshoe crab (*limulus*) employed in the present invention is selected from among the following four species: *Tachypleus tridentatus, Limulus polyphemus, Tachypleus gigas,* and *Tachypleus rotundicauda (Carcinoscorpius rotundicauda).*

The "nucleic acid fragment encoding a *limulus*-derived Pro-CE" employed in the invention is preferably selected from the following nucleic acid fragments (A) to (C):

(A) a DNA fragment encoding a protein having an amino acid sequence defined by SEQ ID NO: 4, (B) a DNA fragment encoding a protein having an amino acid sequence defined by SEQ ID NO: 4 in which one or several amino acid residues are deleted, substituted, inserted, or translocated, and having activity of a *limulus*-derived Pro-CE, and (C) an RNA fragment produced through transcription of the DNA fragment (A) or (B).

The "nucleic acid fragment encoding a *limulus*-derived Pro-CE" employed in the invention is preferably selected from the following nucleic acid fragments (a) to (c):

(a) a DNA fragment having a nucleotide sequence defined by nucleotides 1 to 1143 in SEQ ID NO: 3, (b) a DNA fragment having a nucleotide mutation in a nucleotide sequence containing a nucleotide sequence defined by nucleotides 1 to 1143 in SEQ ID NO: 3, wherein the mutation causes deletion, substitution, insertion, or translocation of one or several amino acid residues in an amino acid sequence of a protein encoded by the nucleotide sequence defined by nucleotides 1 to 1143 in SEQ ID NO: 3, and a protein expressed by the DNA fragment having a nucleotide mutation has activity of a *limulus*-derived Pro-CE, and (c) an RNA fragment produced through transcription of the DNA fragment (a) or (b).

The present invention also provides a virus harboring the nucleic acid fragment of the present invention (hereinafter referred to as a "virus of the present invention").

The "virus" employed in the invention is preferably a baculovirus. Among baculoviruses, NPV is preferred, with AcNPV being more preferred.

The present invention also provides a cell harboring the virus of the present invention (hereinafter referred to as a "cell of the present invention").

No particular limitation is imposed on the "cell," and the cell is freely selected in consideration of, for example, matching with the virus of the present invention. Examples of the cell include cells derived from *E. coli*, bacteria, yeasts, and insects. As mentioned above, the virus of the present invention is preferably a baculovirus. When a baculovirus is employed, an insect-derived cell is preferably selected.

The present invention also provides a method of producing a *limulus*-derived Pro-CE, the method comprising the steps of growing the cell of the present invention, and preparing a *limulus*-derived Pro-CE from the growth product (hereinafter referred to as a "production method of the present invention").

The present invention also provides a *limulus*-derived Pro-CE produced through the production method of the present invention (hereinafter referred to as an "enzyme of the present invention").

The present invention also provides a method of detecting Et, wherein the method comprises:

causing "a serine protease precursor which expresses an activity of converting Pro-CE to CE upon contact with Et" to be co-present with the enzyme of the present invention in a test sample in which the Et possibly present therein is to be detected (hereinafter may be referred to as an "Et-detection sample"); and detecting Et present in the sample through employing, as an index, enzymatic activity in conversion of Pro-CE to CE (hereinafter referred to as a "method 1 of the present invention").

In the method 1 of the present invention, the "serine protease precursor which expresses an activity of converting Pro-CE to CE upon contact with the Et" preferably comprises a "serine protease precursor which expresses an activity of converting Pro-CE to CE upon contact with activated factor C", and "*limulus*-derived factor C and/or recombinant factor C."

The "serine protease precursor which expresses an activity of converting Pro-CE to CE upon contact with activated factor C" is preferably *limulus*-derived factor B and/or recombinant factor B.

The aforementioned factors C and B are preferably recombinants. In one best mode of the method 1 of the present invention, the enzyme of the present invention is caused to be co-present with factors C and B in an Et-detection test sample, and the employed factors C and B are recombinants. Carrying out the method 1 of the present invention by use of *limulus*-derived native factors C and B are considerably preferred from the viewpoint of effectiveness of method, such as detection sensitivity. However, in order to collect the hemolymph of horseshoe crab serving as a raw material for native factors C and B, horseshoe crabs must be captured, and their blood must be collected in such an amount that continual growth thereof is not impaired. In addition, a certain level of stress is unavoidably imposed on horseshoe crabs upon capturing and blood collection, and some people point out a decrease in the number of horseshoe crabs caused by environmental destruction, etc. Thus, it is deeply significant that recombinant proteins are employed as all proteins involved in cascade reaction for carrying out the method 1 of the present invention, particularly from the viewpoint of protection of precious biological resources. Use of recombinant proteins greatly contributes to the protection of lifeforms and provision of animal alternatives.

In the case where recombinant factors C and B are employed as essential elements of the Et-detection system, no particular limitation is imposed on the selection of a vector into which a gene encoding the corresponding factor is introduced and on the host to which the vector is transduced. However, similar to the case of the aforementioned recombinant Pro-CE, the virus serving as a vector is preferably a baculovirus. Among baculoviruses, NPV is preferred, with AcNPV being more preferred. Examples of the host include cells derived from *E. coli*, bacteria, yeasts, and insects. As mentioned above, the virus of the present invention is preferably a baculovirus. When a baculovirus is employed, an insect-derived cell is preferably selected.

The concept "employing, as an index, an enzymatic activity in conversion of the enzyme of the present invention to CE" means that the enzymatic activity induced through conversion of Pro-CE (the enzyme of the present invention) to CE is detected quantitatively or qualitatively, whereby the detected enzymatic activity is employed as an index for the amount or presence of Et in the test sample. Examples of the "phenomenon that exhibits enzymatic activity induced through conversion of Pro-CE to CE" include coagulation of horseshoe crab amebocyte lysate through formation of coaguline gel in the presence of CE (which can be detected through observation of gelation, change in turbidity, etc.) and developing color following amide bond cleavage of a synthetic chromogenic substrate. Particularly when the synthetic chromogenic substrate is employed, an assay system of high sensitivity and good reproducibility can be established. Such an assay system, which does not necessarily employ a *limulus*-derived lysate, is very advantageous from the viewpoint of protection of precious biological resources.

Examples of the synthetic chromogenic substrate include X-A-Y (wherein X represents a protective group, Y represents a coloring dye, and A represents a tripeptide). The A—Y bond is cleaved in the presence of CE, to thereby cause the coloring dye Y to develop color, which serves as an index for quantitatively or qualitatively detect an Et. Examples of the protective group X include known peptide protective groups such as a t-butoxycarbonyl group and a benzoyl group.

Examples of the coloring dye Y include pNA, MCA (7-methoxycoumarin-4-acetic acid), DNP (2,4-dinitroaniline), and Dansyl dye. Examples of the tripeptide include Leu-Gly-Arg (LGR), Ile-Glu-Gly-Arg (IEGR), and Val-Pro-Arg (VPR).

For quantitatively carrying out the method 1 of the present invention, a correlation (typically a calibration curve) between the Et levels determined by use of a standard Et and the corresponding index intensities (absorbance (optical density) for coloring dye Y, turbidity attributed to coagulation of lysate, etc.) is established in advance. The Et level of a test sample can be quantitatively determined from an actually detected index intensity on the basis of the established correlation.

No particular limitation is imposed on the test sample, and examples of the sample include injection water, pharmaceuticals, infusions, blood preparations, medical apparatus (medical tools), quasi-drugs, cosmetics, foods, beverages, environmental samples (air, river water, soil, etc.), native proteins, genetically modified proteins, nucleic acids, enzymes, saccharides, electrolytes, and bio-samples (blood, body fluid, tissue, etc.).

The present invention also provides an Et-detection kit for carrying out the method 1 of the present invention (hereinafter referred to as a "kit 1 of the present invention"), wherein the kit comprises, as essential components, the enzyme of the present invention and a "serine protease precursor which expresses an activity of converting Pro-CE to CE upon contact with Et."

In the kit 1 of the present invention, the "serine protease precursor which expresses an activity of converting Pro-CE to CE upon contact with Et" is preferably a "serine protease precursor which expresses an activity of converting Pro-CE to CE upon contact with activated factor C", and "*limulus*-derived factor C and/or recombinant factor C."

The "serine protease precursor which expresses an activity of converting Pro-CE to CE upon contact with activated factor C" is preferably *limulus*-derived factor B and/or recombinant factor B.

In the kit 1 of the present invention, the aforementioned factors C and B are preferably recombinants. In one best mode of the kit 1 of the present invention, the employed factors C and B are recombinants. In other words, the proteins contained in the kit 1 of the present invention and involved in cascade reaction more preferably include only the enzyme of the present invention and recombinant factors C and B.

The kit 1 of the present invention may also include reagents for carrying out the method 1 of the present invention; e.g., the aforementioned synthetic chromogenic substrate (X-A-Y), buffer, diluent, salt, and *limulus*-derived amebocyte lysate, selected in accordance with the mode of the method 1 of the present invention employing the kit 1 of the present invention.

The present invention also provides a method of detecting BG, wherein the method comprises:

causing a "serine protease precursor which expresses an activity of converting Pro-CE to CE upon contact with BG" to be co-present with the enzyme of the present invention in a test sample in which BG possibly present therein is to be detected (hereinafter may be referred to as a "BG-detection sample"); and detecting BG present in the sample through employing, as an index, enzymatic activity in conversion of Pro-CE to CE (hereinafter the method referred to as a "method 2 of the present invention").

In the method 2 of the present invention, the "serine protease precursor which expresses an activity of converting Pro-CE to CE upon contact with BG" is preferably *limulus*-derived factor G and/or recombinant factor G.

The aforementioned factor G is preferably recombinant. In one best mode of the method 2 of the present invention, the enzyme of the present invention is caused to be co-present with factor G in a BG-detection sample, and the factor G is recombinant.

The reason why recombinant factor G is preferred in the method 2 of the present invention is the same as mentioned in relation to that recombinant factors C and B are preferred in the method 1 of the present invention. For producing recombinant factor G, the virus serving as a vector is preferably a baculovirus. Among baculoviruses, NPV is preferred, with AcNPV being more preferred. This feature is the same as described in relation to factors C and B. Examples of the host include cells derived from *E. coli*, bacteria, yeasts, and insects. As mentioned above, the virus of the present invention is preferably a baculovirus. When a baculovirus is employed, an insect-derived cell is preferably selected. This feature is also the same as described in relation to factors C and B.

Similar to the method 1 of the present invention, the concept "employing, as an index, an enzymatic activity in conversion of the enzyme of the present invention to CE" means that the phenomenon of conversion of Pro-CE (the enzyme of the present invention) to CE is quantitatively or qualitatively detected, whereby the detected enzymatic activity is employed as an index for the amount or presence of BG in the test sample. Examples of the phenomenon that exhibits enzymatic activity induced through conversion of Pro-CE to CE are the same as disclosed in relation to the method 1 of the present invention. The synthetic coloring substrate (X-A-Y) may also be employed in the method 2 of the present invention.

For quantitatively carrying out the method 2 of the present invention, a correlation (typically a calibration curve) between the BG levels determined by use of standard BG and the corresponding index intensities (absorbance (optical density) for coloring dye Y, turbidity attributed to coagulation of lysate, etc.) is established in advance. The BG level of a test sample can be quantitatively determined from an actually detected index intensity on the basis of the established correlation.

No particular limitation is imposed on the test sample, and examples of the sample include injection water, pharmaceuticals, infusions, blood preparations, medical apparatus (medical tools), quasi-drugs, cosmetics, foods, beverages, environmental samples (air, river water, soil, etc.), native proteins, genetically modified proteins, nucleic acids, enzymes, saccharides, electrolytes, and bio-samples (blood, body fluid, tissue, etc.).

The present invention also provides a BG-detection kit for carrying out the method 2 of the present invention (hereinafter referred to as a "kit 2 of the present invention"), wherein the kit comprises, as essential components, the enzyme of the present invention and a "serine protease precursor which expresses an activity of converting Pro-CE to CE upon contact with BG."

In the kit 2 of the present invention, the "serine protease precursor which expresses an activity of converting Pro-CE to CE upon contact with BG" is preferably *limulus*-derived factor G and/or recombinant factor G.

In the kit 2 of the present invention, the aforementioned factor G is preferably a recombinant. In one best mode of the kit 2 of the present invention, the employed recombinant factor G includes entire factor G molecular components (α- and β-subunits). In other words, the proteins contained in the kit 2 of the present invention and involved in cascade reaction preferably include exclusively the enzyme of the present invention and recombinant factor G.

The kit 2 of the present invention may also include reagents for carrying out the method 2 of the present invention; e.g., the aforementioned synthetic chromogenic substrate (X-A-Y), buffer, diluent, salt, and *limulus*-derived lysate, selected in accordance with the mode of the method 2 of the present invention employing the kit 2 of the present invention.

Effects of the Invention

The nucleic acid fragment of the present invention is very useful, since the virus of the present invention, which is useful for steady, low-cost, and large-scale production of Pro-CE of satisfactory quality, can be provided through employment of the nucleic acid fragment. The virus of the present invention is very useful, since the cell of the present invention, which is useful for steady, low-cost, and large-scale production of Pro-CE of satisfactory quality, can be provided through employment of the virus. The cell of the present invention is very useful, since the cell can produce a protein maintaining Pro-CE activity and satisfactory quality, steadily, at low cost, and on a large scale and can also provide the method and kit of the present invention. The method and kit of the present invention realize detection and measurement of Et and BG without preparing a lysate from horseshoe crabs, which are precious bio-resources, and can provide a very useful technique in terms of protection of lifeforms, provision of animal alternatives, cost, precision, reproducibility, etc.

BRIEF DESCRIPTION OF THE DRAWINGS

FIG. 1 depicts the results of sequence analysis of the target sequence of a recombinant baculovirus into which a DNA sequence encoding Pro-CE is inserted. The upper column shows the region of the inserted DNA that was analyzed, and the lower columns show the nucleotide sequences of the N-terminus (SEQ ID NO: 21) and C-terminus (SEQ ID NO: 22) regions of the inserted target sequence obtained by the analysis.

DETAILED DESCRIPTION OF THE INVENTION

Figure 2:
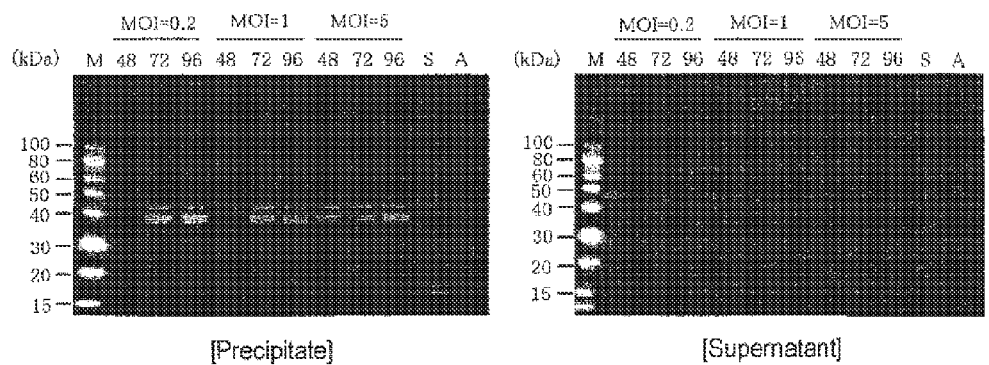
FIG. 2 depicts results of western blotting to detect Pro-CE expressed products. Lane M represents a molecular weight marker; Lanes 48, 72, and 96 represent a 48-hour-infection-lane, a 72-hour-infection-lane, and a 96-hour-infection-lane, respectively; Lane S represents a non-virus-infected lane, and Lane A represents a wild-type-virus-infected lane.

Best modes for carrying out the present invention will next be described.

<1> The Nucleic Acid Fragment of the Present Invention

The nucleic acid fragment of the present invention is a nucleic acid fragment encoding a *limulus*-derived Pro-CE. No particular limitation is imposed on the "nucleic acid fragment encoding a *limulus*-derived Pro-CE" (i.e., the nucleic acid fragment of the present invention), so long as the nucleic acid fragment encodes a *limulus*-derived Pro-CE. For example, the nucleic acid fragment may be a nucleic acid fragment having a nucleotide sequence defined by SEQ ID NO: 1 (SEQ ID NO: 2 shows only the amino acid sequence corresponding to the nucleotide sequence). It will be readily appreciated by those skilled in the art that the nucleic acid fragment of the present invention also encompasses nucleic acid fragments having different nucleotide sequences attributed to degeneration of genetic codes.

The "nucleic acid fragment" employed in the present invention may be a DNA fragment or an RNA fragment, which may be selected by those skilled in the art in consideration of the use of the nucleic acid fragment. For example, when stability is emphasized, a DNA fragment may be selected.

The nucleic acid fragment of the present invention may be, for example, a nucleic acid fragment encoding Pro-CE derived from any of the following horseshoe crabs: *Tachypleus tridentatus, Limulus polyphemus, Tachypleus gigas*, and *Tachypleus rotundicauda*.

Of these, a nucleic acid fragment encoding Pro-CE derived from *Tachypleus tridentatus* or *Limulus polyphemus* is preferred, with a nucleic acid fragment encoding Pro-CE derived from *Tachypleus tridentatus* being more preferred.

The nucleic acid fragment of the present invention may be chemically synthesized or may be produced through a genetic engineering technique. For production through a genetic engineering technique, for example, by use of an artificially prepared primer having a nucleotide sequence defined by SEQ ID NO: 5 or 6, a target DNA fragment is amplified, through PCR technique, from a cDNA library prepared through a customary method from hemocytes (amebocytes) of a horseshoe crab such as *Limulus polyphemus, Tachypleus tridentatus, Tachypleus gigas*, or *Tachypleus rotundicauda*. The resultant PCR product may be readily isolated through molecular-weight-based separation means (e.g., gel electrophoresis).

In the present invention, the "nucleic acid fragment encoding *limulus*-derived Pro-CE" is more preferably any of the following nucleic acid fragments (A) to (C):

(A) a DNA fragment encoding a protein having the amino acid sequence defined by SEQ ID NO: 4, (B) a DNA fragment encoding a "protein having an amino acid sequence defined by SEQ ID NO: 4 in which one or several amino acid residues are deleted, substituted, inserted, or translocated, and having activity of a *limulus*-derived Pro-CE," and (C) an RNA fragment obtained through transcription of the aforementioned DNA fragment (A) or (B).

As used herein, the "DNA fragment encoding a protein having an amino acid sequence defined by SEQ ID NO: 4" is a DNA fragment encoding a Pro-CE derived from *Tachypleus tridentatus*.

A naturally occurring protein may include a mutation in the amino acid sequence (e.g., substitution, deletion, insertion, or translocation of amino acid residues) caused by the polymorphism or mutation of the DNA fragment encoding the protein. Meanwhile, a produced protein may include a post-translational modification (e.g., phosphorylation, glycosylation, or lipidation of amino acid residues, or hydroxylation of proline) caused by intracellular modification during purification. Although having such a mutation, some proteins are known to exhibit physiological and biological activities substantially the same as those of the protein having none of the aforementioned mutations. Thus, the "protein encoded by the DNA fragment (B)," which slightly differs from the "protein encoded by the DNA fragment (A)" in structure but has no great difference in function, can be regarded as substantially equivalent to the "protein encoded by the DNA fragment (A)." A similar logic is also applied to the case where the aforementioned mutations are intentionally introduced into an amino acid sequence of protein. In this case, a wider range of variants can be prepared. For example, as has been known, a polypeptide engineered from human interleukin 2 (IL-2) so that a certain cysteine residue in the amino acid sequence of IL-2 is substituted by serine maintains human interleukin 2 activity (Science, 224, 1431 (1984)). Such a "mutated protein" may be prepared through a known technique; for example, "site-specific mutagenesis." Also, a certain protein is known to have a peptide region that is not essential in terms of activity. Examples of such a protein include a signal peptide present in an extracellularly secreted protein, and a prosequence observed in a protease precursor or a similar substance. Most of these peptide regions are removed after translation or during conversion to the corresponding activated proteins. Although such proteins have a primary structure different from that of the "protein encoded by the DNA fragment (A)," the proteins have a function substantially the same as that of the "protein encoded by the DNA fragment (A)." Therefore, the "protein encoded by the DNA fragment (B)" represents these proteins.

As used herein, the term "several amino acid residues" refers to amino acid residues which are allowed to have mutations without impairing the protein activity. For example, when a protein includes 600 amino acid residues, the number of such amino acid residues is about 2 to about 30, preferably 2 to 15, more preferably 2 to 8.

The protein encoded by the DNA fragment (B) has an activity of *limulus*-derived Pro-CE. Activity of Pro-CE may be determined by causing Pro-CE to be co-present with a synthetic substrate (e.g., t-butoxycarbonyl-leucyl-glycyl-arginine-pNA (Boc-Leu-Gly-Arg-pNA)), Et, factor C, and factor B, and examining the reactivity of Pro-CE. Specifically, when Pro-CE has activity, pNA is released by causing Pro-CE to be co-present with the synthetic substrate, Et, and factor C. The amount of thus-produced pNA can be determined through measurement of absorbance. A specific determination method will be described in Example 2.

In the present invention, no particular limitation is imposed on the state of "co-presence," so long as co-present elements are freely allowed to be in contact with one another. Specifically, the state of "co-presence" refers to the state where Pro-CE, a synthetic substrate, Et, factor C, and factor B are freely allowed to be in contact with one another, or the state where Pro-CE, a synthetic substrate, BG, and factor G are freely allowed to be in contact with one another.

As used herein, the term "reaction" refers to a reaction in which the Pro-CE is converted into CE by causing Pro-CE to be co-present with the synthetic substrate, and CE acts on the synthetic substrate, to thereby hydrolyze the amino bonds thereof, whereby pNA is released.

The DNA fragment (A) encoding a "protein having an amino acid sequence defined by SEQ ID NO: 4" may be, for example, a DNA fragment having a nucleotide sequence of nucleotides 1 to 1,143 in SEQ ID NO: 3. Alternatively, a DNA fragment deposited in GenBank with an accession No. D161657 may also be employed.

The DNA fragment (B) encoding a "protein having an amino acid sequence defined by SEQ ID NO: 4 in which one or several amino acid residues are deleted, substituted, inserted, or translocated, and having activity of *limulus*-derived Pro-CE" may be, for example, the aforementioned DNA fragment (A), a DNA fragment complementary thereto, or a DNA fragment which hybridizes with any of these DNA fragments under stringent conditions.

As used herein, the term "stringent conditions" refers to conditions which allow formation of a so-called specific hybrid but do not allow formation of a non-specific hybrid (see, for example, Sambrook, J., et al., Molecular Cloning A Laboratory Manual, Second Edition, Cold Spring Harbor Laboratory Press (1989)). Specific examples of the "stringent conditions" include performing hybridization at 42° C. in a solution containing 50% formamide, 4×SSC, 50 mM HEPES (pH 7.0), 10×Denhardt's solution, and 100 μg/mL salmon sperm DNA, and washing at room temperature with 2×SSC and a 0.1% SDS solution and at 50° C. with 0.1×SSC and a 0.1% SDS solution.

Preferably, the nucleic acid fragment of the present invention is further linked to a DNA fragment encoding, for example, a marker peptide. Examples of the marker peptide include protein A, an insulin signal sequence, His-tag, FLAG, CBP (calmodulin-binding protein), and GST (glutathione S-transferase). The nucleic acid fragment of the present invention also encompasses an RNA fragment obtained through transcription of the aforementioned DNA fragment (A) or (B).

The nucleic acid fragment of the present invention may be employed for production of "the virus of the present invention" described hereinbelow, and thus for production of, for example, the cell of the present invention.

<2> The Virus of the Present Invention

The virus of the present invention harbors the nucleic acid fragment of the present invention.

The nucleic acid fragment of the present invention is the same as mentioned above.

The state "harboring a nucleic acid fragment" in the virus of the present invention does not exclude the state in which the virus harbors other nucleotides or nucleic acid fragments, so long as the relevant nucleic acid fragment is harbored. Thus, in addition to the relevant nucleic acid fragment, for example, other nucleic acid fragments encoding a marker peptide or a similar peptide may be harbored.

For example, the virus of the present invention also encompasses a vector harboring a linked DNA fragment formed of "the aforementioned DNA fragment (A) or (B) (i.e., the nucleic acid fragment of the present invention)" and a "DNA fragment encoding, for example, a marker peptide." When the nucleic acid fragment harbored is designed in the above manner, a protein fused with, for example, a marker peptide may be expressed. The thus-expressed protein is advantageous in that the purification, detection, analysis, etc. thereof can be facilitated. Examples of the marker peptide include protein A, an insulin signal sequence, His-tag, FLAG, CBP (calmodulin-binding protein), and GST (glutathione S-transferase). For example, a protein fused with protein A may be purified in a simple manner through affinity chromatography employing an IgG-bound solid phase. Similarly, a His-tag-fused protein may be purified with a magnetic nickel-bound solid phase, whereas a FLAG-fused protein may be purified with an anti-FLAG antibody-bound solid phase. Since a protein fused with an insulin signal sequence is extracellularly secreted (e.g., secreted in a culture medium), an extraction process including crushing of cells may be eliminated.

No particular limitation is imposed on the production method for the virus of the present invention. One exemplary method for producing the virus of the present invention will be described as follows. More specific procedure thereof will be described in the Examples.

Firstly, a nucleic acid fragment encoding *limulus*-derived Pro-CE is provided. In the case where the aforementioned DNA fragment (A) is employed as the nucleic acid fragment, a DNA fragment encoding a "protein having an amino acid sequence defined by SEQ ID NO: 4" is provided. In the case where the aforementioned DNA fragment (B) is employed as the nucleic acid fragment, there is provided a DNA fragment encoding a "protein having an amino acid sequence defined by SEQ ID NO: 4 in which one or several amino acid residues are deleted, substituted, inserted, or translocate (transposed), and having an activity of *limulus*-derived Pro-CE." No particular limitation is imposed on the type of the DNA fragment employed, so long as the DNA fragment encodes the corresponding protein. The DNA fragment includes those having a variety of nucleotide sequences attributed to degeneration of genetic codes. However, any of these DNA fragments having a specific nucleotide sequence may be employed.

The virus of the present invention can be produced through introduction of such a nucleic acid fragment into a virus.

No particular limitation is imposed on the virus into which such a nucleic acid fragment is introduced, so long as the virus can be employed for gene transfection. Particularly, a baculovirus (in particular, an NPV) is preferably employed. No particular limitation is imposed on the species of the NPV employed, so long as the NPV is a virus belonging to NPVs. For example, AcNPV or *Bombyx mori* NPV (BmNPV) may be employed. Of these, AcNPV is preferred.

Introduction of a nucleic acid fragment into a virus may be carried out through homologous recombination by use of a transfer vector. No particular limitation is imposed on the type of the transfer vector employed. For example, pPSC8 (Protein Science), pFastBac (Invitrogen), or pVL1393 (Pharmingen) may be employed. Of these, pPSC8 is preferred. These transfer vectors may be commercially available ones.

No particular limitation is imposed on the method of homologous recombination by use of a transfer vector. A specific example thereof will be described in the Examples.

Whether or not the produced virus harbors the aforementioned DNA fragment (A) or (B) may be determined by, for example, any of the following procedures: checking that the produced virus harbors a DNA fragment encoding a *limulus*-derived Pro-CE through analysis of the nucleotide sequence of the virus; checking that a protein expressed by the produced virus has the amino acid sequence of *limulus*-derived Pro-CE; and checking that a protein expressed by the produced virus has a Pro-CE activity.

The virus of the present invention may be employed for production of "the cell of the present invention" described below, and thus employed, for example, in the method of the present invention.

<3> The Cell of the Present Invention

The cell of the present invention harbors the virus of the present invention.

"The virus of the present invention" is the same as mentioned above.

No particular limitation is imposed on the "cell" employed in the present invention, so long as the cell allows infection with the virus of the present invention, and can express the nucleic acid fragment encoding a *limulus*-derived Pro-CE that is harbored by the virus of the present invention. Examples of the cell include insect-derived cells. Specific examples of the insect-derived cells include an Sf9 cell.

No particular limitation is imposed on the method for causing the cell to harbor the virus of the present invention. For example, when the virus of the present invention is a NPV, the cell can be infected with the virus only by bringing the cell into contact with the virus, whereby the cell can harbor the virus. A specific method therefor will be described in the Examples hereinbelow.

Since the cell of the present invention can produce a *limulus*-derived Pro-CE, the cell of the present invention may be selected on the basis of the production performance as an index.

The cell of the present invention may be employed in, for example, the below-described production method of the present invention.

<4> The Production Method of the Present Invention

The production method of the present invention for producing *limulus*-derived Pro-CE includes at least the steps of growing the cell of the present invention, and preparing *limulus*-derived Pro-CE from the growth product.

"The cell of the present invention" is the same as mentioned above.

As used herein, the term "grow" refers to a concept including proliferation of cells which are transformants and growing an organism (e.g., animal or insect) into which transformant cells have been incorporated. As used herein, the term "growth product" is a concept including, for example, a culture medium (supernatant of the culture liquid) after completion of growth of transformants, cultured cells themselves, and matter secreted or discharged from an organism (e.g., animal or insect) into which the cells have been incorporated.

No particular limitation is imposed on the growth conditions (e.g., culture medium and culture conditions), so long as the cell of the present invention can grow and produce *limu-*

*lus*-derived Pro-CE. The growth conditions may be appropriately determined in consideration of, for example, the type of a vector or cell employed. For example, culturing may be carried out at a temperature of about 20 to about 40° C.

The growth period of the cell of the present invention may also be appropriately regulated in consideration of, for example, the amount of the cell of the present invention employed, the amount of a desired Pro-CE produced, or other growth conditions.

Those skilled in the art may appropriately select the method for preparing a *limulus*-derived Pro-CE from the growth product from generally employed methods in consideration of the type of the growth product.

For example, in the case where Pro-CE is produced in a soluble form secreted into a culture medium (culture supernatant), the culture medium is collected and may be employed as is. In the case where Pro-CE is produced in a soluble form secreted in cytoplasm, or produced in an insoluble (membrane-bound) form, the Pro-CE may be extracted through, for example, any of the following treatments: extraction with cell crushing such as a method employing a nitrogen cavitation apparatus, homogenizing, glass beads milling, sonication, the hypotonic extraction, or freeze-thawing; extraction with a surfactant; or a combination thereof. The resultant extract may be employed, as is, as the Pro-CE.

The production method of the present invention may further include other steps, so long as the method includes at least a "step of growing the cell of the present invention, and preparing *limulus*-derived Pro-CE from the growth product." For example, the method may further include the step of purifying the thus-prepared Pro-CE. The purification may be incomplete (partial) purification or complete purification, and may be appropriately selected in consideration of, for example, the use purpose of the Pro-CE.

Specific examples of the purification method include salting out by the mediation of a salt such as ammonium sulfate or sodium sulfate, centrifugation, dialysis, ultrafiltration, adsorption chromatography, ion-exchange chromatography, hydrophobic chromatography, reversed-phase chromatography, gel filtration, gel permeation chromatography, affinity chromatography, electrophoresis, and combinations thereof.

Whether or not, for example, the thus-produced protein is formed of Pro-CE, or the protein maintains an activity of *limulus*-derived Pro-CE may be determined through analysis of the collected protein, in terms of, for example, amino acid sequence, molecular weight, electrophoresis features, or Western blotting employing an antibody reacting specifically to the Pro-CE.

The method of the present invention realizes very effective production of a protein which maintains Pro-CE activity.

<5> The Enzyme of the Present Invention

The enzyme of the present invention is Pro-CE produced through the production method of the present invention.

"The production method of the present invention" is the same as mentioned above.

The enzyme of the present invention may be employed in, for example, the method 1 of the present invention described below.

<6> The Method 1 of the Present Invention

The method 1 of the present invention is a method for sensitively detecting Et. A characteristic feature of the method 1 of the present invention resides in that the enzyme of the present invention is caused to be co-present with a "serine protease precursor which expresses an activity of converting Pro-CE to CE upon contact with Et" in an Et-detection sample, and the Et present in the sample is detected by employing, as an index, enzymatic activity in conversion of the enzyme of the present invention to CE.

"The enzyme of the present invention" is the same as mentioned above.

In the present invention, no particular limitation is imposed on the state of "co-presence," so long as co-present elements are allowed to be in contact with one another.

For example, no particular limitation is imposed on the state of "co-presence," so long as the enzyme of the present invention, an Et-detection sample, and a "serine protease precursor which expresses an activity of converting Pro-CE to CE upon contact with Et" are allowed to be in contact with one another. These elements may be caused to be co-present with one another in a solution. Alternatively, Pro-CE or a "serine protease precursor which expresses an activity of converting Pro-CE to CE upon contact with Et" may be immobilized on a solid phase, and thus-immobilized Pro-CE or serine protease precursor may be respectively brought into contact with a "serine protease precursor which expresses an activity of converting Pro-CE to CE upon contact with Et" or Pro-CE.

In the method 1 of the present invention, preferably, the "serine protease precursor which expresses an activity of converting Pro-CE to CE upon contact with Et" is a "serine protease precursor which expresses an activity of converting Pro-CE to CE upon contact with activated factor C", and "*limulus*-derived factor C and/or recombinant factor C."

The "serine protease precursor which expresses an activity of converting Pro-CE to CE upon contact with activated factor C" is preferably *limulus*-derived factor B and/or recombinant factor B.

No particular limitation is imposed on the "factor C" or "factor B" employed in the method 1 of the present invention, so long as the factor maintains its function. For example, the factor C or B employed may be naturally occurring factor C or B fraction prepared through purification (e.g., chromatography) of amebocyte lysate derived from any of the four horseshoe crabs: *Tachypleus tridentatus, Limulus polyphemus, Tachypleus gigas*, and *Tachypleus rotundicauda*. Alternatively, the factor C or B employed may be recombinant factor C or B. The naturally occurring factor C or B fraction may be prepared through treatment of the aforementioned lysate with, for example, a carrier to which dextran sulfate, a sulfopropyl group, or the like is bound, or a specific adsorption carrier. The recombinant factor C may be appropriately prepared, for example, on the basis of the known amino acid sequence of naturally occurring factor C derived from *Tachypleus tridentatus* or *Tachypleus rotundicauda*. No particular limitation is imposed on the method for preparing the recombinant factor C. For example, the recombinant factor C may be prepared through the following procedure: a target nucleotide sequence for factor C having a His-tag at the C terminus is synthesized and introduced into a transfer vector (e.g., pPSC8, product of Takara Bio Inc.); Sf9 cells are co-transfected with the resultant expression vector (Factor C/pPSC8) DNA fragment and a baculovirus (AcNPV) DNA fragment; and the virus fluid obtained from the resultant culture supernatant is purified, followed by amplification. The recombinant factor B may also be prepared in a manner similar to that described above. The amino acid sequence of factor C or factor B and the gene coding therefor have already been known. Factor C is commercially available, and the commercial product will be described in the Examples hereinbelow. The nucleotide sequence of the gene for factor B is shown in SEQ ID NO: 15, and the amino acid sequence of factor B is shown in SEQ ID NO: 16. The recombinant of such a factor may be produced on the basis of the corresponding sequence data through a process substantially the same as that for the aforementioned enzyme of the present invention. It will be readily appreciated by those skilled in the art that a protein produced on the basis of a nucleotide sequence which, as a result of degeneration of genetic codes, differs from the known nucleotide sequence of factor C or the nucleotide sequence defined by SEQ ID NO: 15 may be employed in the present invention as factor C or B, so long as the protein has an effect intrinsic to factor C or B.

Operation of the reconstruction system does not require provision of insect cells as a reaction site. For facilitation of at least triggering of cascade reaction, sequential activation of serine protease precursors, and reaction of CE in a cell-free system, preferably, conditions for the operation include, for example, constant heating and co-presence of ions of a metal such as an alkaline earth metal (e.g., calcium, strontium, barium, beryllium, or magnesium) or an alkali metal (e.g., lithium, sodium, or potassium).

In the method 1 of the present invention, more preferably, the enzyme of the present invention, recombinant factor C, and recombinant factor B are exclusively caused to be co-present as cascade reaction proteins.

As used herein, the term "cascade reaction" refers to the following reaction "1." and/or reaction "2.":

1. a series of reactions in which factor C (Et-sensitive factor, molecular weight: 123,000) present in amebocyte lysate is activated through addition of Et to the lysate, to thereby form activated factor C; the activated factor C hydrolyzes a specific site of factor B (molecular weight: 64,000) to thereby form activated factor B; the activated factor B activates Pro-CE (molecular weight: 54,000) to thereby convert it into CE; and the CE hydrolyzes specific sites in a loop cross-linked by disulfide bonds of coagulogen (coagulated protein, molecular weight: 19,723); i.e., hydrolyzes the bond between $Arg^{18}$ and $Thr^{19}$ and the bond between $Arg^{46}$ and $Gly^{47}$, to thereby release peptide C (28 amino acid residues) represented by $H-Thr^{19} \ldots Arg^{46}-OH$ and to convert the remaining portion into coagulin gel; and 2. a series of reactions in which factor G (BG-sensitive factor) present in amebocyte lysate is activated through addition of BG to the lysate; the activated factor G activates Pro-CE to thereby convert it into CE; and the CE hydrolyzes specific sites in a loop cross-linked by disulfide bonds of coagulogen, to thereby form coagulin gel.

The term "cascade reaction protein" refers to a protein involved in "cascade reaction"; i.e., a serine protease precursor (factor C, factor B, factor G, or Pro-CE). Specifically, the cascade reaction proteins in the aforementioned cascade reaction "1." are factor C, factor B, and Pro-CE, and the cascade reaction proteins in the cascade reaction "2." are factor G and Pro-CE.

As shown in the Examples hereinbelow, the origins of the genetically engineered coagulation factors employed in the method 1 of the present invention may be different from one another. For example, the Et detection method may include the step of causing the enzyme of the present invention to be co-present with factor C derived from *Tachypleus rotundicauda* and factor B derived from *Limulus polyphemus*.

The method 1 of the present invention can be readily carried out by means of the below-described kit 1 of the present invention.

<7> The Kit 1 of the Present Invention

The kit 1 of the present invention is an Et detection kit for carrying out the method 1 of the present invention. A characteristic feature of the kit 1 of the present invention resides in that the kit includes at least the enzyme of the present invention and a "serine protease precursor which expresses an activity of converting Pro-CE to CE upon contact with Et."

"The enzyme of the present invention" is the same as mentioned above.

The "serine protease precursor which expresses an activity of converting Pro-CE to CE upon contact with activated factor C" is preferably *limulus*-derived factor B and/or recombinant factor B.

Preferably, the kit 1 of the present invention includes, as cascade reaction proteins, exclusively the enzyme of the present invention, recombinant factor C, and recombinant factor B.

Those skilled in the art may appropriately employ the kit 1 of the present invention on the basis of the method 1 of the present invention.

The terms used in the kit 1 of the present invention such as "factor C," "factor B," and "cascade reaction" have the same meanings as defined above in the method 1 of the present invention. As described above, reagents, etc. employed for carrying out the method 1 of the present invention (e.g., the aforementioned synthetic chromogenic substrate (X-A-Y), buffer, diluent, salt, and *limulus*-derived amebocyte lysate) may be included in the kit 1 of the present invention, which may be selected in consideration of the mode of the method 1 of the present invention performed by means of the kit.

<8> The Method 2 of the Present Invention

The method 2 of the present invention is a method for detecting BG. A characteristic feature of the method 2 of the present invention resides in that the enzyme of the present invention is caused to be co-present with a "serine protease precursor which expresses an activity of converting pro-clotting enzyme to clotting enzyme upon contact with BG" in a BG-detection sample, and BG present in the sample is detected by employing, as an index, enzymatic activity induced through conversion of the enzyme of the present invention to clotting enzyme.

"The enzyme of the present invention" is the same as mentioned above.

In the method 2 of the present invention, preferably, the "serine protease precursor which expresses an activity of converting Pro-CE to CE upon contact with BG" is *limulus*-derived factor G and/or recombinant factor G.

No particular limitation is imposed on the "factor G" employed in the method 2 of the present invention, so long as the factor maintains its function. For example, the factor G employed may be a naturally occurring factor G fraction prepared through purification (e.g., chromatography) of amebocyte lysate derived from any of the aforementioned four horseshoe crabs. Alternatively, the factor G employed may be recombinant factor G. Recombinant factor G is a protein formed of subunits α and β, and the respective subunits may be produced through the following procedures.

Firstly, a DNA fragment encoding subunit α of *limulus*-derived factor G is provided. The DNA fragment may be, for example, a DNA fragment deposited in GenBank with an accession No. 16622 (SEQ ID NO: 17, the amino acid sequence corresponding to the DNA fragment is shown in SEQ ID NO: 18). The DNA fragment is treated with BamHI/Hind III, and DNA fragments having a target gene sequence are collected. The sample is blunt-ended and then ligated through mixing with Nru I-treated pPSC8 (transfer vector). Subsequently, *E. coli* JM109 is transformed with the ligation product, to thereby yield a transformant. Plasmid in which fragments having a target size have been determined is purified. Sf9 cells are co-transfected with the thus-selected expression vector (Factor G-α/pPSC8) DNA fragment and a baculovirus (AcNPV) DNA fragment. Thereafter, the virus fluid obtained from the resultant culture supernatant is purified, followed by amplification. Then, express SF+ cells are infected with the virus fluid, and the resultant culture liquid is centrifuged, to thereby yield a supernatant fraction and a precipitate fraction. Subunit α of factor G may be prepared from these fractions. Subunit β may be prepared by performing the same procedure as for subunit α, except that the subunit-α-encoding DNA fragment is replaced with a DNA fragment encoding subunit β of *limulus*-derived factor G. The subunit-β-encoding DNA fragment may be, for example, a nucleotide sequence deposited in GenBank with an accession No. 16623 (SEQ ID NO: 19) (the amino acid sequence corresponding thereto is shown in SEQ ID NO: 20). It will be readily appreciated by those skilled in the art that a protein produced on the basis of nucleotide sequences which, as a result of degeneration of genetic codes, differ from the nucleotide sequences of SEQ ID NOs: 16 and 17 may be employed in the present invention as factor G, so long as the protein has an effect intrinsic to factor G.

Operation of the reconstruction system does not require provision of a certain type of cells (e.g., insect cells) as a reaction site. For facilitation of at least triggering of cascade reaction, sequential activation of serine protease precursors, and reaction of CE in a cell-free system, preferably, conditions for the operation include, for example, constant heating and co-presence of ions of a metal such as an alkaline earth metal or an alkali metal.

In the method 2 of the present invention, more preferably, the enzyme of the present invention and recombinant factor G are exclusively caused to be co-present as cascade reaction proteins. Similar to the case of the method 1 of the present invention, the enzyme of the present invention and recombinant factor G may be derived from the same origin or different origins.

The terms used in the method 2 of the present invention such as "co-present," "cascade reaction," and "cascade reaction protein" have the same meanings as defined above in the method 1 of the present invention.

The method 2 of the present invention may be employed in the below-described kit 2 of the present invention.

<9> The Kit 2 of the Present Invention

The kit 2 of the present invention is a BG detection kit for carrying out the method 2 of the present invention. A characteristic feature of the kit 2 of the present invention resides in that the kit includes at least the enzyme of the present invention and a "serine protease precursor which expresses an activity of converting Pro-CE to CE upon contact with BG."

"The enzyme of the present invention" is the same as mentioned above.

In the kit 2 of the present invention, preferably, the "serine protease precursor which expresses an activity of converting Pro-CE to CE upon contact with BG" is *limulus*-derived factor G and/or recombinant factor G.

More preferably, factor G employed in the kit is in a recombinant form. In a most preferred mode of the kit 2 of the present invention, all the factors G molecules included in the kit are in a recombinant form. That is, more preferably, the kit 2 of the present invention includes, as cascade reaction proteins, exclusively the enzyme of the present invention and recombinant factor G.

Those skilled in the art may appropriately employ the kit 2 of the present invention on the basis of the method 2 of the present invention.

The term "factor G" used in the kit 2 of the present invention has the same meaning as described in the method 2 of the present invention. The terms "cascade reaction" and "cascade reaction protein" have the same meanings as defined above in the method 1 of the present invention. As described above, reagents, etc. employed for carrying out the method 2 of the present invention (e.g., the aforementioned synthetic chromogenic substrate (X-A-Y), buffer, diluent, salt, and *limulus*-derived amebocyte lysate) may be included in the kit 2 of the present invention, which may be selected in consideration of the mode of the method 2 of the present invention performed by means of the kit.

EXAMPLES

The present invention will next be described in more detail by way of examples.

Example 1

Expression of Pro-CE by Use of Insect Cells

A cDNA fragment represented by SEQ ID NO: 3 (having a nucleotide sequence of nucleotides 1 to 1125 in SEQ ID NO: 3, a His-Tag sequence being attached to the C-terminus) was kindly offered by Dr. Tatsushi MUTA (Department of Molecular and Cellular Biochemistry, Kyushu University Graduate School of Medical Science; currently, Department of Bio-Science, Tohoku University Graduate School). The cDNA fragment had been prepared through a method disclosed in Non-Patent Document 2. The cDNA fragment was introduced into a transfer vector (pPSC8), and a clone having a predetermined nucleotide sequence was selected. The thus-selected expression vector (PC/pPSC8) DNA fragment and a baculovirus (AcNPV) DNA fragment were co-transfected into Sf9 cells. The virus fluid obtained from the culture supernatant was purified and amplified. The viral DNA fragment was extracted from the cells infected with the baculovirus, and sequenced. Insect cells (expresSF+, registered trademark, product of protein Science) were infected with the thus-obtained virus fluid, and the expression product was analyzed through Western blotting. Details of these steps will next be described.

1. Construction of Expression Vector

PC/pUC118 (20 ng/μg) (1 μL), 2.5 mM dNTP (12 μL), KOD buffer # (15 μL), 25 mM magnesium chloride solution (2 μL), PC-F and PC-R (4 pmol/μL) (each 2.5 μL), KOD DNA polymerase (product of Toyobo) (1 μL), and sterilized pure water (24 μL) were added to a 0.2-mL sample tube under stirring, and the mixture was subjected to PCR. The presence of a target gene in the PCR product was confirmed, and the product was diluted with TE buffer to the total volume of 16 μL. Then, 100 mM ATP (1 μL), 10× Buffer (1 μL), and T4Polynucleotide Kinase (product of Takara Bio) were added to the obtained PCR product, and the mixture was incubated at 37° C. for 30 minutes. The PCR product was purified and subjected to ligation through mixing with Sma I-treated pPSC12. E. coli JM109 was transformed with the ligation product, to thereby form a transformant (PC/pPSC12). PC/pPSC12 was digested with Xba I/Bgl II, and a fragment containing the target gene was recovered. The thus-produced fragment was mixed with pPSC8 which had been treated with the same enzyme, and the resultant mixture was subjected to ligation. E. coli JM109 was transformed with the ligation product, to thereby form a transformant. Plasmids in which fragments of the target size had been confirmed were purified, and sequenced. The sequencing was performed by use of the below-described primers and ABI Prism Big Dye Terminator Cycle Sequencing Kit Ver. 3 (Applied Biosystems). The analysis was performed by means of an automated sequencer ABI Prism 310 Genetic Analyzer (Applied Biosystems).

Sequences of the primers are shown in the following sequence list by SEQ ID NOs: 5 to 10.
SEQ ID NO: 5: PC-F
SEQ ID NO: 6: PC-R
SEQ ID NO: 7: PSC2
SEQ ID NO: 8: PSC4
SEQ ID NO: 9: PC 453/472-F
SEQ ID NO: 10: PC 683/664-R A clone in which insertion of a target gene had been confirmed was inoculated to an LB medium (100 mL) containing 50 μg/mL ampicillin, and cultivated at 30° C. for one night. Proliferated cells were collected, and plasmids were purified in accordance with an instruction manual of Plasmid Midi Kit (QIAGEN).

2. Co-Transfection

To Sf9 cells ($1.0 \times 10^6$) plated in a 25-cm² flask was added a serum-free Sf-900 II medium (product of Invitrogen) (200 μL) containing an expression vector harboring a cDNA fragment encoding Pro-CE (2.3 μg), a linear AcNPV DNA (85 ng), and LIPOFECTIN Reagent (product of Invitrogen) (5 μL). After the culture had been allowed to stand at 28° C. for six hours, a serum-free Sf-900 II medium was further added so as to adjust the volume of the culture liquid to 5 mL. The culture was further cultivated at 28° C. for five days, and the culture supernatant was collected. The supernatant was employed as a co-transfection solution.

3. Purification of Recombinant Virus

The recombinant virus was purified through the plaque assay method. The specific procedure is as follows.

Sf9 cells ($2.0 \times 10^6$) were plated onto a plate (diameter: 60 mm) and allowed to stand at 28° C. for one hour, whereby the cells were adhered to the bottom surface. The aforementioned co-transfection solution was diluted with a serum-free Sf-900 II medium at dilution factors of $10^4$, $10^5$, $10^6$, and $10^7$. An aliquot (1 mL) of each of these diluted solutions was added to the cells, followed by gentle shaking at room temperature for one hour. After removal of the plate supernatant (virus fluid), a serum-free Sf-900 II, medium (4 mL) containing 0.5% SeaKemGTG agarose (product of BMA) was added to the plate, and stationary culture was performed at 28° C. for eight days. From each culture medium, six plaques of infected insect cells including no polyhedra were collected. The plaques of each medium were suspended in a serum-free Sf-900 II medium (1 mL), to thereby obtain a virus fluid.

4. Amplification of Recombinant Virus

Next, amplification of the recombinant virus (preparation of recombinant virus fluid) was performed. The specific procedure is as follows.

To Sf9 cells ($2.0 \times 10^6$) plated in a 25-cm² flask was added each (0.5 mL) of the aforementioned virus fluids, followed by stationary cultivation at 28° C. for one hour. A serum-free Sf-900 II medium was added to the culture so as to adjust the volume of the culture liquid to 5 mL, and the culture was further stationary-cultivated for three days, to thereby yield a first-generation virus fluid.

To Sf9 cells ($6.0 \times 10^6$) plated in a 75-cm² flask was added the entirety of the aforementioned first-generation virus fluid, followed by stationary cultivation at 28° C. for one hour. Subsequently, a serum-free Sf-900 II medium (10 mL) was added to the culture, followed by stationary cultivation for three days. After completion of cultivation, the culture supernatant was recovered and centrifuged at 3,000×g and 4° C. for 15 minutes, to thereby fractionate into the supernatant and the precipitate. The culture supernatant was recovered and employed as a second-generation virus fluid.

5. Production of Recombinant Virus Fluid

Insect cells (expresSF+) which were in the logarithmic growth phase during cultivation were diluted with a serum-free Sf-900 II medium so as to adjust the concentration to $1.5 \times 10^6$ cells/mL, and the diluted product (50 mL) was placed in a 125-mL Erlenmeyer flask. The aforementioned second-generation virus fluid (0.5 mL) was added thereto, and the mixture was subjected to shake cultivation at 130 rpm and 28° C. for three days. After completion of cultivation, the culture liquid was centrifuged at 10,000×g and 4° C. for 30 minutes, to thereby fractionate into the supernatant and the precipitate. The culture supernatant was recovered and employed as a third-generation virus fluid.

6. Confirmation of Gene Insertion

Subsequently, insertion of a DNA fragment into a cell was confirmed through the following procedure.

The thus-recovered third-generation virus fluid (0.7 mL) was placed in a 1.5-mL microtube, and an equiamount of 20% polyethylene glycol and 1M sodium chloride solution were added to the microtube, followed by sufficiently mixing. The mixture was allowed to stand for one hour. Thereafter, the culture liquid was centrifuged at 10,000×g for 10 minutes, to thereby fractionate into the supernatant and the precipitate. The precipitate was recovered and, in accordance with a manual of QIAamp DNA Miki Kit (QIAGEN), dissolved in Buffer ALT (180 μL), whereby a viral DNA fragment was extracted. PCR was performed in the following manner by use of the thus-extracted viral DNA fragment as a template and the following primers.
SEQ ID NO: 11: PSC N3F
SEQ ID NO: 12: PSC N3R To a 0.2-mL sample tube, the aforementioned viral DNA fragment (1 μL), 10×PCR buffer for KOD-Plus-(5 μL), 2 mM dNTPs (5 μL), 25 mM magnesium sulfate solution (2 μL), primers PSC N3F and PSC N3R (4 pmol/mL, 3.75 μL, each), KOD-Plus-DNA polymerase (product of TOYOBO) (1 μL), and sterilized pure water (19.5 μL) were added, and the mixture was sufficiently stirred. The mixture was subjected to PCR for 30 cycles, each cycle consisting of 94° C. for one minute, 58° C. for one minute, and 72° C. for four minutes.

The PCR product (10 μL) was subjected to electrophoresis on agarose gel, and the length of the amplified fragments was determined. A PCR product of a fragment having a target length was purified, and the sequences of the N-terminus and the C-terminus were determined, through use of the same reagents and apparatuses as employed in the aforementioned "1. Construction of expression vector." The following primers represented by SEQ ID NOs: 13 and 14 were employed.
SEQ ID NO: 13: PSC NF2
SEQ ID NO: 14: PSC 3

7. Titer Determination

Sf9 cells ($2.0 \times 10^6$) were plated onto a plate (diameter: 60 mm) and allowed to stand at 28° C. for one hour, whereby the cells were adhered to the bottom surface. Subsequently, the culture liquid was removed. Separately, the third-generation virus fluid was diluted with a serum-free Sf-900 II medium at dilution factors of $10^5$, $10^6$, $10^7$, and $10^8$. An aliquot (1 mL) of each of these solutions was added to the plate, followed by gentle shaking at room temperature for one hour. After removal of the plate supernatant (virus fluid), a serum-free Sf-900 II medium (4 mL) containing 0.5% SeaKemGTG agarose (product of BMA) was added to the plate, and stationary culture was performed at 28° C. for seven days. In each culture medium, the number of observed plaques was counted, thereby determining the titer.

8. Expression Test

Insect cells (expresSF+) were diluted with a serum-free Sf-900 II medium so as to adjust the concentration to $1.5 \times 10^6$ cells/mL, and the diluted product (100 mL/per flask) was placed in nine 250-mL Erlenmeyer flasks. The aforementioned third-generation virus fluid was added thereto so as to attain MOIs of 0.2, 1, and 5 (3 flasks each), respectively. Each mixture was subjected to shake cultivation at 130 rpm and 28° C. for 48, 72, and 96 hours. After completion of cultivation, each culture liquid was centrifuged at 3,000×g and 4° C. for 20 minutes, to thereby fractionate into the supernatant and the precipitate.

9. Detection of Expression Product

Each of the samples collected in "8. Expression test" above was subjected to SDS-PAGE through a routine method. A protein was transferred to a blotting membrane through the semi-dry blotting method, and western blotting was performed under the following conditions. Note that the "DNA fragment encoding Pro-CE" incorporated into the virus was designed so as to express a His-Tag-bound protein.

Sample treatment: The supernatant was mixed with Laemmli Sample Buffer (product of BIO-RAD), and the mixture was heated at 99° C. for three minutes. The precipitate (200 µL) was mixed with PBS (400 µL), to thereby form an aqueous suspension. Laemmli Sample Buffer was added to the suspension, and the mixture was heated at 99° C. for three minutes.

Amount of applied sample: 20 µL/lane

SDS-PAGE gel concentration: 10 to 20% gel (product of BIO-RAD)

Voltage application in SDS-PAGE: 150V, CV

Blotting membrane: PVDF

Voltage application in blotting: 15V, CV, 30 minutes

Primary antibody: Penta.His Antibody (product of QIAGEN)

Secondary antibody: Goat Anti-Mouse IgG(H+L)-HRP Conjugate (product of BIO-RAD)

Detection: Immobilon Western Chemiluminescent HRP Substrate (product of Milipore)

10. Results

FIG. 1 shows the results of sequence analysis of the target sequence of the recombinant virus. The upper column shows the analysis results, and the lower columns show the sequence of Pro-CE. As is clear from FIG. 1, the recombinant virus was found to have the same N-terminal sequence and C-terminal sequence as those of Pro-CE. Thus, the presence of a DNA fragment having a nucleotide sequence encoding Pro-CE was confirmed in the recombinant virus.

The titer was $0.7 \times 10^8$ pfu/mL.

In the results of "9. Detection of expressed product" above, a band attributed to reaction with an anti-His-Tag antibody was observed at a target position (about 40 kDa) (FIG. 2). In FIG. 2, M represents a molecular weight marker, 48, 72, and 96 represent 48-hour-infection-lane, 72-hour-infection-lane, and 96-hour-infection-lane, respectively, S represents a non-virus-infected lane, and A represents a wild-type-virus-infected lane. As is clear from FIG. 2, expression of Pro-CE was verified.

Example 2

Detection of Recombinant Pro-CE Activity

Insect cells (expresSF+) were diluted with a serum-free Sf-900 II medium so as to adjust the concentration to $1.5 \times 10^6$ cells/mL, and the diluted product (100 mL/per flask) was placed in nine 250-mL Erlenmeyer flasks. The aforementioned third-generation virus fluid was added thereto so as to attain MOIs of 0.2, 1, and 5 (3 flasks each), respectively. Each mixture was subjected to shake cultivation at 130 rpm and 28° C. for 48, 72, and 96 hours. After completion of cultivation, each culture liquid was centrifuged at 3,000×g and 4° C. for 20 minutes, to thereby fractionate into the supernatant and the precipitate. The supernatant was preserved in a frozen state.

Sample 1: MOI=0.2, 48 hours
Sample 2: MOI=0.2, 72 hours
Sample 3: MOI=0.2, 96 hours
Sample 4: MOI=1, 48 hours
Sample 5: MOI=1, 72 hours
Sample 6: MOI=1, 96 hours
Sample 7: MOI=5, 48 hours
Sample 8: MOI=5, 72 hours
Sample 9: MOI=5, 96 hours
Sample 10: non-virus-infected cells
Sample 11: wild-type-virus-infected cells Reagents DS-3GII fraction: Factor G derived from a horseshoe crab hemocyte extract [product fractionated/purified with dextran sulfate Sepharose CL-6B (hereinafter referred to as DS-Sepharose)]

DS-10AII fraction: Pro-CE derived from a horseshoe crab hemocyte extract (product purified with DS-Sepharose)

BG: CSBG (1,495 ng/vial) dissolved in distilled water (1.495 mL), followed by ×10-stepwise dilution 1. Reactivity of Supernatant Fractions Employing Factor G at a BG Concentration of 1 to 100 ng/mL Firstly, there was investigated whether or not the expressed protein maintained Pro-CE activity in each of the supernatants of the aforementioned nine samples.

Figure 3:
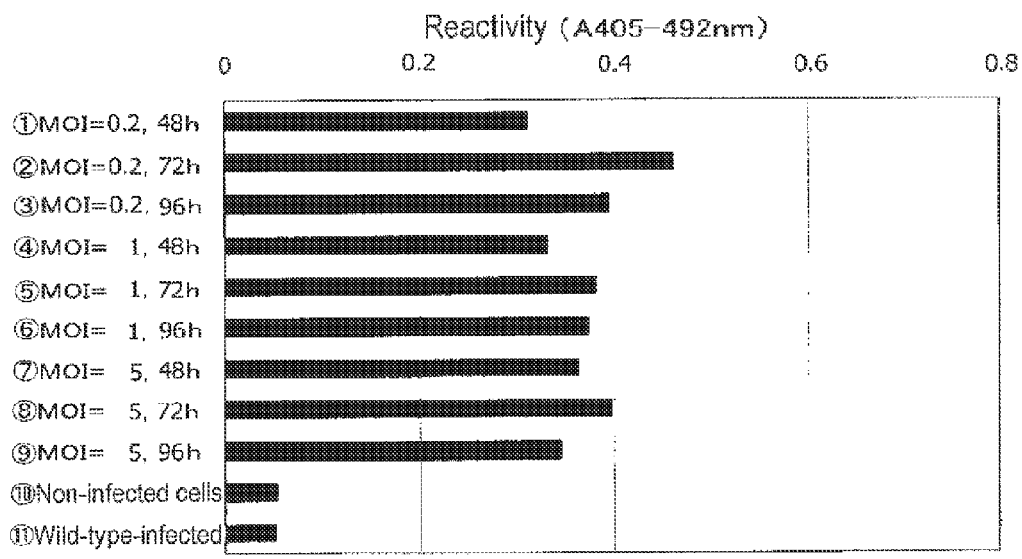
FIG. 3 depicts a graph showing the reactivity of Pro-CE-expressing baculovirus supernatant fractions at a BG concentration of 1 ng/mL.
Figure 4:
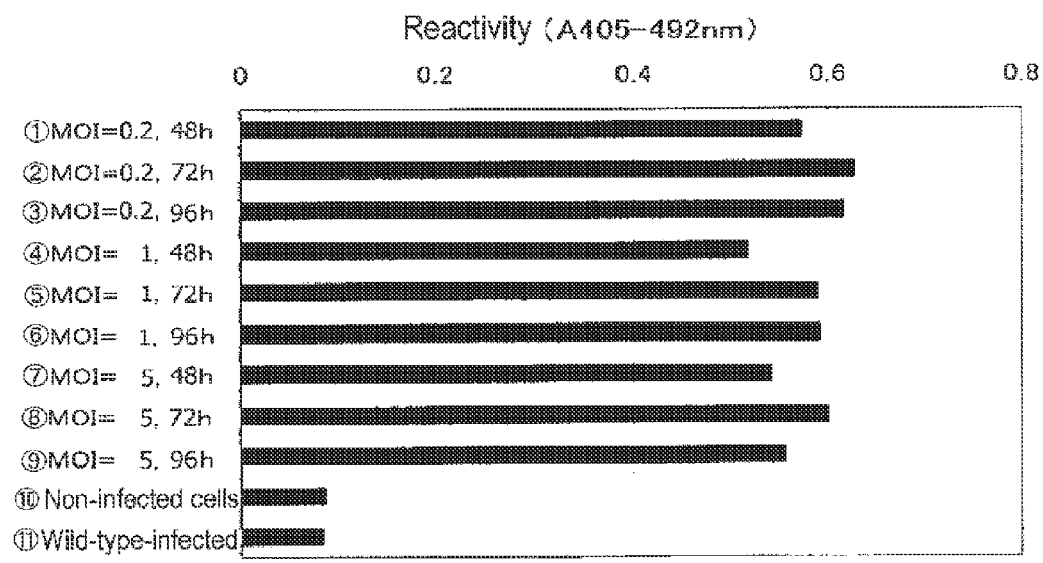
FIG. 4 depicts a graph showing the reactivity of Pro-CE-expressing baculovirus supernatant fractions at a BG concentration of 10 ng/mL.

Each supernatant fraction recovered after culture was 10-fold diluted with 50 mL Tris-HCl buffer (pH: 7.5) containing 150 mM NaCl. To each diluted product (25 µL), there were added DS-3GII fraction (25 µL), dextran (final concentration: 2.4%), Tris-HCl buffer (pH: 8.0) (final concentration: 80 mM), $MgSO_4$ (final concentration: 64 mM), $CaCl_2$ (final concentration: 0.4 mM), $Na_2SO_4$ (final concentration: 8 mM), distilled water for injection (15 µL), Boc-Leu-Gly-Arg-pNA substrate (see the aforementioned Patent Document 1) (final concentration: 0.24 mM), and a BG solution (0, 1, 10, or 100 ng/mL) (25 µL). The total volume of the sample was adjusted to 125 µL, and the sample was transferred to a Wellreader SK603, where it was allowed to react at 37° C. for two hours. The absorbance of the sample was automatically determined at a measurement wavelength of 405 nm (control wavelength: 492 nm). As a positive control, a DS-10AII fraction was employed. The measurement was carried out twice, and the average absorbance was calculated. The results are shown in FIGS. 3 and 4 and Table 1.

TABLE 1

[Endpoint Assay]

| Sample | | Sample No. | Reactivity (A 405 to 492 nm) | | Average |
|---|---|---|---|---|---|
| CSBG (0 ng/mL) | Recombinant Pro-CE (×10 diluted) | 1) MOI = 0.2, 48 h | 0.029 | 0.029 | 0.029 |
| | | 2) MOI = 0.2, 72 h | 0.029 | 0.030 | 0.030 |
| | | 3) MOI = 0.2, 96 h | 0.031 | 0.031 | 0.031 |
| | | 4) MOI = 1, 48 h | 0.030 | 0.032 | 0.031 |
| | | 5) MOI = 1, 72 h | 0.030 | (0.041) | 0.030 |
| | | 6) MOI = 1, 96 h | 0.031 | 0.030 | 0.031 |
| | | 7) MOI = 5, 48 h | 0.030 | 0.030 | 0.030 |
| | | 8) MOI = 5, 72 h | 0.030 | 0.030 | 0.030 |
| | | 9) MOI = 5, 96 h | 0.031 | 0.031 | 0.031 |

TABLE 1-continued

[Endpoint Assay]

| Sample | Sample No. | | Reactivity (A 405 to 492 nm) | | Average |
|---|---|---|---|---|---|
| | (×10 diluted) | 10) Non-infected cells | 0.029 | 0.030 | 0.030 |
| | | 11) Wild-type-infected | 0.030 | 0.029 | 0.030 |
| | | DS-10AII fraction (control) | 0.040 | 0.041 | 0.041 |
| CSBG (1 ng/mL) | Recombinant Pro-CE (×10 diluted) | 1) MOI = 0.2, 48 h | 0.308 | 0.317 | 0.313 |
| | | 2) MOI = 0.2, 72 h | 0.462 | 0.461 | 0.462 |
| | | 3) MOI = 0.2, 96 h | 0.396 | 0.397 | 0.397 |
| | | 4) MOI = 1, 48 h | 0.332 | 0.331 | 0.332 |
| | | 5) MOI = 1, 72 h | 0.382 | 0.380 | 0.381 |
| | | 6) MOI = 1, 96 h | 0.376 | 0.370 | 0.373 |
| | | 7) MOI = 5, 48 h | 0.359 | 0.365 | 0.362 |
| | | 8) MOI = 5, 72 h | 0.401 | 0.396 | 0.399 |
| | | 9) MOI = 5, 96 h | 0.344 | 0.344 | 0.344 |
| | (×10 diluted) | 10) Non-infected cells | 0.052 | 0.053 | 0.053 |
| | | 11) Wild-type-infected | 0.051 | 0.052 | 0.052 |
| | | DS-10AII fraction (control) | 0.510 | 0.481 | 0.496 |
| CSBG (10 ng/mL) | Recombinant Pro-CE (×10 diluted) | 1) MOI = 0.2, 48 h | 0.567 | 0.578 | 0.573 |
| | | 2) MOI = 0.2, 72 h | 0.612 | 0.642 | 0.627 |
| | | 3) MOI = 0.2, 96 h | 0.606 | 0.628 | 0.617 |
| | | 4) MOI = 1, 48 h | 0.516 | 0.518 | 0.517 |
| | | 5) MOI = 1, 72 h | 0.589 | 0.588 | 0.589 |
| | | 6) MOI = 1, 96 h | 0.595 | 0.589 | 0.592 |
| | | 7) MOI = 5, 48 h | 0.527 | 0.555 | 0.541 |
| | | 8) MOI = 5, 72 h | 0.605 | 0.597 | 0.601 |
| | | 9) MOI = 5, 96 h | 0.552 | 0.558 | 0.555 |
| | (×10 diluted) | 10) Non-infected cells | 0.084 | 0.084 | 0.084 |
| | | 11) Wild-type-infected | 0.083 | 0.083 | 0.083 |
| | | DS-10AII fraction (control) | 0.699 | 0.725 | 0.712 |

As shown in Table 1, the virus-infected cell culture supernatants of samples 1 to 9 each contain the enzyme in almost the same amount, indicating the presence of expression of Pro-CE in all fractions. In particular, sample 2 exhibited strong activity.

Figure 5:
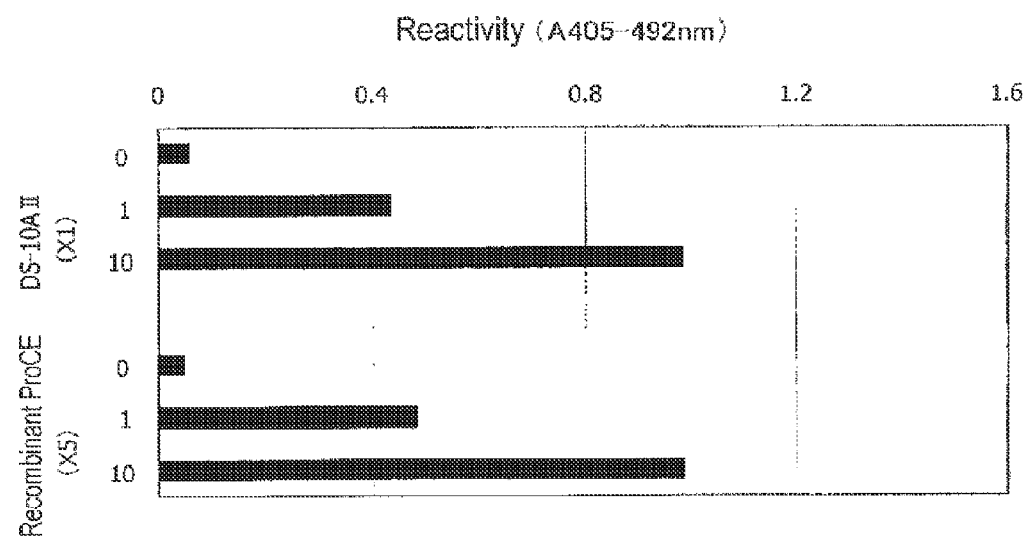
FIG. 5 depicts the results of a comparison between recombinant baculovirus-produced Pro-CE with a DS-10AII fraction derived from horseshoe crab hemocyte extract, with respect to reactivity of BG in a DS-3GII fraction.

Table 2 and FIG. 5 show the results of comparison of recombinant Pro-CE of sample 2 with DS-10AII fraction in terms of in enzymatic activity.

TABLE 2

[Endpoint assay]

| Sample | | CSBG concentration (ng/mL) | Reactivity (A 405 to 492 nm) | | Average | ΔA |
|---|---|---|---|---|---|---|
| DS-3GII(X1) | DS-10AII (X1) | 0 | 0.056 | 0.060 | 0.058 | — |
| | | 1 | 0.440 | 0.434 | 0.437 | 0.379 |
| | | 10 | 0.969 | 1.002 | 0.986 | 0.928 |
| | Recombinant ProCE (X5) | 0 | 0.051 | 0.049 | 0.050 | — |
| | | 1 | 0.480 | 0.487 | 0.484 | 0.434 |
| | | 10 | 0.988 | 0.986 | 0.987 | 0.937 |

As is clear from Table 2, the recombinant Pro-CE exhibited an enzymatic activity almost equivalent to that of Pro-CE derived from a horseshoe crab hemocyte extract.

Figure 6:
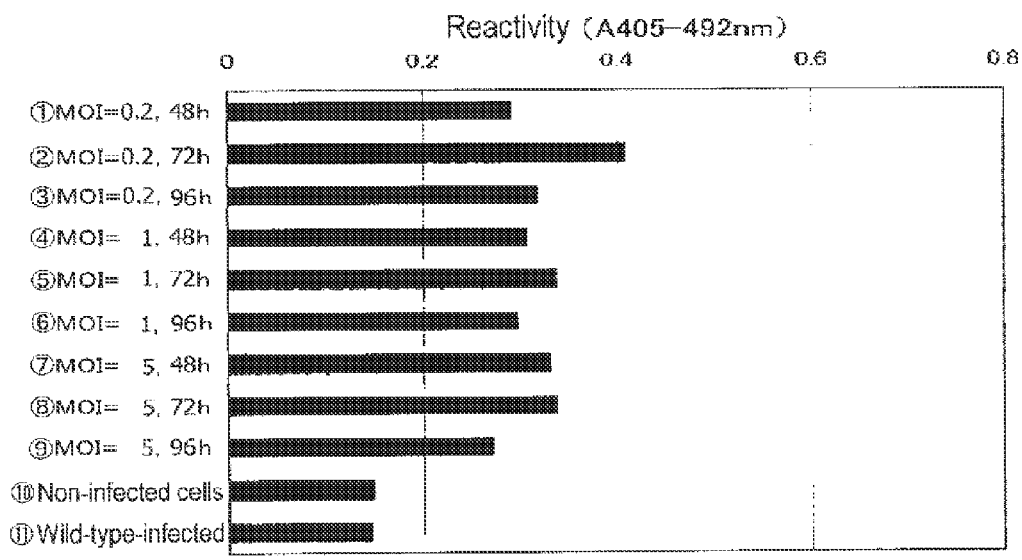
FIG. 6 depicts a graph showing the reactivity of Pro-CE-expressing baculovirus supernatant fractions at an Et concentration of 10 ng/mL.
Figure 7:
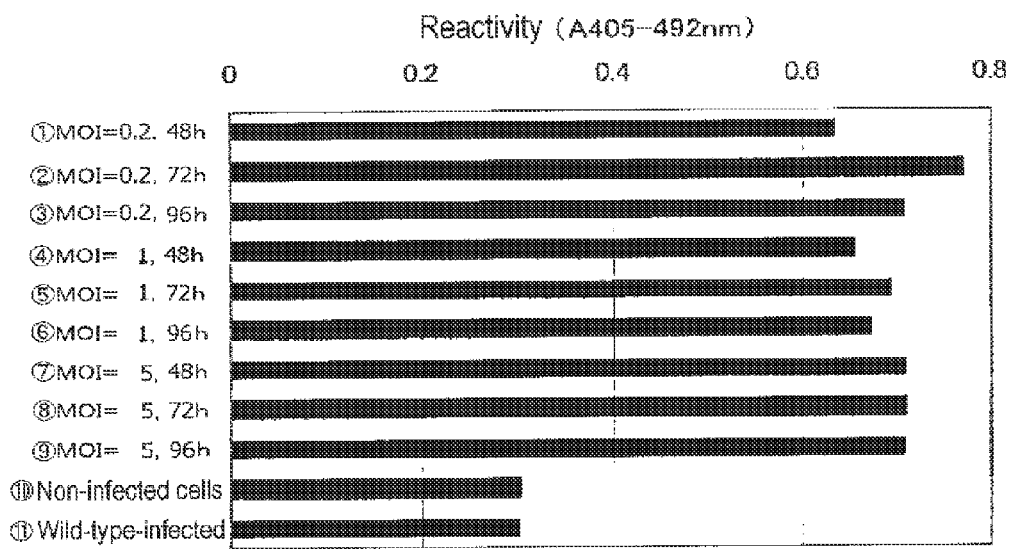
FIG. 7 depicts a graph showing the reactivity of Pro-CE-expressing baculovirus supernatant fractions at an Et concentration of 100 ng/mL.

2. Reactivity of Supernatant Fractions Employing Factors B and C at an Et Concentration of 1 to 100 ng/mL The recombinant Pro-CE or the DS10-AII fraction (positive control, Pro-CE-eluted fraction); a DS-12BCI fraction (factor-B-C-eluted fraction) (25 μL) instead of factors B and C; and Et were added to the diluted products obtained in [1.] above. The Et concentration was adjusted to 0, 1, 10, or 100 ng/mL. The other mixture components were added in amounts and at concentrations equivalent to those employed in [1.]. The total volume of each sample was adjusted to 125 μL, and the sample was transferred to a Wellreader SK603, where it was allowed to react at 37° C. for 30 minutes. The absorbance of the sample was automatically determined at a measurement wavelength of 405 nm (control wavelength: 492 nm). The measurement was carried out twice, and the average absorbance was calculated. The results are shown in FIGS. 6 and 7 and Table 3.

TABLE 3

[Endpoint Assay]

| Sample | | Sample No. | Reactivity (A 405 to 492 nm) | | Average |
|---|---|---|---|---|---|
| Endotoxin (0 ng/mL) | Recombinant Pro-CE (×10 diluted) | 1) MOI = 0.2, 48 h | 0.036 | 0.035 | 0.036 |
| | | 2) MOI = 0.2, 72 h | 0.036 | 0.037 | 0.037 |
| | | 3) MOI = 0.2, 96 h | 0.038 | 0.037 | 0.038 |
| | | 4) MOI = 1, 48 h | 0.037 | 0.038 | 0.038 |
| | | 5) MOI = 1, 72 h | 0.037 | 0.039 | 0.038 |
| | | 6) MOI = 1, 96 h | 0.037 | 0.037 | 0.037 |
| | | 7) MOI = 5, 48 h | 0.038 | 0.038 | 0.038 |
| | | 8) MOI = 5, 72 h | 0.038 | 0.038 | 0.038 |
| | | 9) MOI = 5, 96 h | 0.038 | 0.039 | 0.039 |
| | (×10 diluted) | 10) Non-infected cells | 0.036 | 0.038 | 0.037 |
| | | 11) Wild-type-infected | 0.039 | 0.038 | 0.039 |
| | | DS-10AII fraction (control) | 0.044 | 0.044 | 0.044 |
| Endotoxin (1 ng/mL) | Recombinant Pro-CE (×10 diluted) | 1) MOI = 0.2, 48 h | 0.066 | 0.067 | 0.067 |
| | | 2) MOI = 0.2, 72 h | 0.084 | 0.083 | 0.084 |
| | | 3) MOI = 0.2, 96 h | 0.070 | 0.072 | 0.071 |
| | | 4) MOI = 1, 48 h | 0.070 | 0.071 | 0.071 |
| | | 5) MOI = 1, 72 h | 0.075 | 0.075 | 0.075 |
| | | 6) MOI = 1, 96 h | 0.069 | 0.069 | 0.069 |
| | | 7) MOI = 5, 48 h | 0.074 | 0.075 | 0.075 |
| | | 8) MOI = 5, 72 h | 0.074 | 0.077 | 0.076 |
| | | 9) MOI = 5, 96 h | 0.065 | 0.069 | 0.067 |
| | (×10 diluted) | 10) Non-infected cells | 0.049 | 0.054 | 0.052 |
| | | 11) Wild-type-infected | 0.051 | 0.053 | 0.052 |
| | | DS-10AII fraction (control) | 0.156 | 0.143 | 0.150 |
| Endotoxin (10 ng/mL) | Recombinant Pro-CE (×10 diluted) | 1) MOI = 0.2, 48 h | 0.306 | 0.276 | 0.291 |
| | | 2) MOI = 0.2, 72 h | 0.420 | 0.395 | 0.408 |
| | | 3) MOI = 0.2, 96 h | 0.317 | 0.317 | 0.317 |
| | | 4) MOI = 1, 48 h | 0.306 | 0.302 | 0.304 |
| | | 5) MOI = 1, 72 h | 0.333 | 0.338 | 0.336 |
| | | 6) MOI = 1, 96 h | 0.295 | 0.297 | 0.296 |
| | | 7) MOI = 5, 48 h | 0.333 | 0.329 | 0.331 |
| | | 8) MOI = 5, 72 h | 0.339 | 0.337 | 0.338 |
| | | 9) MOI = 5, 96 h | 0.271 | 0.268 | 0.270 |
| | (×10 diluted) | 10) Non-infected cells | 0.146 | 0.147 | 0.147 |
| | | 11) Wild-type-infected | 0.146 | 0.145 | 0.146 |
| | | DS-10AII fraction (control) | 0.722 | 0.724 | 0.723 |
| Endotoxin (100 ng/mL) | Recombinant Pro-CE (×10 diluted) | 1) MOI = 0.2, 48 h | 0.634 | 0.634 | 0.634 |
| | | 2) MOI = 0.2, 72 h | 0.736 | 0.806 | 0.771 |
| | | 3) MOI = 0.2, 96 h | 0.727 | 0.686 | 0.707 |
| | | 4) MOI = 1, 48 h | 0.662 | 0.650 | 0.656 |
| | | 5) MOI = 1, 72 h | 0.707 | 0.678 | 0.693 |
| | | 6) MOI = 1, 96 h | 0.677 | 0.666 | 0.672 |
| | | 7) MOI = 5, 48 h | 0.729 | 0.693 | 0.711 |
| | | 8) MOI = 5, 72 h | 0.720 | 0.699 | 0.710 |
| | | 9) MOI = 5, 96 h | 0.710 | 0.704 | 0.707 |
| | (×10 diluted) | 10) Non-infected cells | 0.306 | 0.301 | 0.304 |
| | | 11) Wild-type-infected | 0.300 | 0.302 | 0.301 |
| | | DS-10AII fraction (control) | 0.733 | 0.757 | 0.745 |

As is clear from Table 3, all virus-infected cell culture supernatants of samples each contain Pro-CE. In particular, sample 2 exhibited strong activity.

Example 3

Detection of Expression of Activity in a Complete Reconstitution System Employing Recombinant Pro-CE and Recombinant Factor G Reagents (1) recombinant factor G (culture supernatant; α-subunit:β-subunit=2:1)
(2) recombinant Pro-CE (culture supernatant of sample 2 in Example 2)
(3) BG:CSBG (1,495 ng/vial) dissolved in distilled water (1.495 mL), followed by ×10-stepwise dilution Each of the culture supernatants (1) and (2), which had been produced through the method disclosed in Japanese Patent Application Laid-Open (kokai) No. 2006-271384 (Patent Document 2), was five-fold diluted with Tris-HCl buffer (pH: 7.5) (50 mL) containing 150 mM NaCl. In this experiment, a nucleotide sequence represented by SEQ ID NO: 21 was employed as a DNA fragment encoding α-subunit of factor G. To the thus-diluted recombinant factor G (25 µL), recombinant Pro-CE (25 µL), Tris-HCl buffer (pH: 8.0) (final concentration: 80 mM), $MgSO_4$ (final concentration: 64 mM), $CaCl_2$ (final concentration: 0.4 mM), $Na_2SO_4$ (final concentration: 8 mM), distilled water for injection (15 µL), dextran (final concentration: 2.4%), Boc-Leu-Gly-Arg-pNA substrate (final concentration: 0.24 mM), and a BG solution (0, 1, or 10 ng/mL) (25 µL) were added. The total volume of each sample was adjusted to 125 µL, and the sample was transferred to a Wellreader SK603, where it was allowed to react through a routine procedure. The absorbance of the sample was automatically determined at a measurement wavelength of 405 nm (control wavelength: 492 nm). The measurement was carried out twice, and the average absorbance was calculated. The results are shown in Table 4 and FIG. 8.

TABLE 4

[Endpoint assay]

| Sample | | CSBG concentration (ng/mL) | Reactivity (A 405 to 492 nm) ($\times 10^3$) | | Average ($\times 10^3$) | ΔA ($\times 10^3$) |
|---|---|---|---|---|---|---|
| Recombinant Factor G (×5) | Recombinant ProCE (X5) | 0 | 0.079 | 0.076 | 0.078 | — |
| | | 1 | 0.140 | 0.138 | 0.139 | 0.061 |
| | | 10 | 0.543 | 0.520 | 0.532 | 0.454 |

Figure 8:
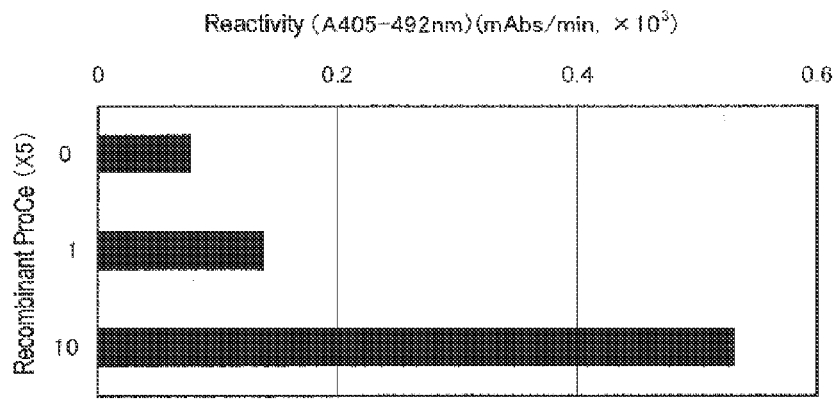
FIG. 8 depicts the results of an analysis of the activity of recombinant Pro-CE in a complete reconstitution system containing recombinant Pro-CE and recombinant factor G; the graph depicts the reactivity of BG in recombinant factor G (5-fold diluted).

As is clear from Table 4 and FIG. 8, similar to the case of a factor contained in amebocyte lysate (native factor LAL), reaction of BG proceeds in a concentration-dependent manner through employment of recombinant factor G and recombinant Pro-CE in combination. Also, the same enzymatic activity as that of native factor LAL was found to be expressed.

Example 4

Detection of et Reaction by Use of a Complete Reconstitution System Employing Recombinant Pro-CE, Recombinant Factor B, and Recombinant Factor C A nucleotide sequence targeting for expressing factor B in which a His-Tag sequence is attached to the C-terminus was synthesized, and the synthesized nucleotide sequence was introduced into a transfer vector (pPSC8). The thus-obtained expression vector (factor B/pPSC8) DNA fragment and a baculovirus (AcNPV) DNA fragment were co-transfected into Sf9 cells. The virus fluid obtained from the culture supernatant was purified and amplified. The viral DNA fragment was extracted from the cells and sequenced, to thereby determine the sequences of the N- and C-terminuses of the introduced gene fragment. The expresSF+ cells (equivalent to 100 mL of culture liquid) were caused to be infected with the thus-produced recombinant virus so as to attain MOIs of 0.02, 0.1, and 0.5, and culture supernatants and precipitates were recovered at hour 48, hour 72, and hour 96. The recovered expression products were analyzed through western blotting employing an anti-His-Tag antibody for confirming expression. Subsequently, Et(0, 0.01, 0.1, 1, 10, or 100 µg/mL) was added to a reaction system in the presence of this factor, recombinant factor C (product of PyroGene), and recombinant ProCE, and the system was allowed to react at 37° C. for one hour. Through analyzing the ability to hydrolyze a synthetic substrate (Boc-Leu-Gly-Arg-pNA) in the presence of Pro-CE, activation of ProCE (i.e., formation of CE) was determined.

Figure 9:
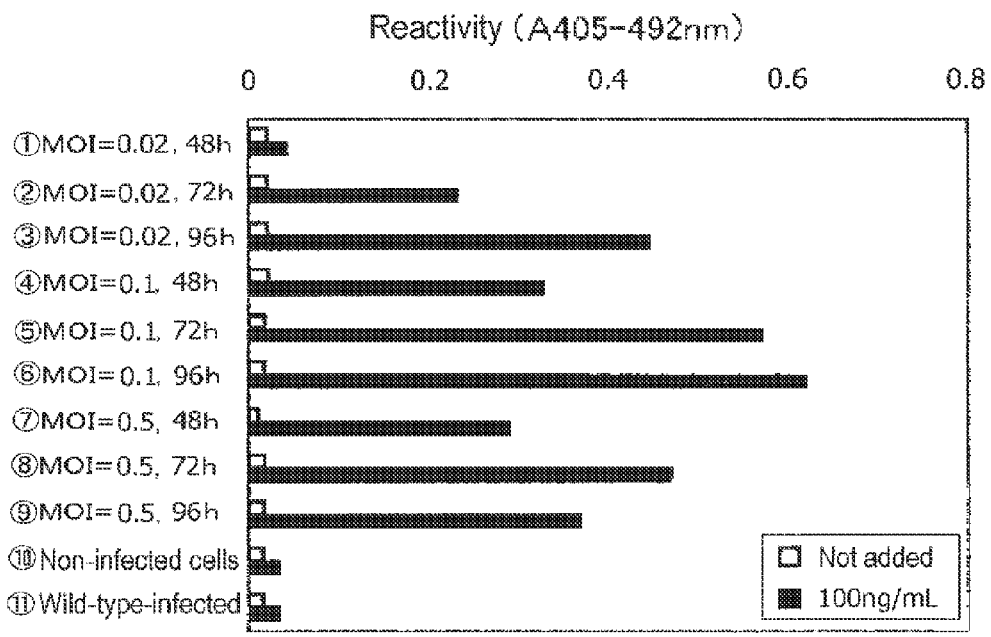
FIG. 9 depicts a graph showing the investigation results of the activity of recombinant factor B to be employed in the Et reaction, tested with and without Et.

Through the same experiment as carried out in Example 1, the activity of recombinant factor B was confirmed. In the study of reactivity of Et, the highest Et reactivity was attained in a sample (MOI=0.1, 96 h). Thus, the sample was employed for reconstitution of the factor C-cascade (Table 5 and FIG. 9).

TABLE 5

[Endpoint Assay]

| | Sample | Sample No. | Reactivity (A 405 to 492 nm) | | Average |
|---|---|---|---|---|---|
| Endotoxin (0 ng/mL) | Recombinant Factor B (×5 diluted) | 1) MOI = 0.02, 48 h | 0.022 | — | 0.022 |
| | | 2) MOI = 0.02, 72 h | 0.022 | — | 0.022 |
| | | 3) MOI = 0.02, 96 h | 0.022 | — | 0.022 |
| | | 4) MOI = 0.1, 48 h | 0.023 | — | 0.023 |
| | | 5) MOI = 0.1, 72 h | 0.018 | — | 0.018 |
| | | 6) MOI = 0.1, 96 h | 0.018 | — | 0.018 |
| | | 7) MOI = 0.5, 48 h | 0.010 | — | 0.010 |
| | | 8) MOI = 0.5, 72 h | 0.019 | — | 0.019 |
| | | 9) MOI = 0.5, 96 h | 0.018 | — | 0.018 |
| | (×5 diluted) | 10) Non-infected cells | 0.016 | — | 0.016 |
| | | 11) Wild-type-infected | 0.016 | — | 0.016 |
| Endotoxin (10 ng/mL) | Recombinant Factor B (×5 diluted) | 1) MOI = 0.02, 48 h | 0.044 | 0.043 | 0.044 |
| | | 2) MOI = 0.02, 72 h | 0.232 | 0.230 | 0.231 |
| | | 3) MOI = 0.02, 96 h | 0.440 | 0.451 | 0.446 |
| | | 4) MOI = 0.1, 48 h | 0.340 | 0.318 | 0.329 |
| | | 5) MOI = 0.1, 72 h | 0.568 | 0.572 | 0.570 |
| | | 6) MOI = 0.1, 96 h | 0.617 | 0.622 | 0.620 |
| | | 7) MOI = 0.5, 48 h | 0.300 | 0.276 | 0.288 |
| | | 8) MOI = 0.5, 72 h | 0.478 | 0.462 | 0.470 |
| | | 9) MOI = 0.5, 96 h | 0.368 | 0.369 | 0.369 |
| | (×5 diluted) | 10) Non-infected cells | 0.034 | 0.033 | 0.034 |
| | | 11) Wild-type-infected | 0.035 | 0.034 | 0.035 |

In order to confirm whether or not cascade reaction proceeds when a different *limulus*-derived factor is employed in combination, recombinant factor C (derived from *Tachypleus rotundicauda*), which is a commercial element of PyroGene (product of Cambrex) was used.

Reagents
(1) recombinant factor B (culture supernatant, MOI=0.1, 96 h)
(2) recombinant Pro-CE (culture supernatant of sample 2 in Example 2)
(3) recombinant factor C (PyroGene (commercial product), non-diluted)
(4) Et: *E. coli* O111:B4-derived (Product of Sigma) was processed with distilled water to 1 mg/mL, followed by ×10-stepwise dilution In order to confirm that the experimental results are attributable to reconstitution of the cascade, the following combination samples were tested.
Sample A: recombinant Pro-CE, recombinant factor B, and recombinant factor C
Sample B: recombinant Pro-CE, recombinant factor B, and distilled water
Sample C: recombinant Pro-CE, recombinant factor C, and distilled water
Sample D: recombinant factor B, recombinant factor C, and distilled water
Sample E: recombinant Pro-CE and distilled water
Sample F: recombinant factor B and distilled water
Sample G: recombinant factor C and distilled water The aforementioned culture supernatants (1) and (2) employed in the samples each were diluted in advance five-fold with ice-cooled Tris-HCl buffer (pH: 7.5) (50 mL) containing 150 mM NaCl. The total volume of each sample was adjusted to 60 µL.

To each sample, there were added Tris-HCl buffer (pH: 8.0) (final concentration: 80 mM), $MgSO_4$ (final concentration: 64 mM), $CaCl_2$ (final concentration: 0.4 mM), $Na_2SO_4$ (final concentration: 8 mM), dextran (final concentration: 2.4%), distilled water for injection (15 µL), Boc-Leu-Gly-Arg-pNA substrate (final concentration: 0.24 mM), and Et solution (0 or 100 ng/mL) (25 µL). The total volume of the sample was adjusted to 125 µL, and the sample was transferred to a Wellreader SK603, where it was allowed to react at 37° C. for 10 hours. The absorbance of the sample was automatically determined at a measurement wavelength of 405 nm (control wavelength: 492 nm). The measurement was carried out twice, and the average absorbance was calculated. The results are shown in Table 6 and FIG. 10.

TABLE 6

| Et concentration (ng/mL) | Reconstitution system | Reactivity (A405 to 492 nm) | | Av. |
|---|---|---|---|---|
| 0 | (A) PCE + FB + FC | 0.024 | 0.022 | 0.023 |
|  | (B) PCE + FB | 0.023 | 0.022 | 0.023 |
|  | (C) PCE + FC | 0.020 | 0.020 | 0.020 |
|  | (D) FB + FC | 0.024 | 0.025 | 0.025 |
|  | (E) PCE | 0.009 | 0.006 | 0.008 |
|  | (F) FB | 0.022 | 0.022 | 0.022 |
|  | (G) FC | 0.022 | 0.023 | 0.023 |
| 100 | (A) PCE + FB + FC | 0.652 | 0.645 | 0.649 |
|  | (B) PCE + FB | 0.022 | 0.023 | 0.023 |
|  | (C) PCE + FC | 0.029 | 0.030 | 0.030 |
|  | (D) FB + FC | 0.032 | 0.034 | 0.033 |
|  | (E) PCE | 0.006 | 0.006 | 0.006 |
|  | (F) FB | 0.024 | 0.026 | 0.025 |
|  | (G) FC | 0.034 | 0.035 | 0.035 |

The hydrolysis performance of the factors (samples A, B, and E to G) with respect to the Boc-Leu-Gly-Arg-pNA substrate in the presence of Et at high concentration was investigated. As a result, in the samples containing recombinant Pro-CE and/or recombinant factor B, activation attributed to high concentration Et was not observed. In contrast, remarkable hydrolysis activity was observed in a sample containing recombinant factor C and in the complete reconstitution system containing recombinant factors C and B and recombinant Pro-CE. However, the hydrolysis activity induced in the complete reconstitution system containing recombinant Pro-CE, recombinant B, and recombinant C was remarkably high (about some $10^3$) as compared with that induced in the sample containing only recombinant factor C (FIG. 11).

Figure 10:
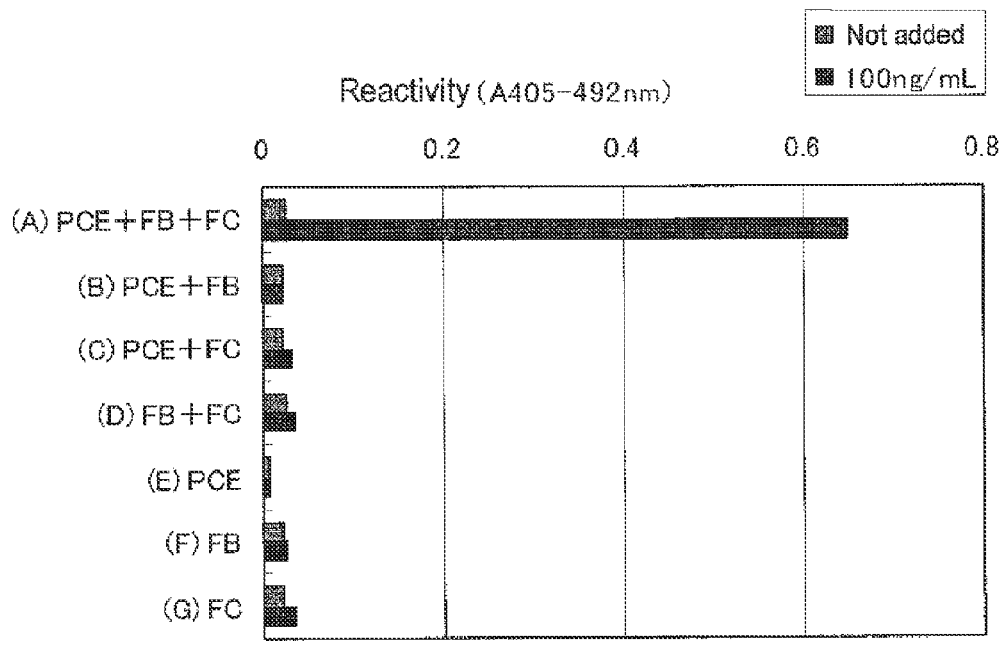
FIG. 10 depicts the results of the detection of an Et reaction in a complete reconstitution system containing recombinant Pro-CE, recombinant factor B and recombinant factor C; the graph depicts the Et reactivity of the samples, tested with and without Et.
Figure 11:
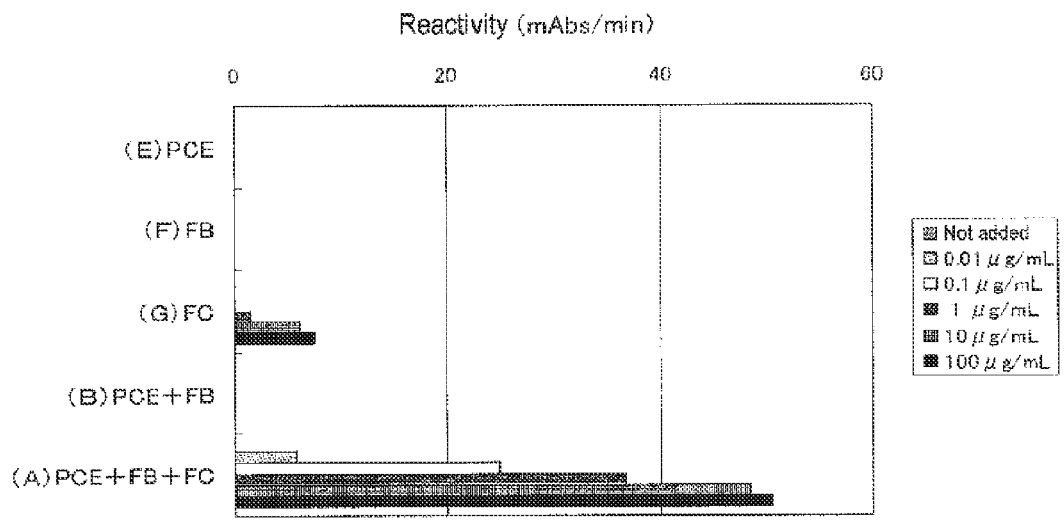
FIG. 11 depicts a graph showing the hydrolysis performance of factors A, B and E-G with respect to a Boc-LGR-pNA substrate in the presence of different concentrations of Et.

As is clear from Table 6 and FIGS. 10 and 11, similar to the case of a native factor contained in amebocyte lysate (native factor LAL), cascade reaction of Et proceeds in a concentration-dependent manner through employment of recombinant factors C and B and recombinant Pro-CE in combination. Also, even when a different *limulus*-derived clotting factor is employed for reconstitution of the cascade, the same enzymatic activity as that of native factor LAL was found to be expressed.

Example 5

Effect of Metal Salt on et Reaction Activity of a Complete Reconstitution System In Et reaction in the complete reconstitution system (sample A) shown in Example 4, effects of variation amount of metal salt on Et reaction activity was investigated.
(A) Effect of Magnesium Sulfate (No Calcium Chloride or Sodium Chloride was Added)
(a) In a Concentration Range of 0 to 100 mM In Example 5, the magnesium sulfate concentration in Et reaction in the complete reconstitution system of Example 4, which was 64 mM, was changed within the range of 0 to 100 mM, and the change in reaction activity was observed (during reaction). The results are shown in Table 7 and FIG. 12. In the reaction, an Et solution of 0 ng/mL (control) and that of 100 ng/mL were employed.

TABLE 7

| Et concentration (ng/mL) | NaCl concentration (mM: during reaction) | Reactivity (mAbs/min) | | Av. |
|---|---|---|---|---|
| 0 | 0 | 0.21 | — | 0.21 |
|  | 6.25 | 0.22 | — | 0.22 |
|  | 12.5 | 0.21 | — | 0.21 |
|  | 25 | 0.21 | — | 0.21 |
|  | 50 | 0.20 | — | 0.20 |
|  | 100 | 0.19 | — | 0.19 |
|  | 200 | 0.14 | — | 0.14 |
| 20 | 0 | 27.07 | 27.50 | 27.29 |
|  | 6.25 | 25.83 | 25.79 | 25.81 |
|  | 12.5 | 28.30 | 29.32 | 28.81 |
|  | 25 | 28.18 | 28.65 | 28.42 |
|  | 50 | 27.27 | 27.96 | 27.62 |
|  | 100 | 21.79 | 21.46 | 21.63 |
|  | 200 | 17.66 | 18.42 | 18.04 |

Figure 12:
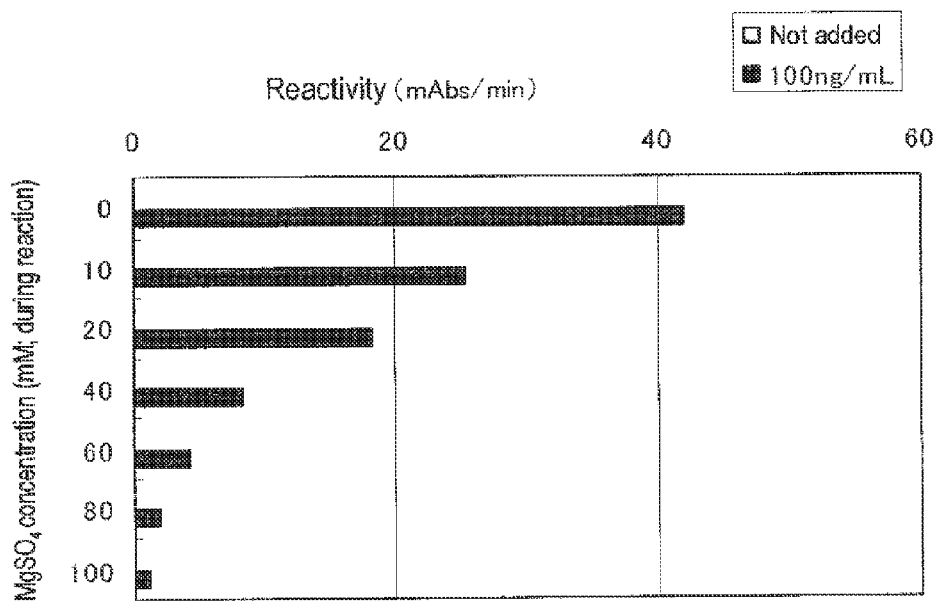
FIG. 12 depicts a graph showing the effect of magnesium sulfate concentration (0 to 100 mM) on the Et reaction in a complete reconstitution system, tested with and without Et.

As is clear from Table 7 and FIG. 12, in the complete reconstitution system of the method 1 of the present invention, the reactivity value significantly decreased in response to the increase in concentration of magnesium sulfate added to the measurement system.

(b) In a Concentration Range of 0 to 10 mM

In the reaction system (a) of the Example (Et concentration: 0 ng/mL (control) or 20 ng/mL), the magnesium sulfate concentration was changed to 0 to 10 mM during reaction, and change in activity was observed after reconstitution. The results are shown in Table 8 and FIG. 13.

TABLE 8

| Et concentration (ng/mL) | MgSO$_4$ concentration (mM: during reaction) | Reactivity (mAbs/min) | | Av. |
|---|---|---|---|---|
| 0 | 0 | 0.11 | — | 0.11 |
|  | 1 | 0.10 | — | 0.10 |
|  | 2 | 0.08 | — | 0.08 |
|  | 4 | 0.08 | — | 0.08 |
|  | 6 | 0.09 | — | 0.09 |
|  | 8 | 0.08 | — | 0.08 |
|  | 10 | 0.09 | — | 0.09 |
| 20 | 0 | 24.03 | 23.96 | 24.00 |
|  | 1 | 22.33 | 22.42 | 22.38 |
|  | 2 | 21.53 | 22.88 | 22.21 |
|  | 4 | 20.22 | 19.59 | 19.91 |
|  | 6 | 18.70 | 18.40 | 18.55 |
|  | 8 | 15.33 | 15.78 | 15.56 |
|  | 10 | 14.44 | 14.57 | 14.51 |

Figure 13:
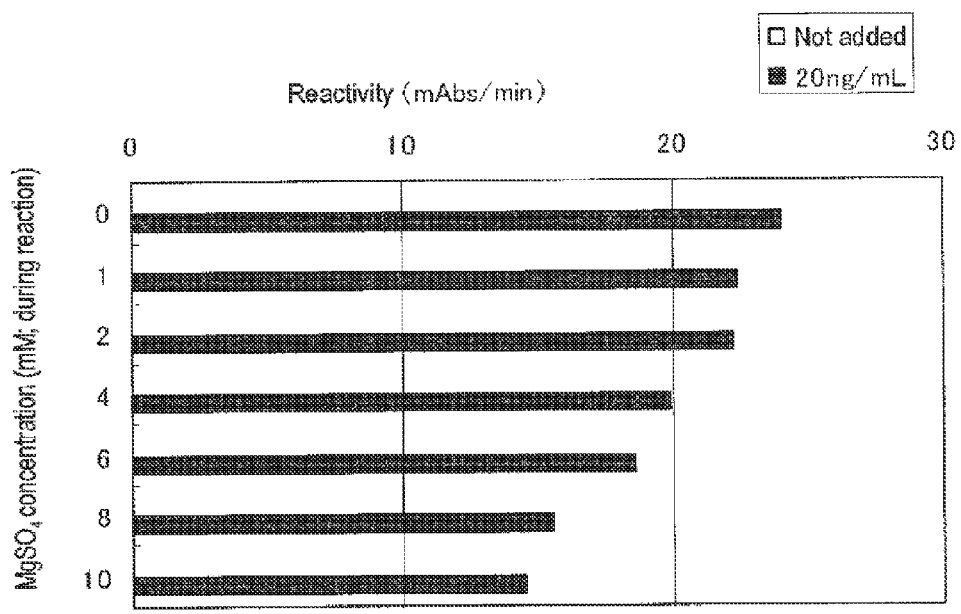
FIG. 13 depicts a graph showing the effect of magnesium sulfate concentration (0 to 10 mM) on the Et reaction in a complete reconstitution system, tested with and without Et.

As is clear from Table 8 and FIG. 13, in the complete reconstitution system of the method 1 of the present invention, even when the magnesium sulfate concentration was 10 mM or lower, Et reaction was suppressed in a concentration-dependent manner.

Thus, in Et reaction in the measurement system, activity of the factors can be clearly detected and maintained after reconstitution, even when no magnesium sulfate was added.

(B) Effects of Calcium Chloride (No Magnesium Sulfate or Sodium Chloride was Added)

In Et reaction in the complete reconstitution system of Example 4 (Et concentration: 0 (control) or 20 ng/mL), the calcium chloride concentration was changed to 0 to 5 mM during reaction, and change in activity was observed after reconstitution. The results are shown in Table 9 and FIG. 14.

TABLE 9

| Et concentration (ng/mL) | CaCl$_2$ concentration (mM: during reaction) | Reactivity (mAbs/min) | | Av. |
|---|---|---|---|---|
| 0 | 0 | 0.06 | — | 0.06 |
|  | 0.5 | 0.03 | — | 0.03 |
|  | 1 | 0.13 | — | 0.13 |
|  | 2 | 0.36 | — | 0.36 |
|  | 3 | 0.64 | — | 0.64 |
|  | 4 | 0.73 | — | 0.73 |
|  | 5 | 0.71 | — | 0.71 |
| 20 | 0 | 30.83 | 31.02 | 30.93 |
|  | 0.5 | 21.66 | 22.79 | 22.23 |
|  | 1 | 17.53 | 20.01 | 18.77 |
|  | 2 | 14.09 | 14.60 | 14.35 |
|  | 3 | 11.78 | 12.96 | 12.37 |
|  | 4 | 9.88 | 10.04 | 9.96 |
|  | 5 | 9.15 | 10.04 | 9.60 |

(Slightly turbid at a CaCl$_2$ concentration of 1 to 5 mM)

Figure 14:
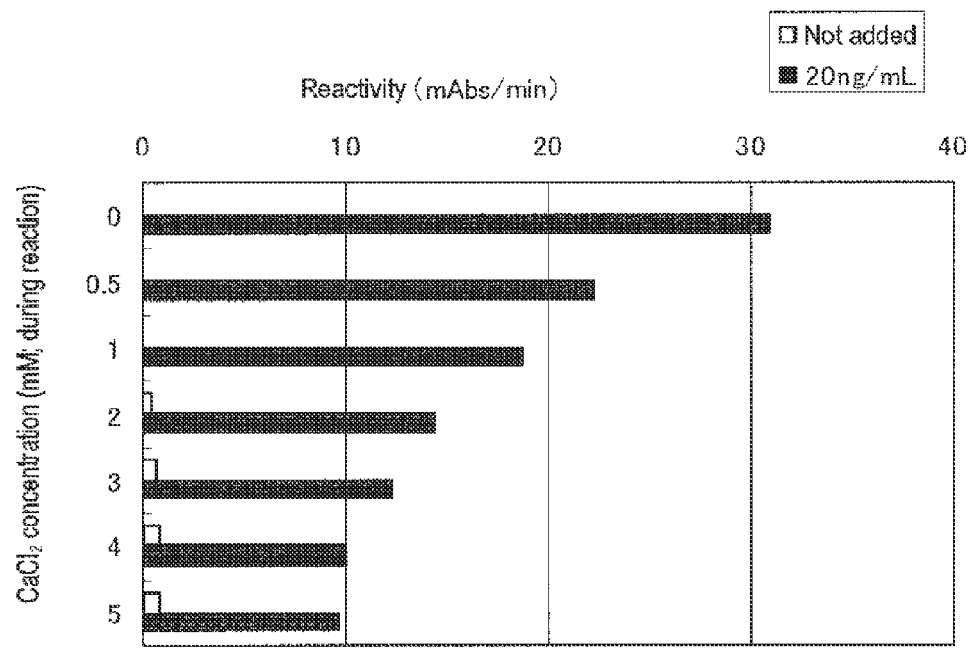
FIG. 14 depicts a graph showing the effect of calcium chloride concentration (0 to 5 mM) on the Et reaction in a complete reconstitution system, tested with and without Et.

As is clear from Table 9 and FIG. 14, in Et reaction in the complete reconstitution system, activity of the factors can be clearly detected and maintained after reconstitution, even when no calcium chloride was added. The feature is similar to the case of addition of a magnesium salt.

(C) Effects of Sodium Chloride (No Magnesium Sulfate or Calcium Chloride was Added)

In the experiment system, Cl$^-$ was present at a concentration of 80 mM in reaction buffer (Tris-Cl, pH=8.0) during reaction. However, since Na$^+$ was absent in the experiment system, the buffer-derived Cl$^-$ was not included in the sodium chloride concentration.

In Et reaction in the complete reconstitution system of Example 4, Et concentration was 0 (control) or 20 ng/mL). In Example 5, the calcium chloride concentration, which was 150 mM in Example 4, was changed in the range of 0 to 2.5 M (0, 0.078, 0.156, 0.313, 0.625, 1.25, and 2.5 (M)), and change in reactivity value was observed (during reaction). The results are shown in Table 10 and FIG. 15.

TABLE 10

| Et concentration (ng/mL) | NaCl concentration (mM: during reaction) | Reactivity (mAbs/min) | | Av. |
|---|---|---|---|---|
| 0 | 0 | 0.21 | — | 0.21 |
|  | 6.25 | 0.22 | — | 0.22 |
|  | 12.5 | 0.21 | — | 0.21 |
|  | 25 | 0.21 | — | 0.21 |
|  | 50 | 0.20 | — | 0.20 |
|  | 100 | 0.19 | — | 0.19 |
|  | 200 | 0.14 | — | 0.14 |
| 20 | 0 | 27.07 | 27.50 | 27.29 |
|  | 6.25 | 25.83 | 25.79 | 25.81 |
|  | 12.5 | 28.30 | 29.32 | 28.81 |
|  | 25 | 28.18 | 28.65 | 28.42 |
|  | 50 | 27.27 | 27.96 | 27.62 |
|  | 100 | 21.79 | 21.46 | 21.63 |
|  | 200 | 17.66 | 18.42 | 18.04 |

Figure 15:
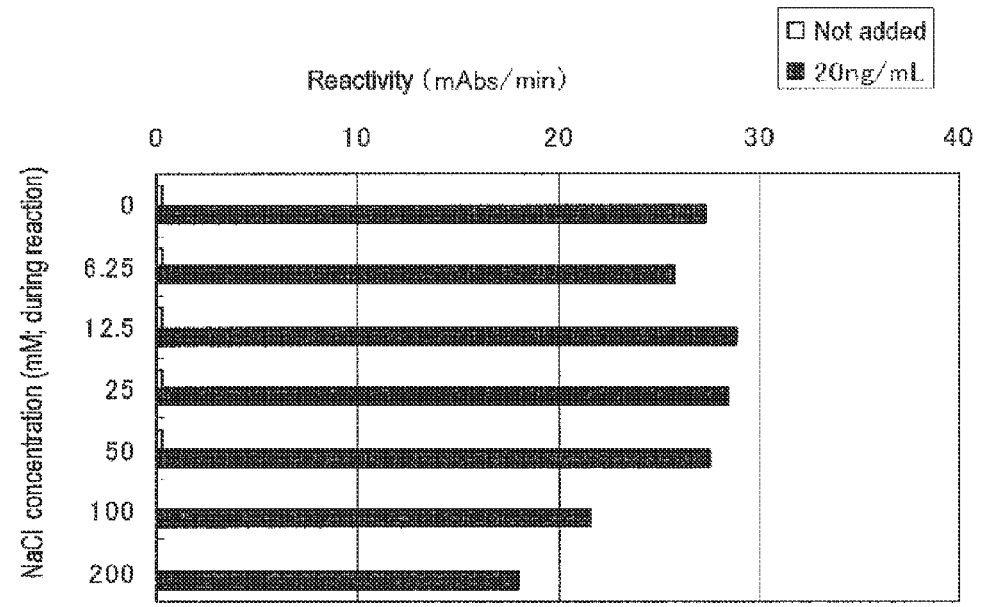
FIG. 15 depicts a graph showing the effect of sodium chloride concentration (0 to 2.5 M) on the Et reaction in a complete reconstitution system, tested with and without Et.

As is clear from Table 10 and FIG. 15, when the sodium chloride concentration during reaction was 0 to 50 mM, virtually no effect was observed on activity after reconstitution. However, when the concentration was higher, reaction was significantly suppressed (reduction by about 30% at 200 mM).

Example 6

Substrate Specificity of Et Reaction in the Complete Reconstitution System

In Example 6, a synthetic chromogenic substrate Boc-Val-Pro-Arg-pNA (Boc-VPR-pNA) (acetate salt) (hereinafter referred to as substrate 1)—similar to a synthetic fluorescent substrate contained in an Et assay reagent (PyroGene, product of Cambrex) containing recombinant factor C as an essential component (Boc-Val-Pro-Arg-MCA)—was employed. Comparison in terms of Et reaction in the complete reconstitution system of Example 4 was made to Boc-Leu-Gly-Arg-pNA (Boc-LGR-pNA) (hereinafter referred to as substrate 2), which is an optimum substrate in conventional LAL reaction.

The each substrate (1 or 2) concentration in Et reaction was predetermined to 0.3 mM.

Figure 16:
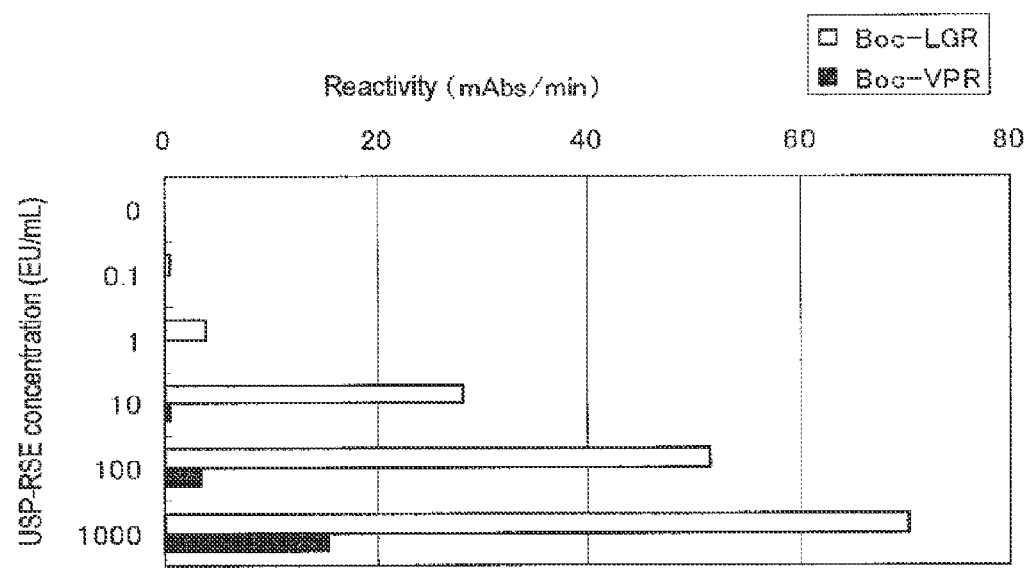
FIG. 16 depicts a graph showing Et reactivity in a complete reconstitution system investigated through a test employing Boc-VPR-pNA or Boc-LGR-pNA as a substrate.

Table 11 and FIG. 16 show the results.

TABLE 11

| Substrate | Et concentration (EU/mL) | Reactivity (mAbs/min) | | Av. |
|---|---|---|---|---|
| Boc-LGR-pNA | 0 | 0.10 | 0.09 | 0.10 |
| | 0.1 | 0.47 | 0.45 | 0.46 |
| | 1 | 3.87 | 3.76 | 3.82 |
| | 10 | 28.61 | 27.90 | 28.26 |
| | 100 | 50.71 | 52.37 | 51.54 |
| | 1000 | 70.48 | 70.23 | 70.36 |
| Boc-VPR-pNA | 0 | 0.11 | 0.09 | 0.10 |
| | 0.1 | 0.12 | 0.11 | 0.12 |
| | 1 | 0.12 | 0.14 | 0.13 |
| | 10 | 0.45 | 0.48 | 0.47 |
| | 100 | 3.54 | 3.34 | 3.44 |
| | 1000 | 15.46 | 15.30 | 15.38 |

As is clear from Table 11 and FIG. 16, Et activity in the complete reconstitution system is about 200 times higher in the case of Boc-Leu-Gly-Arg-pNA (substrate 2) than that in the case of Boc-Val-Pro-Arg-pNA (substrate 1).

In an additional experiment, Et reaction in the system only containing recombinant factor C (substrate concentration: 0.3 mM (substrates 1 and 2) was investigated. As a result, reactivity value when substrate 1 was used was about 1.6 times higher than that when substrate 2 was used.

Therefore, as compared with use of recombinant factor C alone, a complete reconstitution system exhibits remarkably high reactivity (Et activity). Those skilled in the art readily understand that the same tendency may be observed when Et is changed to (1→3)-β-D-glucan. Thus, according to the present invention, detection and determination of endotoxin and (1→3)-β-D-glucan at high sensitivity and high reproducibility can be realized, even when the assay target is present in a small amount.

INDUSTRIAL APPLICABILITY

The present invention provides an in vitro tool and a method for genetically mass-producing a *limulus*-derived Pro-CE or for detecting and determining a bacterial component derived from a microorganism at high efficiency and reproducibility. The Pro-CE produced according to the present invention serves as a main factor forming, with another recombinant factor relating to LAL reaction, a reaction system. On the basis of detection and assay of an Et and BG, the method of the present invention finds a wide range of non-temporary uses, safety evaluation of pharmaceutical products and medical tools; serum diagnosis of sepsis, fungal infections, etc.; tools for detecting microorganism contamination in environmental and food hygiene fields; reagents for use in research fields.

The invention claimed is:

1. A method of detecting an endotoxin in a sample, comprising the steps of (a) to (c):
   (a) mixing the components of (1)-(3), the sample, and the substrate, to produce a detection mixture, wherein no magnesium salts are added to said mixture:
   (1) a recombinant pro-clotting enzyme, wherein said recombinant pro-clotting enzyme is produced by a method comprising: growing an insect cell harboring a baculovirus, wherein said baculovirus harbors a DNA fragment encoding a protein comprising the amino acid sequence of SEQ ID NO: 4; and collecting pro-clotting enzyme from said grown insect cell;
   (2) recombinant factor C, wherein the recombinant factor C has the same sequence as factor C produced by a horseshoe crab selected from the group consisting of *Tachypleus tridentatus, Limulus polyphemus, Tachypleus gigas*, and *Tachypleus rotundicauda*; and
   (3) recombinant factor B, wherein the recombinant factor B has the same sequence as factor B produced by a horseshoe crab selected from the group consisting of *Tachypleus tridentatus, Limulus polyphemus, Tachypleus gigas*, and *Tachypleus rotundicauda*,
   (b) quantitatively or qualitatively detecting an enzymatic activity in said mixture, said enzymatic activity having been induced through conversion of said recombinant pro-clotting enzyme to a clotting enzyme, and wherein said detection uses the color of a synthetic chromogenic substrate as a signal, said synthetic chromogenic substrate being Boc-Leu-Gly-Arg-pNA, and
   (c) detecting endotoxin in the sample by using said detected enzymatic activity as an index of the existing amount or the existence of endotoxin in the sample.

2. The method according to claim 1, wherein said DNA fragment comprises the nucleotide sequence of nucleotides 1 to 1143 of SEQ ID NO: 3.

3. The method according to claim 1, wherein the baculovirus is nuclear polyhedrosis virus.

4. The method according to claim 1, wherein calcium chloride is not added to said mixture.

5. The method according to claim 1, wherein, in production of the recombinant factor B, MOI (Multiplicity of Infection) is about 0.1 and the period of culture at 28° C. is about 96 hours when the insect cell is infected with the baculovirus DNA fragment to which the gene coding factor B is introduced and culture supernatant of the baculovirus-infected insect cell is obtained.

* * * * *

SEQUENCE LISTING

<160> NUMBER OF SEQ ID NOS: 22

<210> SEQ ID NO 1
<211> LENGTH: 1501
<212> TYPE: DNA
<213> ORGANISM: Tachypleus tridentatus
<220> FEATURE:
<221> NAME/KEY: CDS
<222> LOCATION: (217)..(1344)

<400> SEQUENCE: 1

```
gcaatacagg ctacaaacat ctcatcagac gcattacctg gttgtttaat tccgcgaaag      60
cttcacgaga acaagtcaaa cttagcttgt ggtcccgcga ctgactgcct ggaaagtagt     120
tcccaaaatt gcggctttat aaatcaacct aaacaaaacc gtcctgaaac tttaccgttc     180
cacatccacc gaggtagccg ggtcgtcctc agcagt atg ttg gtg aat aac gtg      234
                                        Met Leu Val Asn Asn Val
                                        1               5 ttt tca cta ctg tgt ttc cca ctc ttg atg tct gtg gtt aga tgc agt      282
Phe Ser Leu Leu Cys Phe Pro Leu Leu Met Ser Val Val Arg Cys Ser
            10                  15                  20 act ctc agc aga cag cgt aga cag ttt gtt ttc cct gac gag gaa gaa      330
Thr Leu Ser Arg Gln Arg Arg Gln Phe Val Phe Pro Asp Glu Glu Glu
        25                  30                  35 ctt tgc tca aac cga ttt act gaa gaa gga aca tgc aaa aat gtc ttg      378
Leu Cys Ser Asn Arg Phe Thr Glu Glu Gly Thr Cys Lys Asn Val Leu
    40                  45                  50 gat tgt aga ata ctt tta caa aaa aat gat tat aat tta ctc aaa gaa      426
Asp Cys Arg Ile Leu Leu Gln Lys Asn Asp Tyr Asn Leu Leu Lys Glu
55                  60                  65                  70 tca ata tgc ggc ttt gaa ggc ata aca ccc aaa gtt tgt tgt ccg aaa      474
Ser Ile Cys Gly Phe Glu Gly Ile Thr Pro Lys Val Cys Cys Pro Lys
                75                  80                  85
```

```
tca agc cat gta att tca agt aca cag gca cct cca gaa acc act acg    522
Ser Ser His Val Ile Ser Ser Thr Gln Ala Pro Pro Glu Thr Thr Thr
         90              95                 100 act gaa cgc cca cca aaa cag ata cca ccc aat ctt cct gaa gtg tgt    570
Thr Glu Arg Pro Pro Lys Gln Ile Pro Pro Asn Leu Pro Glu Val Cys
        105             110                 115 gga att cac aat act aca act acc agg att att gga ggt cgg gaa gca    618
Gly Ile His Asn Thr Thr Thr Thr Arg Ile Ile Gly Gly Arg Glu Ala
        120             125                 130 cct att gga gcc tgg ccg tgg atg act gct gtc tac ata aaa caa gga    666
Pro Ile Gly Ala Trp Pro Trp Met Thr Ala Val Tyr Ile Lys Gln Gly
135             140             145                 150 gga atc aga agt gtt cag tgt ggt ggc gca ctt gtc act aac agg cac    714
Gly Ile Arg Ser Val Gln Cys Gly Gly Ala Leu Val Thr Asn Arg His
            155             160                 165 gtg att aca gct tcg cac tgt gtt gta aac agt gca gga aca gat gtg    762
Val Ile Thr Ala Ser His Cys Val Val Asn Ser Ala Gly Thr Asp Val
            170             175                 180 atg cca gct gat gta ttc tcg gtt cgt ctg ggt gaa cac aat tta tac    810
Met Pro Ala Asp Val Phe Ser Val Arg Leu Gly Glu His Asn Leu Tyr
            185             190                 195 agt acc gat gac gat tcg aat cca ata gat ttt gca gtt acg tcg gtg    858
Ser Thr Asp Asp Asp Ser Asn Pro Ile Asp Phe Ala Val Thr Ser Val
200                 205                 210 aaa cat cac gaa cac ttt gta ctc gcg acg tat ttg aat gac atc gca    906
Lys His His Glu His Phe Val Leu Ala Thr Tyr Leu Asn Asp Ile Ala
215             220                 225                 230 att cta acg tta aat gac aca gtt acg ttt aca gac aga att cga ccc    954
Ile Leu Thr Leu Asn Asp Thr Val Thr Phe Thr Asp Arg Ile Arg Pro
                235                 240                 245 att tgt cta cct tat cgt aag ttg aga tac gat gat cta gca atg aga   1002
Ile Cys Leu Pro Tyr Arg Lys Leu Arg Tyr Asp Asp Leu Ala Met Arg
            250                 255                 260 aaa ccg ttt atc act gga tgg gga aca aca gca ttt aac ggc cca tct   1050
Lys Pro Phe Ile Thr Gly Trp Gly Thr Thr Ala Phe Asn Gly Pro Ser
            265                 270                 275 agt gca gtg ttg aga gaa gta cag tta cca ata tgg gaa cac gag gcc   1098
Ser Ala Val Leu Arg Glu Val Gln Leu Pro Ile Trp Glu His Glu Ala
        280                 285                 290 tgt aga cag gcc tac gag aag gat tta aat att aca aac gtg tat atg   1146
Cys Arg Gln Ala Tyr Glu Lys Asp Leu Asn Ile Thr Asn Val Tyr Met
295                 300                 305                 310 tgt gct ggc ttt gca gat ggc ggg aag gat gct tgc cag ggt gat tct   1194
Cys Ala Gly Phe Ala Asp Gly Gly Lys Asp Ala Cys Gln Gly Asp Ser
                315                 320                 325 gga ggt cca atg atg ttg cct gtt aaa acc gga gag ttt tat ctc att   1242
Gly Gly Pro Met Met Leu Pro Val Lys Thr Gly Glu Phe Tyr Leu Ile
            330                 335                 340 gga att gtg tct ttc gga aag aaa tgc gca ttg cct gga ttt cct ggg   1290
Gly Ile Val Ser Phe Gly Lys Lys Cys Ala Leu Pro Gly Phe Pro Gly
            345                 350                 355 gtt tac aca aaa gtg aca gag ttt tta gat tgg att gca gaa cat atg   1338
Val Tyr Thr Lys Val Thr Glu Phe Leu Asp Trp Ile Ala Glu His Met
        360                 365                 370 gtg tag actaaagctg tgaatgactc catttcgaat atttaaccca tactcgcctg    1394
Val
375 tagcaaaacg actgaagaat caagcagggg acaaaaccaa cttttttttt tttttttctt  1454 caatagttct accatgtatt gaaaaccaac ataagacaat caaataa                1501
```

<210> SEQ ID NO 2
<211> LENGTH: 375
<212> TYPE: PRT
<213> ORGANISM: Tachypleus tridentatus

<400> SEQUENCE: 2

```
Met Leu Val Asn Asn Val Phe Ser Leu Leu Cys Phe Pro Leu Leu Met
1               5                   10                  15

Ser Val Val Arg Cys Ser Thr Leu Ser Arg Gln Arg Gln Phe Val
            20                  25                  30

Phe Pro Asp Glu Glu Leu Cys Ser Asn Arg Phe Thr Glu Gly
            35                  40                  45

Thr Cys Lys Asn Val Leu Asp Cys Arg Ile Leu Leu Gln Lys Asn Asp
    50                  55                  60

Tyr Asn Leu Leu Lys Glu Ser Ile Cys Gly Phe Glu Gly Ile Thr Pro
65                  70                  75                  80

Lys Val Cys Cys Pro Lys Ser Ser His Val Ile Ser Ser Thr Gln Ala
                85                  90                  95

Pro Pro Glu Thr Thr Thr Thr Glu Arg Pro Pro Lys Gln Ile Pro Pro
            100                 105                 110

Asn Leu Pro Glu Val Cys Gly Ile His Asn Thr Thr Thr Arg Ile
            115                 120                 125

Ile Gly Gly Arg Glu Ala Pro Ile Gly Ala Trp Pro Trp Met Thr Ala
            130                 135                 140

Val Tyr Ile Lys Gln Gly Gly Ile Arg Ser Val Gln Cys Gly Gly Ala
145                 150                 155                 160

Leu Val Thr Asn Arg His Val Ile Thr Ala Ser His Cys Val Val Asn
                165                 170                 175

Ser Ala Gly Thr Asp Val Met Pro Ala Asp Val Phe Ser Val Arg Leu
            180                 185                 190

Gly Glu His Asn Leu Tyr Ser Thr Asp Asp Ser Asn Pro Ile Asp
            195                 200                 205

Phe Ala Val Thr Ser Val Lys His His Glu His Phe Val Leu Ala Thr
            210                 215                 220

Tyr Leu Asn Asp Ile Ala Ile Leu Thr Leu Asn Asp Thr Val Thr Phe
225                 230                 235                 240

Thr Asp Arg Ile Arg Pro Ile Cys Leu Pro Tyr Arg Lys Leu Arg Tyr
                245                 250                 255

Asp Asp Leu Ala Met Arg Lys Pro Phe Ile Thr Gly Trp Gly Thr Thr
            260                 265                 270

Ala Phe Asn Gly Pro Ser Ser Ala Val Leu Arg Glu Val Gln Leu Pro
            275                 280                 285

Ile Trp Glu His Glu Ala Cys Arg Gln Ala Tyr Glu Lys Asp Leu Asn
            290                 295                 300

Ile Thr Asn Val Tyr Met Cys Ala Gly Phe Ala Asp Gly Gly Lys Asp
305                 310                 315                 320

Ala Cys Gln Gly Asp Ser Gly Gly Pro Met Met Leu Pro Val Lys Thr
                325                 330                 335

Gly Glu Phe Tyr Leu Ile Gly Ile Val Ser Phe Gly Lys Lys Cys Ala
            340                 345                 350

Leu Pro Gly Phe Pro Gly Val Tyr Thr Lys Val Thr Glu Phe Leu Asp
            355                 360                 365

Trp Ile Ala Glu His Met Val
```

<210> SEQ ID NO 3
<211> LENGTH: 1146
<212> TYPE: DNA
<213> ORGANISM: Tachypleus tridentatus
<220> FEATURE:
<221> NAME/KEY: CDS
<222> LOCATION: (1)..(1143)

<400> SEQUENCE: 3

| | | | | | | | | | | | | | | | | |
|---|---|---|---|---|---|---|---|---|---|---|---|---|---|---|---|---|
| atg | ttg | gtg | aat | aac | gtg | ttt | tca | cta | ctg | tgt | ttc | cca | ctc | ttg | atg | 48 |
| Met | Leu | Val | Asn | Asn | Val | Phe | Ser | Leu | Leu | Cys | Phe | Pro | Leu | Leu | Met | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| tct | gtg | gtt | aga | tgc | agt | act | ctc | agc | aga | cag | cgt | aga | cag | ttt | gtt | 96 |
| Ser | Val | Val | Arg | Cys | Ser | Thr | Leu | Ser | Arg | Gln | Arg | Arg | Gln | Phe | Val | |
| | | | 20 | | | | | 25 | | | | | 30 | | | |

| | | | | | | | | | | | | | | | | |
|---|---|---|---|---|---|---|---|---|---|---|---|---|---|---|---|---|
| ttc | cct | gac | gag | gaa | gaa | ctt | tgc | tca | aac | cga | ttt | act | gaa | gaa | gga | 144 |
| Phe | Pro | Asp | Glu | Glu | Glu | Leu | Cys | Ser | Asn | Arg | Phe | Thr | Glu | Glu | Gly | |
| | | | | 35 | | | | | 40 | | | | | 45 | | |

| | | | | | | | | | | | | | | | | |
|---|---|---|---|---|---|---|---|---|---|---|---|---|---|---|---|---|
| aca | tgc | aaa | aat | gtc | ttg | gat | tgt | aga | ata | ctt | tta | caa | aaa | aat | gat | 192 |
| Thr | Cys | Lys | Asn | Val | Leu | Asp | Cys | Arg | Ile | Leu | Leu | Gln | Lys | Asn | Asp | |
| 50 | | | | | 55 | | | | | 60 | | | | | | |

| | | | | | | | | | | | | | | | | |
|---|---|---|---|---|---|---|---|---|---|---|---|---|---|---|---|---|
| tat | aat | tta | ctc | aaa | gaa | tca | ata | tgc | ggc | ttt | gaa | ggc | ata | aca | ccc | 240 |
| Tyr | Asn | Leu | Leu | Lys | Glu | Ser | Ile | Cys | Gly | Phe | Glu | Gly | Ile | Thr | Pro | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| aaa | gtt | tgt | tgt | ccg | aaa | tca | agc | cat | gta | att | tca | agt | aca | cag | gca | 288 |
| Lys | Val | Cys | Cys | Pro | Lys | Ser | Ser | His | Val | Ile | Ser | Ser | Thr | Gln | Ala | |
| | | | | 85 | | | | | 90 | | | | | 95 | | |

| | | | | | | | | | | | | | | | | |
|---|---|---|---|---|---|---|---|---|---|---|---|---|---|---|---|---|
| cct | cca | gaa | acc | act | acg | act | gaa | cgc | cca | cca | aaa | cag | ata | cca | ccc | 336 |
| Pro | Pro | Glu | Thr | Thr | Thr | Thr | Glu | Arg | Pro | Pro | Lys | Gln | Ile | Pro | Pro | |
| | | | | 100 | | | | | 105 | | | | | 110 | | |

| | | | | | | | | | | | | | | | | |
|---|---|---|---|---|---|---|---|---|---|---|---|---|---|---|---|---|
| aat | ctt | cct | gaa | gtg | tgt | gga | att | cac | aat | act | aca | act | acc | agg | att | 384 |
| Asn | Leu | Pro | Glu | Val | Cys | Gly | Ile | His | Asn | Thr | Thr | Thr | Thr | Arg | Ile | |
| | | 115 | | | | | 120 | | | | | 125 | | | | |

| | | | | | | | | | | | | | | | | |
|---|---|---|---|---|---|---|---|---|---|---|---|---|---|---|---|---|
| att | gga | ggt | cgg | gaa | gca | cct | att | gga | gcc | tgg | ccg | tgg | atg | act | gct | 432 |
| Ile | Gly | Gly | Arg | Glu | Ala | Pro | Ile | Gly | Ala | Trp | Pro | Trp | Met | Thr | Ala | |
| 130 | | | | | 135 | | | | | 140 | | | | | | |

| | | | | | | | | | | | | | | | | |
|---|---|---|---|---|---|---|---|---|---|---|---|---|---|---|---|---|
| gtc | tac | ata | aaa | caa | gga | gga | atc | aga | agt | gtt | cag | tgt | ggt | ggc | gca | 480 |
| Val | Tyr | Ile | Lys | Gln | Gly | Gly | Ile | Arg | Ser | Val | Gln | Cys | Gly | Gly | Ala | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| ctt | gtc | act | aac | agg | cac | gtg | att | aca | gct | tcg | cac | tgt | gtt | gta | aac | 528 |
| Leu | Val | Thr | Asn | Arg | His | Val | Ile | Thr | Ala | Ser | His | Cys | Val | Val | Asn | |
| | | | | 165 | | | | | 170 | | | | | 175 | | |

| | | | | | | | | | | | | | | | | |
|---|---|---|---|---|---|---|---|---|---|---|---|---|---|---|---|---|
| agt | gca | gga | aca | gat | gtg | atg | cca | gct | gat | gta | ttc | tcg | gtt | cgt | ctg | 576 |
| Ser | Ala | Gly | Thr | Asp | Val | Met | Pro | Ala | Asp | Val | Phe | Ser | Val | Arg | Leu | |
| | | | 180 | | | | | 185 | | | | | 190 | | | |

| | | | | | | | | | | | | | | | | |
|---|---|---|---|---|---|---|---|---|---|---|---|---|---|---|---|---|
| ggt | gaa | cac | aat | tta | tac | agt | acc | gat | gac | gat | tcg | aat | cca | ata | gat | 624 |
| Gly | Glu | His | Asn | Leu | Tyr | Ser | Thr | Asp | Asp | Asp | Ser | Asn | Pro | Ile | Asp | |
| | | 195 | | | | | 200 | | | | | 205 | | | | |

| | | | | | | | | | | | | | | | | |
|---|---|---|---|---|---|---|---|---|---|---|---|---|---|---|---|---|
| ttt | gca | gtt | acg | tcg | gtg | aaa | cat | cac | gaa | cac | ttt | gta | ctc | gcg | acg | 672 |
| Phe | Ala | Val | Thr | Ser | Val | Lys | His | His | Glu | His | Phe | Val | Leu | Ala | Thr | |
| 210 | | | | | 215 | | | | | 220 | | | | | | |

| | | | | | | | | | | | | | | | | |
|---|---|---|---|---|---|---|---|---|---|---|---|---|---|---|---|---|
| tat | ttg | aat | gac | atc | gca | att | cta | acg | tta | aat | gac | aca | gtt | acg | ttt | 720 |
| Tyr | Leu | Asn | Asp | Ile | Ala | Ile | Leu | Thr | Leu | Asn | Asp | Thr | Val | Thr | Phe | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| aca | gac | aga | att | cga | ccc | att | tgt | cta | cct | tat | cgt | aag | ttg | aga | tac | 768 |
| Thr | Asp | Arg | Ile | Arg | Pro | Ile | Cys | Leu | Pro | Tyr | Arg | Lys | Leu | Arg | Tyr | |
| | | | | 245 | | | | | 250 | | | | | 255 | | |

| | | | | | | | | | | | | | | | | |
|---|---|---|---|---|---|---|---|---|---|---|---|---|---|---|---|---|
| gat | gat | cta | gca | atg | aga | aaa | ccg | ttt | atc | act | gga | tgg | gga | aca | aca | 816 |
| Asp | Asp | Leu | Ala | Met | Arg | Lys | Pro | Phe | Ile | Thr | Gly | Trp | Gly | Thr | Thr | |

```
                 260                 265                 270
gca ttt aac ggc cca tct agt gca gtg ttg aga gaa gta cag tta cca        864
Ala Phe Asn Gly Pro Ser Ser Ala Val Leu Arg Glu Val Gln Leu Pro
        275                 280                 285 ata tgg gaa cac gag gcc tgt aga cag gcc tac gag aag gat tta aat        912
Ile Trp Glu His Glu Ala Cys Arg Gln Ala Tyr Glu Lys Asp Leu Asn
290                 295                 300 att aca aac gtg tat atg tgt gct ggc ttt gca gat ggc ggg aag gat        960
Ile Thr Asn Val Tyr Met Cys Ala Gly Phe Ala Asp Gly Gly Lys Asp
305                 310                 315                 320 gct tgc cag ggt gat tct gga ggt cca atg atg ttg cct gtt aaa acc       1008
Ala Cys Gln Gly Asp Ser Gly Gly Pro Met Met Leu Pro Val Lys Thr
                325                 330                 335 gga gag ttt tat ctc att gga att gtg tct ttc gga aag aaa tgc gca       1056
Gly Glu Phe Tyr Leu Ile Gly Ile Val Ser Phe Gly Lys Lys Cys Ala
            340                 345                 350 ttg cct gga ttt cct ggg gtt tac aca aaa gtg aca gag ttt tta gat       1104
Leu Pro Gly Phe Pro Gly Val Tyr Thr Lys Val Thr Glu Phe Leu Asp
        355                 360                 365 tgg att gca gaa cat atg gtg cat cac cat cac cat cac tag                1146
Trp Ile Ala Glu His Met Val His His His His His His
370                 375                 380

<210> SEQ ID NO 4
<211> LENGTH: 381
<212> TYPE: PRT
<213> ORGANISM: Tachypleus tridentatus

<400> SEQUENCE: 4

Met Leu Val Asn Asn Val Phe Ser Leu Leu Cys Phe Pro Leu Leu Met
1               5                   10                  15

Ser Val Val Arg Cys Ser Thr Leu Ser Arg Gln Arg Gln Phe Val
            20                  25                  30

Phe Pro Asp Glu Glu Leu Cys Ser Asn Arg Phe Thr Glu Glu Gly
        35                  40                  45

Thr Cys Lys Asn Val Leu Asp Cys Arg Ile Leu Leu Gln Lys Asn Asp
    50                  55                  60

Tyr Asn Leu Leu Lys Glu Ser Ile Cys Gly Phe Glu Gly Ile Thr Pro
65                  70                  75                  80

Lys Val Cys Cys Pro Lys Ser Ser His Val Ile Ser Ser Thr Gln Ala
                85                  90                  95

Pro Pro Glu Thr Thr Thr Thr Gly Arg Pro Pro Lys Gln Ile Pro Pro
            100                 105                 110

Asn Leu Pro Glu Val Cys Gly Ile His Asn Thr Thr Thr Arg Ile
        115                 120                 125

Ile Gly Gly Arg Glu Ala Pro Ile Gly Ala Trp Pro Trp Met Thr Ala
    130                 135                 140

Val Tyr Ile Lys Gln Gly Gly Ile Arg Ser Val Gln Cys Gly Gly Ala
145                 150                 155                 160

Leu Val Thr Asn Arg His Val Ile Thr Ala Ser His Cys Val Val Asn
                165                 170                 175

Ser Ala Gly Thr Asp Val Met Pro Ala Asp Val Phe Ser Val Arg Leu
            180                 185                 190

Gly Glu His Asn Leu Tyr Ser Thr Asp Asp Ser Asn Pro Ile Asp
        195                 200                 205

Phe Ala Val Thr Ser Val Lys His His Glu His Phe Val Leu Ala Thr
    210                 215                 220
```

-continued

Tyr Leu Asn Asp Ile Ala Ile Leu Thr Leu Asn Asp Thr Val Thr Phe
225                 230                 235                 240

Thr Asp Arg Ile Arg Pro Ile Cys Leu Pro Tyr Arg Lys Leu Arg Tyr
            245                 250                 255

Asp Asp Leu Ala Met Arg Lys Pro Phe Ile Thr Gly Trp Gly Thr Thr
        260                 265                 270

Ala Phe Asn Gly Pro Ser Ser Ala Val Leu Arg Glu Val Gln Leu Pro
    275                 280                 285

Ile Trp Glu His Glu Ala Cys Arg Gln Ala Tyr Glu Lys Asp Leu Asn
290                 295                 300

Ile Thr Asn Val Tyr Met Cys Ala Gly Phe Ala Asp Gly Gly Lys Asp
305                 310                 315                 320

Ala Cys Gln Gly Asp Ser Gly Gly Pro Met Met Leu Pro Val Lys Thr
            325                 330                 335

Gly Glu Phe Tyr Leu Ile Gly Ile Val Ser Phe Gly Lys Lys Cys Ala
        340                 345                 350

Leu Pro Gly Phe Pro Gly Val Tyr Thr Lys Val Thr Glu Phe Leu Asp
    355                 360                 365

Trp Ile Ala Glu His Met Val His His His His His
    370                 375                 380

<210> SEQ ID NO 5
<211> LENGTH: 26
<212> TYPE: DNA
<213> ORGANISM: Artificial
<220> FEATURE:
<223> OTHER INFORMATION: Primer for sequencing

<400> SEQUENCE: 5
tctagaatgt tggtgaataa cgtgtt                                       26

<210> SEQ ID NO 6
<211> LENGTH: 40
<212> TYPE: DNA
<213> ORGANISM: Artificial
<220> FEATURE:
<223> OTHER INFORMATION: Primer for sequencing

<400> SEQUENCE: 6
agatctagtg atggtgatgg tgatgcacca tatgttctgc                        40

<210> SEQ ID NO 7
<211> LENGTH: 18
<212> TYPE: DNA
<213> ORGANISM: Artificial
<220> FEATURE:
<223> OTHER INFORMATION: Primer for sequencing

<400> SEQUENCE: 7
tcacaaactg gaaatgtc                                                18

<210> SEQ ID NO 8
<211> LENGTH: 18
<212> TYPE: DNA
<213> ORGANISM: Artificial
<220> FEATURE:
<223> OTHER INFORMATION: Primer for sequencing

<400> SEQUENCE: 8
ccggaccagt gaacagag                                                18

<210> SEQ ID NO 9
<211> LENGTH: 20
<212> TYPE: DNA
<213> ORGANISM: Artificial
<220> FEATURE:
<223> OTHER INFORMATION: Primer for sequencing

<400> SEQUENCE: 9
aatcagaagt gttcagtgtg                                                 20

<210> SEQ ID NO 10
<211> LENGTH: 20
<212> TYPE: DNA
<213> ORGANISM: Artificial
<220> FEATURE:
<223> OTHER INFORMATION: Primer for sequencing

<400> SEQUENCE: 10
tcattcaaat acgtcgcgag                                                 20

<210> SEQ ID NO 11
<211> LENGTH: 21
<212> TYPE: DNA
<213> ORGANISM: Artificial
<220> FEATURE:
<223> OTHER INFORMATION: PCR Primer

<400> SEQUENCE: 11
gccattgtaa tgagacgcac a                                               21

<210> SEQ ID NO 12
<211> LENGTH: 23
<212> TYPE: DNA
<213> ORGANISM: Artificial
<220> FEATURE:
<223> OTHER INFORMATION: PCR Primer

<400> SEQUENCE: 12
cgtacaacaa ttgtctgtaa atc                                             23

<210> SEQ ID NO 13
<211> LENGTH: 21
<212> TYPE: DNA
<213> ORGANISM: Artificial
<220> FEATURE:
<223> OTHER INFORMATION: Primer for sequencing

<400> SEQUENCE: 13
tagttgctga tatcatggag a                                               21

<210> SEQ ID NO 14
<211> LENGTH: 18
<212> TYPE: DNA
<213> ORGANISM: Artificial
<220> FEATURE:
<223> OTHER INFORMATION: Primer for sequencing

<400> SEQUENCE: 14
tcacaaactg gaaatgtc                                                   18

<210> SEQ ID NO 15
<211> LENGTH: 1887
<212> TYPE: DNA
<213> ORGANISM: Tachypleus tridentatus
<220> FEATURE:
<221> NAME/KEY: CDS

<222> LOCATION: (143)..(1345)

<400> SEQUENCE: 15

```
gttgaatctt accggtaaga attagataac aaattttttaa aagttacact aacagaagct      60
ttttgacgtc agtatcttat atgtattacg tattcccaat ttaattggat cgttaacgcc     120
agacaactaa ccattttctg ga atg acg tgg ata tgt gtg ata acg ttg ttt     172
                         Met Thr Trp Ile Cys Val Ile Thr Leu Phe
                          1               5                    10 gct ctg gct tct gct acg ttg ggt aac aaa gtt agt aga gtg ggg gtc     220
Ala Leu Ala Ser Ala Thr Leu Gly Asn Lys Val Ser Arg Val Gly Val
             15                  20                  25 ctc ttc ccc aag aca cgg aac gac aat gag tgt aca gca aga ggg gga     268
Leu Phe Pro Lys Thr Arg Asn Asp Asn Glu Cys Thr Ala Arg Gly Gly
         30                  35                  40 ttg aaa gga tcc tgc aaa tcc ctc ata gac tgt cct agt gtc ttg gct     316
Leu Lys Gly Ser Cys Lys Ser Leu Ile Asp Cys Pro Ser Val Leu Ala
     45                  50                  55 acg ttg aag gac agt ttt cct gtc gtt tgc tct tgg aat ggt cga ttt     364
Thr Leu Lys Asp Ser Phe Pro Val Val Cys Ser Trp Asn Gly Arg Phe
 60                  65                  70 cag cct att gtc tgc tgt cct gat gca ata gca cca cca cct gta acc     412
Gln Pro Ile Val Cys Cys Pro Asp Ala Ile Ala Pro Pro Pro Val Thr
 75                  80                  85                  90 aca aca gct gta act gta ata tct aca aaa gaa cca aag ctt cca aga     460
Thr Thr Ala Val Thr Val Ile Ser Thr Lys Glu Pro Lys Leu Pro Arg
                 95                 100                 105 tta cat ata tca ggt tgt gga aaa aga aaa gtc aaa ata gat att aca     508
Leu His Ile Ser Gly Cys Gly Lys Arg Lys Val Lys Ile Asp Ile Thr
             110                 115                 120 act gtt gga cgc tct gga tca cca ata ctt cct ccg ata tct act cct     556
Thr Val Gly Arg Ser Gly Ser Pro Ile Leu Pro Pro Ile Ser Thr Pro
         125                 130                 135 caa aat tca aca ggt ggg aga gga att att gct gga ggc gta gaa gcc     604
Gln Asn Ser Thr Gly Gly Arg Gly Ile Ile Ala Gly Gly Val Glu Ala
     140                 145                 150 aaa att ggc gcg tgg cct tgg atg gca gct gtt ttt gtg aaa aac ttt     652
Lys Ile Gly Ala Trp Pro Trp Met Ala Ala Val Phe Val Lys Asn Phe
155                 160                 165                 170 ggc att ggc aga ttc cac tgt gct ggt agc ata atc agt aac aag tac     700
Gly Ile Gly Arg Phe His Cys Ala Gly Ser Ile Ile Ser Asn Lys Tyr
                 175                 180                 185 att ttg tca gct gcc cac gcc ttc ctt atc gga ggt cga aag ttg acc     748
Ile Leu Ser Ala Ala His Ala Phe Leu Ile Gly Gly Arg Lys Leu Thr
             190                 195                 200 cca act cgc tta gct gtc cgt gtg gga ggc cac tac ata aag agg ggt     796
Pro Thr Arg Leu Ala Val Arg Val Gly Gly His Tyr Ile Lys Arg Gly
         205                 210                 215 caa gag tat cca gtg aaa gac gtg att atc cat cct cat tat gta gaa     844
Gln Glu Tyr Pro Val Lys Asp Val Ile Ile His Pro His Tyr Val Glu
     220                 225                 230 aag gag aac tac aat gat ata gcc ata atc gag tta aaa gag gaa ctg     892
Lys Glu Asn Tyr Asn Asp Ile Ala Ile Ile Glu Leu Lys Glu Glu Leu
235                 240                 245                 250 aac ttt acg gac ttg gtc aat cct ata tgt ctc cct gat cca gag aca     940
Asn Phe Thr Asp Leu Val Asn Pro Ile Cys Leu Pro Asp Pro Glu Thr
                 255                 260                 265 gta acg gat cca tta aaa gac aga att gtg act gca gcg gga tgg ggc     988
Val Thr Asp Pro Leu Lys Asp Arg Ile Val Thr Ala Ala Gly Trp Gly
             270                 275                 280
```

```
gat ctg gat ttc tcc ggt cca cgg agc caa gtt cta cgt gag gta agc    1036
Asp Leu Asp Phe Ser Gly Pro Arg Ser Gln Val Leu Arg Glu Val Ser
        285                 290                 295 atc cca gtt gtt cca gtt gat aaa tgt gat caa gcc tat gag aaa ctc    1084
Ile Pro Val Val Pro Val Asp Lys Cys Asp Gln Ala Tyr Glu Lys Leu
    300                 305                 310 aac acc cct tca cta aaa aat ggg ata acg aat aac ttc ctt tgc gct    1132
Asn Thr Pro Ser Leu Lys Asn Gly Ile Thr Asn Asn Phe Leu Cys Ala
315                 320                 325                 330 gga ttg gaa gaa gga ggg aaa gac gct tgc caa ggc gat tct ggt gga    1180
Gly Leu Glu Glu Gly Gly Lys Asp Ala Cys Gln Gly Asp Ser Gly Gly
                335                 340                 345 ccg ttg atg cta gtg aac aac act agg tgg ata gta gta gga gtt gtg    1228
Pro Leu Met Leu Val Asn Asn Thr Arg Trp Ile Val Val Gly Val Val
            350                 355                 360 tcg ttc ggg cac aag tgt gcc gag gaa gga tat cct ggt gtg tac tcg    1276
Ser Phe Gly His Lys Cys Ala Glu Glu Gly Tyr Pro Gly Val Tyr Ser
        365                 370                 375 cgc gta gcg agt tac cta gac tgg atc gcg aaa gtt acg aac tcg tta    1324
Arg Val Ala Ser Tyr Leu Asp Trp Ile Ala Lys Val Thr Asn Ser Leu
    380                 385                 390 gat cat gcc gtc act aac tga ttgtgcgtta acaacatat tttgttgtga        1375
Asp His Ala Val Thr Asn
395             400 agaaatactg tccaaacgta actttgaac ttgtattatg tattaacgta ttataagttc    1435
tagttttggt ttcaaccact agatgacgca aatgctcgta ttgtccaaca gctttattcc    1495
ttttgaagaa tattttttcg cacctacaag cttgtgaaac ttgtagataa tagttattcg    1555
taattttctc attgttttta caattttgt gtgatctgtt tttttatttt aactttgaag    1615
taccggaatg aaaatattta attttatatt tcattaattc aaaacgtttt tgttctgggc    1675
tgccatgtaa attgtataat aagtcgtggt tgtttagtaa gttatattat cggtagagtg    1735
tacgttaaga tctgactgtg aattttgaag aaaaaccta catctaaaca ttttatcttt    1795
actgactgta gttatttatc tctaatgttc agcgtgttta gccagtaatg taaatgtgaa    1855
ttataattga ttaagtttg attgaaatgt tt                                 1887

<210> SEQ ID NO 16
<211> LENGTH: 400
<212> TYPE: PRT
<213> ORGANISM: Tachypleus tridentatus

<400> SEQUENCE: 16

Met Thr Trp Ile Cys Val Ile Thr Leu Phe Ala Leu Ala Ser Ala Thr
1               5                   10                  15

Leu Gly Asn Lys Val Ser Arg Val Gly Val Leu Phe Pro Lys Thr Arg
                20                  25                  30

Asn Asp Asn Glu Cys Thr Ala Arg Gly Gly Leu Lys Gly Ser Cys Lys
            35                  40                  45

Ser Leu Ile Asp Cys Pro Ser Val Leu Ala Thr Leu Lys Asp Ser Phe
        50                  55                  60

Pro Val Val Cys Ser Trp Asn Gly Arg Phe Gln Pro Ile Val Cys Cys
65                  70                  75                  80

Pro Asp Ala Ile Ala Pro Pro Val Thr Thr Thr Ala Val Thr Val
                85                  90                  95

Ile Ser Thr Lys Glu Pro Lys Leu Pro Arg Leu His Ile Ser Gly Cys
            100                 105                 110
```

```
Gly Lys Arg Lys Val Lys Ile Asp Ile Thr Thr Val Gly Arg Ser Gly
            115                 120                 125

Ser Pro Ile Leu Pro Pro Ile Ser Thr Pro Gln Asn Ser Thr Gly Gly
130                 135                 140

Arg Gly Ile Ile Ala Gly Val Glu Ala Lys Ile Gly Ala Trp Pro
145                 150                 155                 160

Trp Met Ala Ala Val Phe Val Lys Asn Phe Gly Ile Gly Arg Phe His
                165                 170                 175

Cys Ala Gly Ser Ile Ile Ser Asn Lys Tyr Ile Leu Ser Ala Ala His
                180                 185                 190

Ala Phe Leu Ile Gly Gly Arg Lys Leu Thr Pro Thr Arg Leu Ala Val
                195                 200                 205

Arg Val Gly Gly His Tyr Ile Lys Arg Gly Gln Glu Tyr Pro Val Lys
            210                 215                 220

Asp Val Ile Ile His Pro His Tyr Val Glu Lys Glu Asn Tyr Asn Asp
225                 230                 235                 240

Ile Ala Ile Ile Glu Leu Lys Glu Glu Leu Asn Phe Thr Asp Leu Val
                245                 250                 255

Asn Pro Ile Cys Leu Pro Asp Pro Glu Thr Val Thr Pro Leu Lys
                260                 265                 270

Asp Arg Ile Val Thr Ala Ala Gly Trp Gly Asp Leu Asp Phe Ser Gly
            275                 280                 285

Pro Arg Ser Gln Val Leu Arg Glu Val Ser Ile Pro Val Val Pro Val
            290                 295                 300

Asp Lys Cys Asp Gln Ala Tyr Glu Lys Leu Asn Thr Pro Ser Leu Lys
305                 310                 315                 320

Asn Gly Ile Thr Asn Asn Phe Leu Cys Ala Gly Leu Glu Gly Gly
                325                 330                 335

Lys Asp Ala Cys Gln Gly Asp Ser Gly Gly Pro Leu Met Leu Val Asn
                340                 345                 350

Asn Thr Arg Trp Ile Val Val Gly Val Val Ser Phe Gly His Lys Cys
                355                 360                 365

Ala Glu Glu Gly Tyr Pro Gly Val Tyr Ser Arg Val Ala Ser Tyr Leu
            370                 375                 380

Asp Trp Ile Ala Lys Val Thr Asn Ser Leu Asp His Ala Val Thr Asn
385                 390                 395                 400

<210> SEQ ID NO 17
<211> LENGTH: 2394
<212> TYPE: DNA
<213> ORGANISM: Tachypleus tridentatus
<220> FEATURE:
<221> NAME/KEY: CDS
<222> LOCATION: (57)..(2078)

<400> SEQUENCE: 17 gtgggggggtt tagttgaaac agtaaatacg ttaactgttt aatcttgtta attgca atg      59
                                                                 Met
                                                                  1 ttg gtg ttg ctg tgt tgt gtt gtt ttg cat gtt ggt gtt gca aga att      107
Leu Val Leu Leu Cys Cys Val Val Leu His Val Gly Val Ala Arg Ile
        5                   10                  15 tgc tgt agc cac gaa cca aag tgg cag ctc gtc tgg tcg gat gaa ttt      155
Cys Cys Ser His Glu Pro Lys Trp Gln Leu Val Trp Ser Asp Glu Phe
            20                  25                  30 acc aat gga ata agt tct gat tgg gaa ttt gaa atg ggc aat ggc ctc      203
```

-continued

```
            Thr Asn Gly Ile Ser Ser Asp Trp Glu Phe Glu Met Gly Asn Gly Leu
                 35                  40                  45 aat ggt tgg ggt aat aac gaa ctg caa tat tat cgt cgt gaa aat gcc        251
Asn Gly Trp Gly Asn Asn Glu Leu Gln Tyr Tyr Arg Arg Glu Asn Ala
 50                  55                  60                  65 caa gtt gag gga ggg aaa ctg gta att act gct aaa aga gaa gac tat        299
Gln Val Glu Gly Gly Lys Leu Val Ile Thr Ala Lys Arg Glu Asp Tyr
                     70                  75                  80 gat ggc ttc aaa tac act tct gct agg ctg aaa acc cag ttt gat aaa        347
Asp Gly Phe Lys Tyr Thr Ser Ala Arg Leu Lys Thr Gln Phe Asp Lys
                 85                  90                  95 tct tgg aag tat ggt aaa att gaa gcc aaa atg gcg att cca tca ttt        395
Ser Trp Lys Tyr Gly Lys Ile Glu Ala Lys Met Ala Ile Pro Ser Phe
            100                 105                 110 cgg gga gtc tgg gtg atg ttc tgg atg tca gga gac aac act aat tat        443
Arg Gly Val Trp Val Met Phe Trp Met Ser Gly Asp Asn Thr Asn Tyr
        115                 120                 125 gtt aga tgg cca tct tct ggt gaa att gac ttt att gaa cat aga aac        491
Val Arg Trp Pro Ser Ser Gly Glu Ile Asp Phe Ile Glu His Arg Asn
130                 135                 140                 145 act aac aat gaa aaa gtc aga gga act att cac tgg tcc act cct gac        539
Thr Asn Asn Glu Lys Val Arg Gly Thr Ile His Trp Ser Thr Pro Asp
                    150                 155                 160 ggt gct cat gcg cat cat aac aga gaa agt aat aca aat ggg att gat        587
Gly Ala His Ala His His Asn Arg Glu Ser Asn Thr Asn Gly Ile Asp
                165                 170                 175 tat cac att tat tct gta gag tgg aat tct tcc att gtt aaa tgg ttt        635
Tyr His Ile Tyr Ser Val Glu Trp Asn Ser Ser Ile Val Lys Trp Phe
            180                 185                 190 gtt aat gga aat caa tac ttt gaa gtg aaa att cag gga gga gta aat        683
Val Asn Gly Asn Gln Tyr Phe Glu Val Lys Ile Gln Gly Gly Val Asn
        195                 200                 205 ggg aaa agt gca ttt cgt aac aaa gtt ttc gtt att tta aac atg gcg        731
Gly Lys Ser Ala Phe Arg Asn Lys Val Phe Val Ile Leu Asn Met Ala
210                 215                 220                 225 att ggt gga aac tgg cca gga ttc gat gtt gct gac gag gct ttc cct        779
Ile Gly Gly Asn Trp Pro Gly Phe Asp Val Ala Asp Glu Ala Phe Pro
                    230                 235                 240 gct aaa atg tac att gat tat gtc cgt gta tac cag gat gcc agt aca        827
Ala Lys Met Tyr Ile Asp Tyr Val Arg Val Tyr Gln Asp Ala Ser Thr
                245                 250                 255 tct tct cct gtt ggg gat acc tct tta gat ggt tac tat ttt gtc caa        875
Ser Ser Pro Val Gly Asp Thr Ser Leu Asp Gly Tyr Tyr Phe Val Gln
            260                 265                 270 aac agg cac agt gaa ttg tat ctt gat gtc act gat gcc agt aac gaa        923
Asn Arg His Ser Glu Leu Tyr Leu Asp Val Thr Asp Ala Ser Asn Glu
        275                 280                 285 gat gga gca ttt ctg caa caa tgg tct tat agt ggt aat gag aac caa        971
Asp Gly Ala Phe Leu Gln Gln Trp Ser Tyr Ser Gly Asn Glu Asn Gln
290                 295                 300                 305 cag ttt gat ttt gag cat ctc gaa aat aat gtt tat aaa att act aat        1019
Gln Phe Asp Phe Glu His Leu Glu Asn Asn Val Tyr Lys Ile Thr Asn
                    310                 315                 320 aaa aaa agt gga aaa tct ttg gat gtt tat aat ttt ggg act gag aat        1067
Lys Lys Ser Gly Lys Ser Leu Asp Val Tyr Asn Phe Gly Thr Glu Asn
                325                 330                 335 ggt gtt aga atc caa cag tgg tca tat gga ggg gct cgc aat cag cag        1115
Gly Val Arg Ile Gln Gln Trp Ser Tyr Gly Gly Ala Arg Asn Gln Gln
            340                 345                 350
```

-continued

| | | |
|---|---|---|
| ttt act gta caa agt gtt ggt gat ggt tat tat aag att att cca cgc<br>Phe Thr Val Gln Ser Val Gly Asp Gly Tyr Tyr Lys Ile Ile Pro Arg<br>355                           360                       365 | 1163 |
| ggc agt gga aag tta gtg gaa gta gca gat ttt agt aaa gat gca gga<br>Gly Ser Gly Lys Leu Val Glu Val Ala Asp Phe Ser Lys Asp Ala Gly<br>370                         375                       380                  385 | 1211 |
| ggg aag ata caa caa tgg tct gat aac aac caa tta tct gga cag tgg<br>Gly Lys Ile Gln Gln Trp Ser Asp Asn Asn Gln Leu Ser Gly Gln Trp<br>                         390                       395                  400 | 1259 |
| aaa ctt att aaa agt aaa agt tat tct aaa tta att cag gca gaa agt<br>Lys Leu Ile Lys Ser Lys Ser Tyr Ser Lys Leu Ile Gln Ala Glu Ser<br>                   405                       410                  415 | 1307 |
| tat ttt gat tcc tca aaa gta caa ttg gaa gat acc tca gat gta gga<br>Tyr Phe Asp Ser Ser Lys Val Gln Leu Glu Asp Thr Ser Asp Val Gly<br>420                         425                       430 | 1355 |
| ggt ggg aag aat gtt aaa tgt gat aat gaa gga gcc tgg atg gct tat<br>Gly Gly Lys Asn Val Lys Cys Asp Asn Glu Gly Ala Trp Met Ala Tyr<br>               435                       440                  445 | 1403 |
| aag gat att gat ttc ccc agt tca ggt aat tat cga ata gaa tac aga<br>Lys Asp Ile Asp Phe Pro Ser Ser Gly Asn Tyr Arg Ile Glu Tyr Arg<br>450                         455                       460                  465 | 1451 |
| gta gca agt gaa cgt gca gga gga aag ctg tct ctg gat ttg aat gca<br>Val Ala Ser Glu Arg Ala Gly Gly Lys Leu Ser Leu Asp Leu Asn Ala<br>                         470                       475                  480 | 1499 |
| ggc tct ata gtt ctt ggc atg ctg gat gtt cct tca aca gga gga tgg<br>Gly Ser Ile Val Leu Gly Met Leu Asp Val Pro Ser Thr Gly Gly Trp<br>                          485                       490                  495 | 1547 |
| cag aag tgg acc acc att tcc cat aca gtg aat gtg gat tca ggt aca<br>Gln Lys Trp Thr Thr Ile Ser His Thr Val Asn Val Asp Ser Gly Thr<br>500                         505                       510 | 1595 |
| tat aac ttg ggg atc tat gtt caa cga gcc agc tgg aat atc aac tgg<br>Tyr Asn Leu Gly Ile Tyr Val Gln Arg Ala Ser Trp Asn Ile Asn Trp<br>               515                       520                  525 | 1643 |
| ata aag att aca aaa ata cct gaa cag tca aat ttg aat caa ggg cgt<br>Ile Lys Ile Thr Lys Ile Pro Glu Gln Ser Asn Leu Asn Gln Gly Arg<br>530                         535                       540                  545 | 1691 |
| cgt aat tct aaa tta att cag gca gaa agt tat ttt agt tac tca gaa<br>Arg Asn Ser Lys Leu Ile Gln Ala Glu Ser Tyr Phe Ser Tyr Ser Glu<br>                         550                       555                  560 | 1739 |
| gta caa ctg gaa gat acc tta gat gta gga ggt gga aag aat gtt aaa<br>Val Gln Leu Glu Asp Thr Leu Asp Val Gly Gly Gly Lys Asn Val Lys<br>                       565                       570                  575 | 1787 |
| tgt gat aaa gaa ggg gcc tgg atg gct tac aag gat att gat ttc ccc<br>Cys Asp Lys Glu Gly Ala Trp Met Ala Tyr Lys Asp Ile Asp Phe Pro<br>580                         585                       590 | 1835 |
| agt tca gga agt tat cga gta gaa tac aga gtg gca agt gaa cgt gca<br>Ser Ser Gly Ser Tyr Arg Val Glu Tyr Arg Val Ala Ser Glu Arg Ala<br>               595                       600                  605 | 1883 |
| gga gga aag ctg tcc cta gat ttg aat gca ggc tct ata gtg ctt ggc<br>Gly Gly Lys Leu Ser Leu Asp Leu Asn Ala Gly Ser Ile Val Leu Gly<br>610                         615                       620                  625 | 1931 |
| atg ctg gat att cct tca aca gga gga ttg cag aag tgg acc acc att<br>Met Leu Asp Ile Pro Ser Thr Gly Gly Leu Gln Lys Trp Thr Thr Ile<br>                         630                       635                  640 | 1979 |
| tct cat ata gtg aat gtg gat tta ggt aca tat aac ttg gga att tat<br>Ser His Ile Val Asn Val Asp Leu Gly Thr Tyr Asn Leu Gly Ile Tyr<br>                         645                       650                  655 | 2027 |
| gtt caa aaa gcc agt tgg aat atc aat tgg att aga att aca aaa gtg<br>Val Gln Lys Ala Ser Trp Asn Ile Asn Trp Ile Arg Ile Thr Lys Val<br>660                         665                       670 | 2075 |

```
tag gatacaagag caaaccaatt gtattatttt gaagaaacaa cagctgttga    2128
ccataatctt tgttcattga gaatttatcc aactgttata gaatctatca cctttccaga   2188
tgtacgcatt gctgatggtt ttgaactaat aaatgaggag attataagtg ctaatgtgtt   2248
tgttatatct ttaatttta aaacaaatt atcaactaac ttttcaattc aggcatggtg    2308
tttctctttt taatctgtat ttctaataaa ttaatgtctt taagagttgt tttgtttaca   2368
ataaataaag tttgattgtg tgggat                                        2394

<210> SEQ ID NO 18
<211> LENGTH: 673
<212> TYPE: PRT
<213> ORGANISM: Tachypleus tridentatus

<400> SEQUENCE: 18
```

Met Leu Val Leu Leu Cys Cys Val Val Leu His Val Gly Val Ala Arg
1               5                   10                  15

Ile Cys Cys Ser His Glu Pro Lys Trp Gln Leu Val Trp Ser Asp Glu
            20                  25                  30

Phe Thr Asn Gly Ile Ser Ser Asp Trp Glu Phe Glu Met Gly Asn Gly
        35                  40                  45

Leu Asn Gly Trp Gly Asn Asn Glu Leu Gln Tyr Tyr Arg Arg Glu Asn
    50                  55                  60

Ala Gln Val Glu Gly Gly Lys Leu Val Ile Thr Ala Lys Arg Glu Asp
65                  70                  75                  80

Tyr Asp Gly Phe Lys Tyr Thr Ser Ala Arg Leu Lys Thr Gln Phe Asp
                85                  90                  95

Lys Ser Trp Lys Tyr Gly Lys Ile Glu Ala Lys Met Ala Ile Pro Ser
            100                 105                 110

Phe Arg Gly Val Trp Val Met Phe Trp Met Ser Gly Asp Asn Thr Asn
        115                 120                 125

Tyr Val Arg Trp Pro Ser Ser Gly Glu Ile Asp Phe Ile Glu His Arg
    130                 135                 140

Asn Thr Asn Asn Glu Lys Val Arg Gly Thr Ile His Trp Ser Thr Pro
145                 150                 155                 160

Asp Gly Ala His Ala His His Asn Arg Glu Ser Asn Thr Asn Gly Ile
                165                 170                 175

Asp Tyr His Ile Tyr Ser Val Glu Trp Asn Ser Ser Ile Val Lys Trp
            180                 185                 190

Phe Val Asn Gly Asn Gln Tyr Phe Glu Val Lys Ile Gln Gly Gly Val
        195                 200                 205

Asn Gly Lys Ser Ala Phe Arg Asn Lys Val Phe Val Ile Leu Asn Met
    210                 215                 220

Ala Ile Gly Gly Asn Trp Pro Gly Phe Asp Val Ala Asp Glu Ala Phe
225                 230                 235                 240

Pro Ala Lys Met Tyr Ile Asp Tyr Val Arg Val Tyr Gln Asp Ala Ser
                245                 250                 255

Thr Ser Ser Pro Val Gly Asp Thr Ser Leu Asp Gly Tyr Tyr Phe Val
            260                 265                 270

Gln Asn Arg His Ser Glu Leu Tyr Leu Asp Val Thr Asp Ala Ser Asn
        275                 280                 285

Glu Asp Gly Ala Phe Leu Gln Gln Trp Ser Tyr Ser Gly Asn Glu Asn
    290                 295                 300

Gln Gln Phe Asp Phe Glu His Leu Glu Asn Asn Val Tyr Lys Ile Thr

```
              305                 310                 315                 320

Asn Lys Lys Ser Gly Lys Ser Leu Asp Val Tyr Asn Phe Gly Thr Glu
                    325                 330                 335

Asn Gly Val Arg Ile Gln Gln Trp Ser Tyr Gly Gly Ala Arg Asn Gln
                340                 345                 350

Gln Phe Thr Val Gln Ser Val Gly Asp Gly Tyr Tyr Lys Ile Ile Pro
                    355                 360                 365

Arg Gly Ser Gly Lys Leu Val Glu Val Ala Asp Phe Ser Lys Asp Ala
                370                 375                 380

Gly Gly Lys Ile Gln Gln Trp Ser Asp Asn Gln Leu Ser Gly Gln
        385                 390                 395                 400

Trp Lys Leu Ile Lys Ser Lys Ser Tyr Ser Lys Leu Ile Gln Ala Glu
                        405                 410                 415

Ser Tyr Phe Asp Ser Ser Lys Val Gln Leu Glu Asp Thr Ser Asp Val
                    420                 425                 430

Gly Gly Gly Lys Asn Val Lys Cys Asp Asn Glu Gly Ala Trp Met Ala
                    435                 440                 445

Tyr Lys Asp Ile Asp Phe Pro Ser Ser Gly Asn Tyr Arg Ile Glu Tyr
                    450                 455                 460

Arg Val Ala Ser Glu Arg Ala Gly Gly Lys Leu Ser Leu Asp Leu Asn
        465                 470                 475                 480

Ala Gly Ser Ile Val Leu Gly Met Leu Asp Val Pro Ser Thr Gly Gly
                        485                 490                 495

Trp Gln Lys Trp Thr Thr Ile Ser His Thr Val Asn Val Asp Ser Gly
                    500                 505                 510

Thr Tyr Asn Leu Gly Ile Tyr Val Gln Arg Ala Ser Trp Asn Ile Asn
                    515                 520                 525

Trp Ile Lys Ile Thr Lys Ile Pro Glu Gln Ser Asn Leu Asn Gln Gly
                    530                 535                 540

Arg Arg Asn Ser Lys Leu Ile Gln Ala Glu Ser Tyr Phe Ser Tyr Ser
        545                 550                 555                 560

Glu Val Gln Leu Glu Asp Thr Leu Asp Val Gly Gly Lys Asn Val
                        565                 570                 575

Lys Cys Asp Lys Glu Gly Ala Trp Met Ala Tyr Lys Asp Ile Asp Phe
                    580                 585                 590

Pro Ser Ser Gly Ser Tyr Arg Val Glu Tyr Arg Val Ala Ser Glu Arg
                    595                 600                 605

Ala Gly Gly Lys Leu Ser Leu Asp Leu Asn Ala Gly Ser Ile Val Leu
                610                 615                 620

Gly Met Leu Asp Ile Pro Ser Thr Gly Gly Leu Gln Lys Trp Thr Thr
        625                 630                 635                 640

Ile Ser His Ile Val Asn Val Asp Leu Gly Thr Tyr Asn Leu Gly Ile
                        645                 650                 655

Tyr Val Gln Lys Ala Ser Trp Asn Ile Asn Trp Ile Arg Ile Thr Lys
                    660                 665                 670

Val

<210> SEQ ID NO 19
<211> LENGTH: 1979
<212> TYPE: DNA
<213> ORGANISM: Tachypleus tridentatus
<220> FEATURE:
<221> NAME/KEY: CDS
<222> LOCATION: (101)..(1030)
```

<400> SEQUENCE: 19

| | | |
|---|---|---|
| gaagacaaga gagttgaaac aaccatagcc tgtttgctta tgactttcaa taagagatac | 60 | |

| | | |
|---|---|---|
| tcggcttaaa gggaactgac ttattcgtag aggctatacc atg gat atc agt ttc | 115 | |
| | Met Asp Ile Ser Phe | |
| | 1               5 | |

| | |
|---|---|
| ctg gtt ttt atc aca ctg tct atg gct ctc ttc tcg agc aac gtg aca | 163 |
| Leu Val Phe Ile Thr Leu Ser Met Ala Leu Phe Ser Ser Asn Val Thr | |
|         10              15              20 | |

| | |
|---|---|
| gga acg tca gta aca tca agg gta cga cgt gga ata aat gaa aaa cat | 211 |
| Gly Thr Ser Val Thr Ser Arg Val Arg Arg Gly Ile Asn Glu Lys His | |
|     25              30              35 | |

| | |
|---|---|
| tgt ggg ttc cga cca gta att aca aga att att ggt gga gga ata gcg | 259 |
| Cys Gly Phe Arg Pro Val Ile Thr Arg Ile Ile Gly Gly Gly Ile Ala | |
| 40              45              50 | |

| | |
|---|---|
| acg cct cat tca tgg ccg tgg atg gtt gga att ttc aaa gta aat cct | 307 |
| Thr Pro His Ser Trp Pro Trp Met Val Gly Ile Phe Lys Val Asn Pro | |
| 55              60              65 | |

| | |
|---|---|
| cac cgt ttc ctt tgt ggt gga tct att att aat aaa gtc tct gtt gtt | 355 |
| His Arg Phe Leu Cys Gly Gly Ser Ile Ile Asn Lys Val Ser Val Val | |
| 70              75              80              85 | |

| | |
|---|---|
| act gcc gcc cat tgt ctt gtg acg cag ttt gga aac aga cag aat tat | 403 |
| Thr Ala Ala His Cys Leu Val Thr Gln Phe Gly Asn Arg Gln Asn Tyr | |
|         90              95             100 | |

| | |
|---|---|
| tct atc ttc gta aga gtt gga gcc cat gac ata gac aat tcg ggt aca | 451 |
| Ser Ile Phe Val Arg Val Gly Ala His Asp Ile Asp Asn Ser Gly Thr | |
|         105             110             115 | |

| | |
|---|---|
| aat tat caa gtg gat aaa gtt att gtt cac cag ggc tac aaa cac cat | 499 |
| Asn Tyr Gln Val Asp Lys Val Ile Val His Gln Gly Tyr Lys His His | |
|     120             125             130 | |

| | |
|---|---|
| tca cac tac tac gat atc ggt ttg att tta ctc tcg aaa cca gtc gaa | 547 |
| Ser His Tyr Tyr Asp Ile Gly Leu Ile Leu Leu Ser Lys Pro Val Glu | |
| 135             140             145 | |

| | |
|---|---|
| tac aac gac aaa ata cag cct gtc tgt att cct gag ttc aac aaa cct | 595 |
| Tyr Asn Asp Lys Ile Gln Pro Val Cys Ile Pro Glu Phe Asn Lys Pro | |
| 150             155             160             165 | |

| | |
|---|---|
| cac gtg aac ttg aac aat att aag gtc gtc att act ggt tgg ggt gtt | 643 |
| His Val Asn Leu Asn Asn Ile Lys Val Val Ile Thr Gly Trp Gly Val | |
|         170             175             180 | |

| | |
|---|---|
| act ggg aaa gct act gag aaa cgt aac gtt ctt cgt gaa ttg gag ttg | 691 |
| Thr Gly Lys Ala Thr Glu Lys Arg Asn Val Leu Arg Glu Leu Glu Leu | |
|         185             190             195 | |

| | |
|---|---|
| ccc gtg gtt aca aac gaa cag tgc aac aaa tct tat cag aca ctc cca | 739 |
| Pro Val Val Thr Asn Glu Gln Cys Asn Lys Ser Tyr Gln Thr Leu Pro | |
|     200             205             210 | |

| | |
|---|---|
| ttc tca aaa ttg aac cga gga atc act aac gac atg att tgt gcg ggg | 787 |
| Phe Ser Lys Leu Asn Arg Gly Ile Thr Asn Asp Met Ile Cys Ala Gly | |
| 215             220             225 | |

| | |
|---|---|
| ttt ccg gaa gga ggg aaa gat gct tgt cag ggc gac tct ggt ggt ccc | 835 |
| Phe Pro Glu Gly Gly Lys Asp Ala Cys Gln Gly Asp Ser Gly Gly Pro | |
| 230             235             240             245 | |

| | |
|---|---|
| ctg atg tat cag aat cca aca aca gga aga gtg aaa ata gtt gga gtt | 883 |
| Leu Met Tyr Gln Asn Pro Thr Thr Gly Arg Val Lys Ile Val Gly Val | |
|         250             255             260 | |

| | |
|---|---|
| gta tca ttt ggg ttc gaa tgt gct cgt ccc aac ttc ccc ggt gtt tac | 931 |
| Val Ser Phe Gly Phe Glu Cys Ala Arg Pro Asn Phe Pro Gly Val Tyr | |
|         265             270             275 | |

| | |
|---|---|
| acg cgc ctc tcg agc tac gtt aac tgg ctc cag gaa atc acc ttc gga | 979 |
| Thr Arg Leu Ser Ser Tyr Val Asn Trp Leu Gln Glu Ile Thr Phe Gly | |
|     280             285             290 | |

```
cag tca ctc gct tct tta ttt gaa gtt gta cca ata ttt ata ccc gag    1027
Gln Ser Leu Ala Ser Leu Phe Glu Val Val Pro Ile Phe Ile Pro Glu
    295                 300                 305 tga gactgaagat aaatattgaa gagaaatcta gaataatgta caatataaga         1080
agcctgaaat tactgaaata gaaaggcgcg tgatgagaaa tacgtttcaa attttatttt  1140
ttattaactt tattgtgttt aactattctt tacgtgggac atgaaatata aatctttatt  1200
tcttctttat atactttaga ttttcatttc atctatcttt atcagttttg taatgttact  1260
aataatattt cttatggcac ggatcgagcc tcgtgaatca cagtaaataa taataattat  1320
aaaatcacac attattaaaa gcaatagcat tcagagtgag taacatataa acttcactat  1380
gagtggactt ttttattcac attttaagtt cattactaac tgttgggagg tctttatatt  1440
gttgtatatt tatatattaa ttaggttggt ttagtacatt ttgttgtaatg gtggaatagg  1500 gcgtaggttt taaatgtgtt tgcaaaaaaa caaacaaaac aagtaatggt ggatgatggt  1560
tccaaagtaa ccgaaagaac actttgaaca tttttataca aaaatttatg ttttaaaata  1620
cgagtatata caatcgatct ctaagtacaa gaaaaactga agtgttcatt caggtttaac  1680
agtgcaactt aaatcaacag ttagttgttc actaaacatt acaatttgat cctttataaa  1740
cgctaatact gtttaaacag tcagtaataa tacagtatca tagcatatca tatatgaagg  1800
tattttaaca ttctatatac aaagccagaa ttgaaaacgg taatattttg tacgattagt  1860
gaattattgt ttttaagaac aaactggtat caaatttaaa atatgaatct gtgatttaat  1920
attttttaca acgttctaac ttaccacttt tgttgtgaat aaaggtgttt acaaatgga   1979

<210> SEQ ID NO 20
<211> LENGTH: 309
<212> TYPE: PRT
<213> ORGANISM: Tachypleus tridentatus

<400> SEQUENCE: 20

Met Asp Ile Ser Phe Leu Val Phe Ile Thr Leu Ser Met Ala Leu Phe
1               5                   10                  15

Ser Ser Asn Val Thr Gly Thr Ser Val Thr Ser Arg Val Arg Arg Gly
            20                  25                  30

Ile Asn Glu Lys His Cys Gly Phe Arg Pro Val Ile Thr Arg Ile Ile
        35                  40                  45

Gly Gly Gly Ile Ala Thr Pro His Ser Trp Pro Trp Met Val Gly Ile
    50                  55                  60

Phe Lys Val Asn Pro His Arg Phe Leu Cys Gly Gly Ser Ile Ile Asn
65                  70                  75                  80

Lys Val Ser Val Val Thr Ala Ala His Cys Leu Val Thr Gln Phe Gly
                85                  90                  95

Asn Arg Gln Asn Tyr Ser Ile Phe Val Arg Val Gly Ala His Asp Ile
            100                 105                 110

Asp Asn Ser Gly Thr Asn Tyr Gln Val Asp Lys Val Ile Val His Gln
        115                 120                 125

Gly Tyr Lys His His Ser His Tyr Tyr Asp Ile Gly Leu Ile Leu Leu
    130                 135                 140

Ser Lys Pro Val Glu Tyr Asn Asp Lys Ile Gln Pro Val Cys Ile Pro
145                 150                 155                 160

Glu Phe Asn Lys Pro His Val Asn Leu Asn Asn Ile Lys Val Val Ile
                165                 170                 175

Thr Gly Trp Gly Val Thr Gly Lys Ala Thr Glu Lys Arg Asn Val Leu
```

```
                          180                 185                 190
Arg Glu Leu Glu Leu Pro Val Val Thr Asn Glu Gln Cys Asn Lys Ser
        195                 200                 205

Tyr Gln Thr Leu Pro Phe Ser Lys Leu Asn Arg Gly Ile Thr Asn Asp
    210                 215                 220

Met Ile Cys Ala Gly Phe Pro Glu Gly Gly Lys Asp Ala Cys Gln Gly
225                 230                 235                 240

Asp Ser Gly Gly Pro Leu Met Tyr Gln Asn Pro Thr Thr Gly Arg Val
                245                 250                 255

Lys Ile Val Gly Val Ser Phe Gly Phe Glu Cys Ala Arg Pro Asn
        260                 265                 270

Phe Pro Gly Val Tyr Thr Arg Leu Ser Ser Tyr Val Asn Trp Leu Gln
    275                 280                 285

Glu Ile Thr Phe Gly Gln Ser Leu Ala Ser Leu Phe Glu Val Val Pro
        290                 295                 300

Ile Phe Ile Pro Glu
305

<210> SEQ ID NO 21
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 21
taatcgcgat ctagaatgtt ggtgaataac gtgttttcac tactgtgttt cccactcttg      60
atgtctgtgg ttagatgcag tactctcagc agacagcgta gacagtttgt tttccctgac     120
gaggaagaac tttgctcaaa ccgatttact gaagaaggaa catgcaaaaa tgtcttggat     180
tgtagaatac ttttacaaaa aaatgattat aatttactca agaatcaat atgcggcttt     240 gaaggcataa cacccaaagt tgttgtccg aaatcaagcc atgtaatttc aagtacacag      300

<210> SEQ ID NO 22
<211> LENGTH: 360
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t

<400> SEQUENCE: 22
cncntnacaa gcggtcttat tattaaatct agtgatggtg atggtgatgc accatatgtt      60
ctgcaatcca atctaaaaac tctgtcactt ttgtgtaaac cccaggaaat ccaggcaatg     120
cgcatttctt tccgaaagac acaattccaa tgagataaaa ctctccggtt ttaacaggca     180
acatcattgg acctccagaa tcaccctggc aagcatcctt cccgccatct gcaaagccag     240
```

```
cacacatata cacgtttgta atatttaaat ccttctcgta ggcctgtcta caggcctcgt    300
gttcccatat tggtaactgt acttctctca acactgcact agatgggccg ttaaatgctg    360
```